US009274001B2

(12) United States Patent
Wax et al.

(10) Patent No.: US 9,274,001 B2
(45) Date of Patent: Mar. 1, 2016

(54) DUAL WINDOW PROCESSING SCHEMES FOR SPECTROSCOPIC OPTICAL COHERENCE TOMOGRAPHY (OCT) AND FOURIER DOMAIN LOW COHERENCE INTERFEROMETRY

(75) Inventors: Adam Wax, Chapel Hill, NC (US); Robert N. Graf, Montclair, NJ (US); Francisco E. Robles, Durham, NC (US)

(73) Assignee: Duke University, Durham, NC (US)

( * ) Notice: Subject to any disclaimer, the term of this patent is extended or adjusted under 35 U.S.C. 154(b) by 302 days.

(21) Appl. No.: 13/574,484

(22) PCT Filed: Jan. 24, 2011

(86) PCT No.: PCT/US2011/022271
§ 371 (c)(1),
(2), (4) Date: Feb. 13, 2013

(87) PCT Pub. No.: WO2011/091369
PCT Pub. Date: Jul. 28, 2011

(65) Prior Publication Data
US 2013/0135614 A1    May 30, 2013

Related U.S. Application Data

(60) Provisional application No. 61/297,588, filed on Jan. 22, 2010.

(51) Int. Cl.
*G01J 3/45* (2006.01)
*G01B 9/02* (2006.01)
(Continued)

(52) U.S. Cl.
CPC .............. *G01J 3/45* (2013.01); *G01B 9/02044* (2013.01); *G01B 9/02084* (2013.01);
(Continued)

(58) Field of Classification Search
CPC ........... G01B 9/02091; G01B 9/02044; G01B 9/02084; G01B 9/02087; G01N 21/49; G01J 3/453; G01J 3/45; G01J 200/4538
USPC ........... 356/227.19, 227.23, 227.27, 450–521
See application file for complete search history.

(56) References Cited

U.S. PATENT DOCUMENTS 2,469,906 A    5/1949  Wallace
4,646,722 A    3/1987  Silverstein et al.
(Continued)

FOREIGN PATENT DOCUMENTS

CN    12836086 A    2/2001
EP    0243005 A2   10/1987
(Continued)

OTHER PUBLICATIONS

Duke University, Australian Application No. 2011207444, Examination Report No. 1, Nov. 14, 2013.
(Continued)

*Primary Examiner* — Michael P Lapage
(74) *Attorney, Agent, or Firm* — Olive Law Group, PLLC

(57) ABSTRACT

Current apparatuses and methods for analysis of spectroscopic optical coherence tomography (SOCT) signals suffer from an inherent tradeoff between time (depth) and frequency (wavelength) resolution. In one non-limiting embodiment, multiple or dual window (DW) apparatuses and methods for reconstructing time-frequency distributions (TFDs) that applies two windows that independently determine the optical and temporal resolution is provided. For example, optical resolution may relate to scattering information about a sample, and temporal resolution may be related to absorption or depth related information. The effectiveness of the apparatuses and methods is demonstrated in simulations and in processing of measured OCT signals that contain fields which vary in time and frequency. The DW technique may yield TFDs that maintain high spectral and temporal resolution and are free from the artifacts and limitations commonly observed with other processing methods.

52 Claims, 40 Drawing Sheets

(51) Int. Cl.
*G01N 21/49* (2006.01)
*G01J 3/453* (2006.01)

(52) U.S. Cl.
CPC ....... *G01B 9/02087* (2013.01); *G01B 9/02091* (2013.01); *G01J 3/453* (2013.01); *G01N 21/49* (2013.01); *G01J 2003/4538* (2013.01)

(56) References Cited

U.S. PATENT DOCUMENTS

| | | | |
|---|---|---|---|
| 4,699,513 | A | 10/1987 | Brooks et al. |
| 4,741,326 | A | 5/1988 | Sidall et al. |
| 5,184,602 | A | 2/1993 | Anapliotis et al. |
| 5,193,525 | A | 3/1993 | Silverstein et al. |
| 5,386,817 | A | 2/1995 | Jones |
| 5,489,256 | A | 2/1996 | Adair |
| 5,534,707 | A | 7/1996 | Pentoney |
| 5,565,986 | A | 10/1996 | Knuttel |
| 5,601,087 | A | 2/1997 | Gunderson et al. |
| 5,643,175 | A | 7/1997 | Adair |
| 5,771,327 | A | 6/1998 | Bar-Or et al. |
| 5,930,440 | A | 7/1999 | Bar-Or |
| 5,956,355 | A | 9/1999 | Swanson et al. |
| 6,002,480 | A | 12/1999 | Izatt et al. |
| 6,091,984 | A | 7/2000 | Perelman et al. |
| 6,134,003 | A | 10/2000 | Tearney et al. |
| 6,174,291 | B1 | 1/2001 | McMahon et al. |
| 6,233,373 | B1 | 5/2001 | Askins et al. |
| 6,263,133 | B1 | 7/2001 | Hamm |
| 6,404,497 | B1 | 6/2002 | Backman et al. |
| 6,447,444 | B1 | 9/2002 | Avni et al. |
| 6,501,551 | B1 | 12/2002 | Tearney et al. |
| 6,564,087 | B1 | 5/2003 | Pitris et al. |
| 6,624,890 | B2 | 9/2003 | Backman et al. |
| 6,697,652 | B2 | 2/2004 | Georgakoudi et al. |
| 6,768,554 | B2 * | 7/2004 | Ge ................................ 356/512 |
| 6,775,007 | B2 | 8/2004 | Izatt et al. |
| 6,812,478 | B2 * | 11/2004 | Amartur .................. 250/559.29 |
| 6,847,456 | B2 | 1/2005 | Yang et al. |
| 6,853,457 | B2 | 2/2005 | Bjarklev et al. |
| 6,855,107 | B2 | 2/2005 | Avni et al. |
| 6,863,651 | B2 | 3/2005 | Remijan et al. |
| 6,879,741 | B2 | 4/2005 | Salerno et al. |
| 7,061,622 | B2 | 6/2006 | Rollins et al. |
| 7,079,254 | B2 | 7/2006 | Kane et al. |
| 7,102,758 | B2 | 9/2006 | Wax |
| 7,190,464 | B2 | 3/2007 | Alphonse |
| 7,355,716 | B2 | 4/2008 | De Boer et al. |
| 7,366,372 | B2 | 4/2008 | Lange |
| 7,391,520 | B2 | 6/2008 | Zhou et al. |
| 7,417,740 | B2 | 8/2008 | Alphonse et al. |
| 7,428,050 | B2 | 9/2008 | Giakos |
| 7,428,052 | B2 | 9/2008 | Fujita |
| 7,595,889 | B2 | 9/2009 | Wax et al. |
| 7,616,323 | B2 | 11/2009 | De Lega et al. |
| 7,633,627 | B2 | 12/2009 | Choma et al. |
| 7,636,168 | B2 | 12/2009 | De Lega et al. |
| 7,761,139 | B2 | 7/2010 | Tearney et al. |
| 7,884,947 | B2 | 2/2011 | De Lega et al. |
| 7,903,254 | B2 | 3/2011 | Wax et al. |
| RE42,497 | E * | 6/2011 | Wax .............................. 356/497 |
| 2002/0143243 | A1 | 10/2002 | Georgakoudi et al. |
| 2002/0171831 | A1 | 11/2002 | Backman et al. |
| 2002/0188204 | A1 | 12/2002 | McNamara et al. |
| 2003/0042438 | A1 | 3/2003 | Lawandy et al. |
| 2003/0137669 | A1 | 7/2003 | Rollins et al. |
| 2003/0153866 | A1 | 8/2003 | Long et al. |
| 2003/0160969 | A1 * | 8/2003 | Endo et al. .................... 356/520 |
| 2003/0187349 | A1 | 10/2003 | Kaneko et al. |
| 2004/0215296 | A1 | 10/2004 | Ganz et al. |
| 2004/0223162 | A1 | 11/2004 | Wax |
| 2005/0000525 | A1 | 1/2005 | Klimberg et al. |
| 2005/0004453 | A1 | 1/2005 | Tearney et al. |
| 2005/0053974 | A1 | 3/2005 | Lakowicz et al. |
| 2005/0182291 | A1 | 8/2005 | Hirata |
| 2006/0132790 | A1 | 6/2006 | Gutin |
| 2006/0158657 | A1 | 7/2006 | De Lega et al. |
| 2006/0158659 | A1 | 7/2006 | Colonna De Lega et al. |
| 2006/0164643 | A1 | 7/2006 | Giakos |
| 2006/0241577 | A1 | 10/2006 | Balbierz et al. |
| 2006/0256343 | A1 | 11/2006 | Choma et al. |
| 2006/0285635 | A1 | 12/2006 | Boppart et al. |
| 2007/0002327 | A1 | 1/2007 | Zhou et al. |
| 2007/0015969 | A1 | 1/2007 | Feldman et al. |
| 2007/0027391 | A1 | 2/2007 | Kohno |
| 2007/0086013 | A1 | 4/2007 | De Lega et al. |
| 2007/0091318 | A1 | 4/2007 | Freishlad et al. |
| 2007/0133002 | A1 | 6/2007 | Wax et al. |
| 2007/0139656 | A1 | 6/2007 | Wan |
| 2007/0165234 | A1 | 7/2007 | Podoleanu |
| 2007/0201033 | A1 | 8/2007 | Desjardins et al. |
| 2007/0270792 | A1 | 11/2007 | Hennemann et al. |
| 2008/0037024 | A1 | 2/2008 | Backman et al. |
| 2008/0058629 | A1 | 3/2008 | Seibel et al. |
| 2008/0174784 | A1 | 7/2008 | Colonna De Lega et al. |
| 2008/0249369 | A1 | 10/2008 | Seibel et al. |
| 2008/0255461 | A1 | 10/2008 | Weersink et al. |
| 2009/0009759 | A1 | 1/2009 | Backman et al. |
| 2009/0073456 | A1 | 3/2009 | Wax et al. |
| 2009/0075391 | A1 | 3/2009 | Fulghum, Jr. |
| 2010/0150467 | A1 * | 6/2010 | Zhao et al. .................... 382/264 |

FOREIGN PATENT DOCUMENTS

| | | |
|---|---|---|
| EP | 1021126 B1 | 7/2004 |
| JP | 61210910 A | 9/1986 |
| JP | 2001521806 A | 11/2001 |
| JP | 2010539491 A | 2/2003 |
| JP | 2009511909 A | 3/2009 |
| JP | 2009527770 A | 7/2009 |
| JP | 2003035660 A | 12/2010 |
| WO | 99-18845 A1 | 4/1999 |
| WO | 00-42912 A1 | 7/2000 |
| WO | 2004066825 A2 | 8/2004 |
| WO | 2007-133684 A2 | 11/2007 |

OTHER PUBLICATIONS

Terry, N., et al., "Detection of intestinal dysplasia using angle-resolved low coherence interferometry." Journal of Biomedical Optics, Oct. 2011, vol. 16(10), pp. 106002.

Wax, Adam, Real-time a/LCI measurements for detecting pre-cancerous cells, Optical Society of America FiO and Laser Science Frontiers in Optics 2004 and Laser Science XX, Oct. 10-14, 2004.

Pyhtila, J., et al., Real-time data acquisition angle-resolved low coherence interferometry system, Biomedical Engineering Society, 2004 BMES Annual Fall Meeting, Biomedical Engineering: New Challenges for the Future, Oct. 13-16, 2004.

Bouma, Brett Eugene, Declaration Under 37 C.F.R. 1.131 filed in U.S. Appl. No. 11/677,278, Feb. 1, 2010.

Schmitt, J.M., Array detection for speckle reduction in optical coherence microscopy, Phys. Med. Biol., 1997, pp. 1427-1439, vol. 42.

Desjardins, A.E., et al., Speckle reduction in OCT using massively-parallel detection and frequency-domain ranging, Optics Express, May 29, 2006, pp. 4736-4745, vol. 14, No. 11.

Tuchin, V., Tissue Optics: Light Scattering Methods and Instruments for Medical Diagnosis, 2000, pp. 40-44, 91-98.

Vabre, L, et al., Imagery of local defects in multilayer components by short coherence length interferometry, Optics Letters, pp. 1899-1901, Nov. 1, 2002, vol. 27, No. 21.

Duke University, International Application No. PCT/US2011/022271, International Search Report, Apr. 23, 2011.

Duke University, International Application No. PCT/US2011/022271, International Preliminary Report on Patentability, Jul. 24, 2012.

Xie, Tuqiang et al., "Fiber-Optic-Bundle-Based Optical Coherehence Tomography," Optic Letters, vol. 30, No. 14, Jul. 15, 2005.

Pyhtila, John W. et al., "Fourier-Domain Angle-Resolved Low Coherence Interferometry Through an Endoscopic Fiber Bundle for Light-Scattering Spectroscopy," Optics Letters, vol. 31, No. 6, Mar. 15, 2006.

(56) References Cited

OTHER PUBLICATIONS

Pyhtila, John W. et al., "Rapid, Depth-Resolved Light Scattering Measurements using Fourier Domain, Angle Resolved Low Coherence Interferometry," Optics Express, vol. 12, No. 25, Dec. 13, 2004.

Pyhtila, John W. et al., "Determining Nuclear Morphology Using an Improved Angle-Resolved Low Coherence Interferometry System," Optics Express, vol. 11, No. 25, Dec. 15, 2003.

Hausler, G. et al., "Coherence Radar and Spectral Radar—New Tools for Dermatological Diagnosis," Journal of Biomedical Optics, vol. 3, Jan. 1998.

Wax, Adam et al., "Cellular Organization and Substructure Measured Using Angle-Resolved Low-Coherence Interferometry," Biophysical Journal, Apr. 2002, pp. 2256-2264, vol. 82.

Pyhtila, John W. et al., "Experimental Calibration of a New Angle-Resolved Low Coherence Interferometry System," http://www.fitzpatrick.duke.edu/Events/AnnualMeetings/04.ThePhysicalNatureofInformation/posters/htm, 2003.

Wax, Adam et al., "Measurement of Angular Distributions by Use of Low-Coherence Interferometry for Light-Scattering Spectroscopy," Optics Letters, Mar. 15, 2001, pp. 322-324, vol. 26, No. 6.

Wax, Adam et al., "Determination of Particle Size Using the Angular Distribtion of Backscattered Light as Measured with Low-Coherence Interferometry," Journal of the Optical Society of America, Apr. 2002, pp. 737-744, vol. 19, No. 4.

Wax, Adam et al., "In Situ Detection of Neoplastic Transformation and Chemopreventive Effects in Rat Esophagus Epithelium Using Angle-Resolved Low-Coherence Interferometry," Cancer Research, Jul. 1, 2003, pp. 3556-3559, vol. 63, No. 13.

Leitgeb, R. et al., "Performance of Fourier Domain vs. Time Domain Optical Coherence Tomography," Optics Express, vol. 11, No. 8, Apr. 21, 2003, pp. 889-894.

de Boer, Johannes F. et al., "Improved Signal-To-Noise Ratio in Spectral-Domain Compared with Time-Domain Optical Coherence Tomography," Optics Letters, vol. 28, No. 21, Nov. 1, 2003, pp. 2067-2069, http://oa.osa.org/abstract.cfr?id=86605.

Choma, Michael A. et al., "Sensitivity Advantage of Swept Source and Fourier Domain Optical Coherence Tomography," Optics Express, vol. 11, No. 18, Sep. 8, 2003, pp. 2183-2189.

Kim, Y.L. et al., "Simultaneous Measurement of Angular and Spectral Properties of Light Scattering for Characterization of Tissue Microarchitecture and its Alteration in Early Precancer," IEEE Journal of Selected Topics in Quantum Electronics, vol. 9, Issue 2, Mar./Apr. 2003, pp. 243-256, http://ieeexplore.ieee.org/xpl/freeabs_all.jsp?tp=&arnumber=1238988&isnumber=27791.

Roy, Hemant K. et al., "Four-Dimensional Elastic Light-Scattering Fingerprints as Preneoplastic Markers in the Rat Model of Colon Carcinogenesis," Gastroenterology, vol. 126, Issue 4, Apr. 2004, pp. 1071-1081, http://www.gastrojournal.org/article/PIIS0016508501000290/abstract.

Wax, Adam et al., "In Situ Monitoring of Neoplastic Transformation and Assessing Efficacy of Chemopreventive Agents in Rat Esophagus Epithelium Using Angle-Resolved Low-Coherence Interferometry," Abstract as presented to the American Association for Cancer Research at their 2004 Annual Meeting, Mar. 27, 2004.

Wax, Adam et al., "Prospective Grading of Neoplastic Change in Rat Esophagus Epithelium Using Angle-Resolved Low-Coherence Interferometry," Journal of Biomedical Optics, vol. 10(5), Sep./Oct. 2005, pp. 051604-1 through 051604-10.

Brown, William J. et al., "Review and Recent Development of Angle-Resolved Low-Coherence Interferometry for Detection of Precancerous Cells in Human Esophageal Epithelium," IEEE Journal of Selected Topics in Quantum Electronics, vol. 14, No. 1, Jan./Feb. 2008, pp. 88-97.

Wax, Adam et al., "Fourier-Domain Low-Coherence Interferometry for Light-Scattering Spectroscopy," Optic Letters, vol. 28, No. 14, Jul. 15, 2003, pp. 1230-1232.

Backman, V. et al., "Measuring Cellular Structure at Submicrometer Scale with Light Scattering Spectroscopy," IEEE J. Sel. Top. Quantum Electron, vol. 7, Issue 6, Nov./Dec. 2001, pp. 887-893.

Backman, V. et al., "Detection of Preinvasive Cancer Cells," Nature 406, Jul. 6, 2000, pp. 35-36.

Wojtkowski, M. et al., "Full Range Complex Spectral Optical Coherence Tomography Technique in Eye Imaging," Optics Letters, vol. 27, Issue 16, Aug. 15, 2002, pp. 1415-1417.

Wojtkowski, M. et al., "In Vivo Human Retinal Imaging by Fourier Domain Optical Coherence Tomography," J. Biomed. Opt., Vol. 7, No. 3, Jul. 1, 2002, pp. 457-463.

Leitgeb, R. et al., "Spectral Measurement of Absorption by Spectroscopic Frequency-Domain Optical Coherence Tomography," Optic Letters, vol. 25, Issue 11, Jun. 1, 2000, pp. 820-822.

Morgner, U. et al., "Spectroscopic Optical Coherence Tomography," Optic Letters, vol. 25, Issue 2, Jan. 15, 2000, pp. 111-113.

Amoozegar, Cyrus et al., "Experimental Verification of T-matrix-based Inverse Light Scattering Analysis for Assessing Structure of Spheroids as Models of Cell Nuclei," Applied Optics, vol. 48, No. 10, Apr. 1, 2009, 7 pages.

Graf, R. N. et al., "Parallel Frequency-Domain Optical Coherence Tomography Scatter-Mode Imaging of the Hamster Cheek Pouch Using a Thermal Light Source," Optics Letters, vol. 33, No. 12, Jun. 15, 2008, pp. 1285-1287.

Robles, Francisco et al., "Dual Window Method for Processing Spectroscopic OCT Signals with Simultaneous High Spectral and Temporal Resolution," Optical Society of America, 2008, 12 pages.

Keener, Justin D. et al., "Application of Mie Theory to Determine the Structure of Spheroidal Scatterers in Biological Materials," Optics Letters, vol. 32, No. 10, May 15, 2007, pp. 1326-1328.

Chalut, Kevin J. et al., "Application of Mie Theory to Assess Structure of Spheroidal Scattering in Backscattering Geometries," J. Opt. Soc. Am. A, vol. 25, No. 8, Aug. 2008, pp. 1866-1874.

Chalut, Kevin J. et al., "Light Scattering Measurements of Subcellular Structure Provide Noninvasive Early Detection of Chemotherapy-induced Apoptosis," not yet published, 2009, 25 pages.

Chalut, Kevin J., et al., "Label-Free, High-Throughput Measurements of Dynamic Changes in Cell Nuclei Using Angle-Resolved Low Coherence Interferometry," Biophysical Journal, vol. 94, Jun. 2008, pp. 4948-4956.

Giacomelli, Michael G. et al., "Application of the T-matrix Method to Determine the Structure of Spheroidal Cell Nuclei with Angle-resolved Light Scattering," Optics Letters, vol. 33, No. 21, Nov. 1, 2008, pp. 2452-2454.

Wax, Adam, "Studying the Living Cell Using Light Scattering and Low-Coherence Interferometry," Laser Biomedical Research Center, MIT Spectroscopy Laboratory, presented at Case Western Reserve University 2002, Feb. 1, 2002.

Pyhtila, John W. et al., "Polarization Effects on Scatterer Sizing Accuracy Analyzed with Frequency-Domain Angle-Resolved Low-Coherence Interferometry," Applied Optics, vol. 46, No. 10, Apr. 1, 2007.

Pyhtila, John W. et al., "Coherent Light Scattering by in Vitro Cell Arrays Observed with Angle-Resolved Low Coherence Interferometry," SPIE, vol. 5690, 2005.

Wax, Adam et al., "Angular Light Scattering Studies Using Low-Coherence Interferometry," SPIE, vol. 4251, 2001.

Grant Progress Report for "In Vivo Detection of Pre-Cancerous Lesions Using a/LCI", Dec. 2005, pp. 1-9.

Wax, Adam, Proposal submitted to National Institutes of Health for "In Vivo Detection of Pre-Cancerous Lesions Using a/LCI," Nov. 19, 2003, pp. 1-64.

Wax, Adam, "In Vivo Detection of Pre-Cancerous Lesions Using a/LCI," Abstract, printed from Computer Retrieval of Information on Scientific Projects (CRISP), Aug. 1, 2004, 2 pages.

Wax, Adam, "Coherence and Spectroscopy Studies for Biomed Imaging," Abstract, printed from http://www.researchgrantdatabase.com, 2000, 1 page.

Wax, Adam, "Assessing Nuclear Morphology in Thick Tissues Using FLCI," Abstract, printed from http://www.researchgrantdatabase.com, Apr. 14, 2006, 1 page.

(56) References Cited

OTHER PUBLICATIONS

Wax, Adam, "Assessing Deployment of Microbicidal Gels with Label-Free Optical Measurement," Abstract, printed from http://www.researchgrantdatabase.com, Jul. 1, 2007, 2 pages.

Wax, Adam et al., Angle-Resolved Low Coherence Interferometry for Detection of Dysplasia in Barrett's Esophagus, Gastroenterology, published online Jun. 21, 2011, pp. 443-447.e2, vol. 141, issue 2.

Zhu, Y., et al., "Development of angle-resolved low coherence interferometry for clinical detection of dysplasia," Journal of Carcinogenesis, vol. 10, Issue 1, published online Aug. 23, 2011, p. 19.

Wax, Adam et al., "Nuclear morphology measurements with angle-resolved low coherence interferometry for application to cell biology and early cancer detection,"Analytical Cellular Pathology 1, published Aug. 12, 2011, 16 pages.

Drake, Tyler K., et al. "Design and validation of a multiplexed low coherence interferometry instrument for in vivo clinical measurement of microbicide gel thickness distribution," Biomedical Optics Express, Oct. 1, 2011, vol. 2, No. 10, pp. 2850-2858.

Duke University, Japanese Application No. 2012-550195, Notice of Rejection, Jul. 15, 2014.

\* cited by examiner

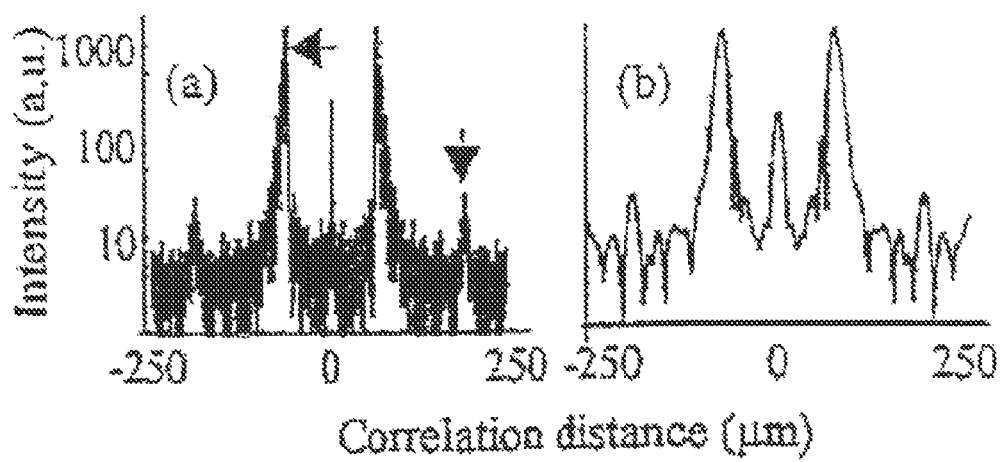
*FIG. 3A*  *FIG. 3B*

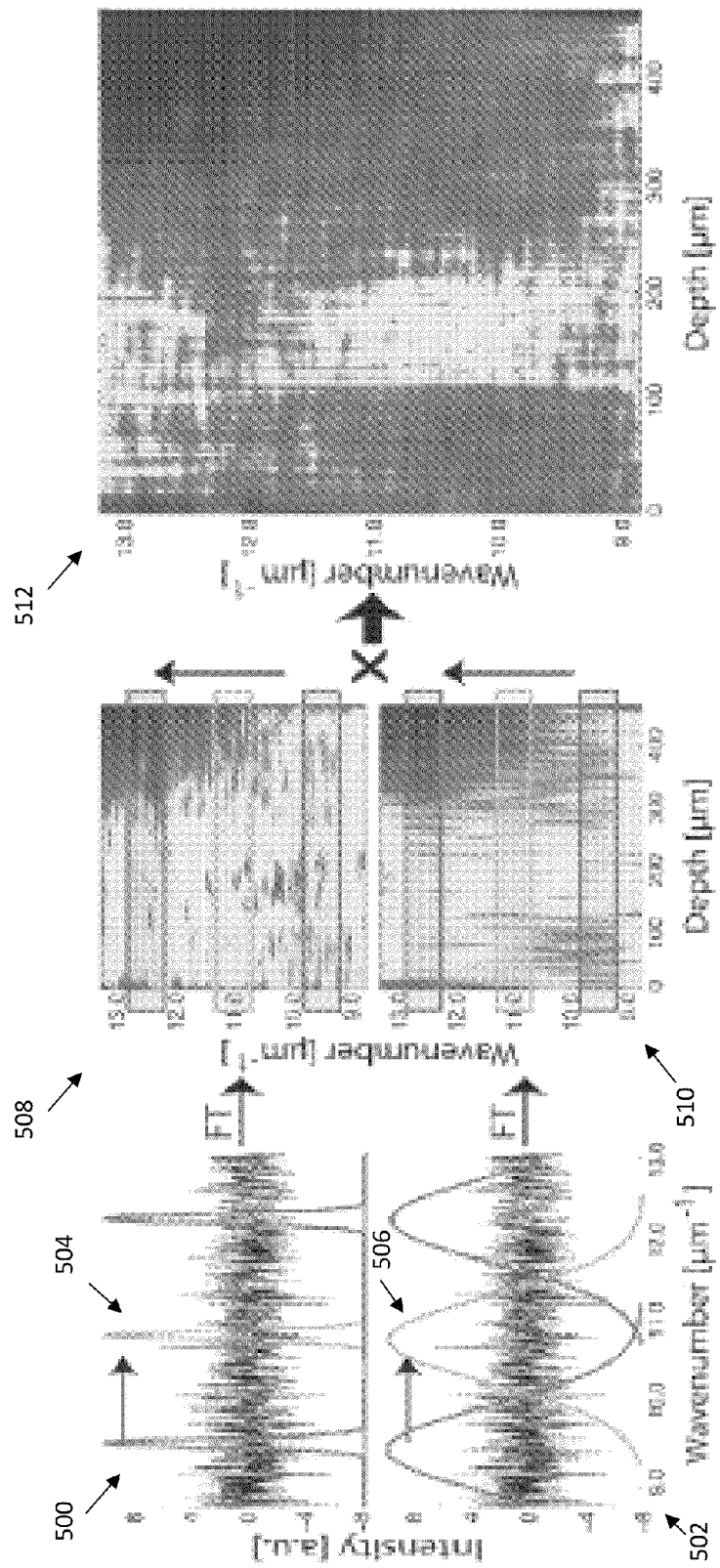

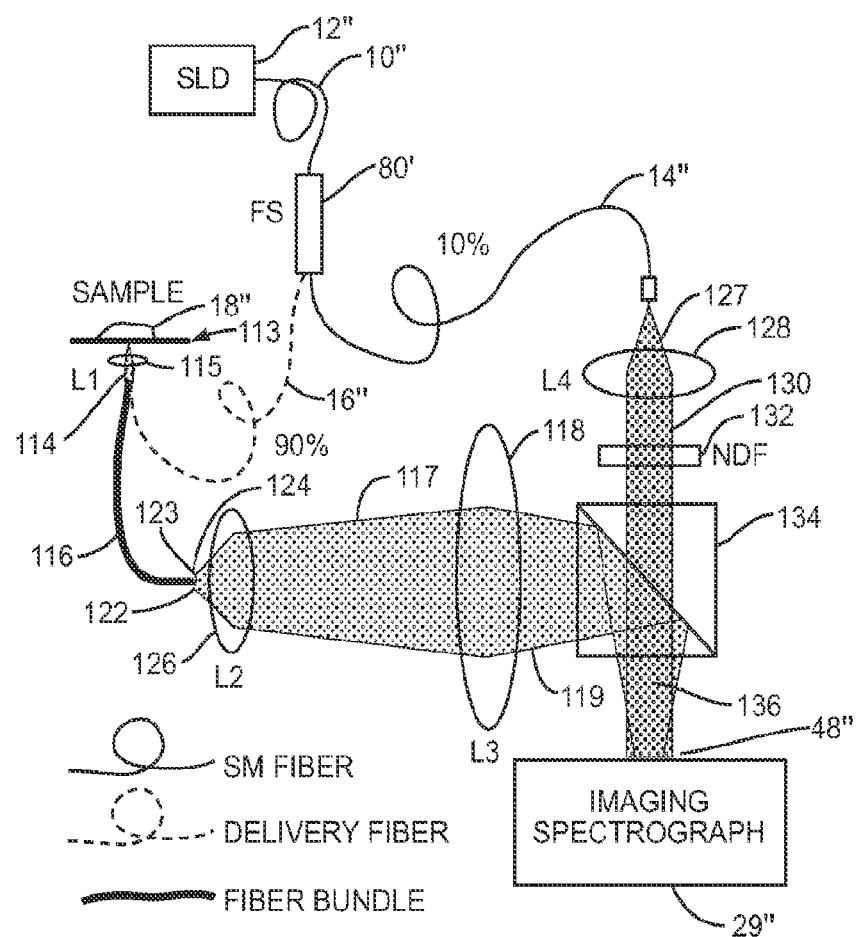
FIG. 15A
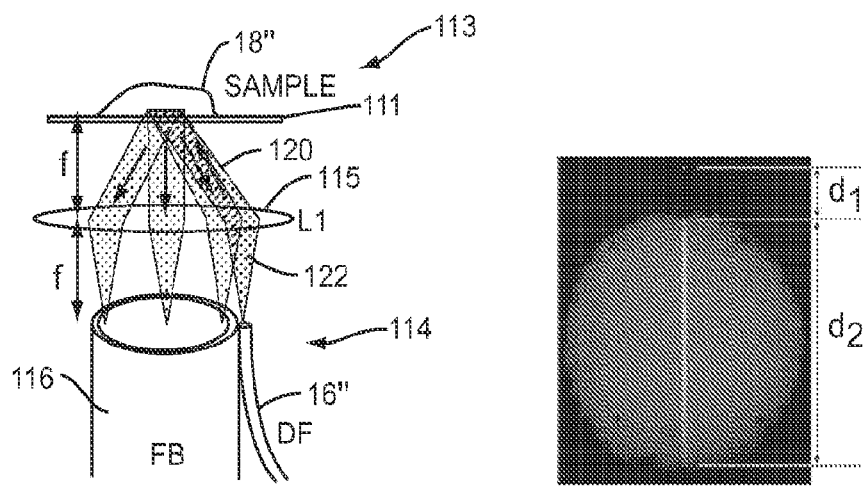
FIG. 15B          FIG. 15C

| | Surface (mean+/−SEM) | Mid (mean+/−SEM) | Low (mean+/−SEM) |
|---|---|---|---|
| Control | 5.88+/−0.20 | 5.15+/−0.05 | 5.25+/−0.05 |
| Week 4 | 5.96 +/−0.18 | 5.91+/−0.15** | 5.84+/−0.16* |
| Week 8 | 6.36 +/−0.21 | 6.02+/−0.18** | 5.97+/−0.18* |
| Week 12 | 5.48 +/−0.33 | 6.49+/−0.49** | 5.95+/−0.47* |

All measurements in μm; $p\text{-values}<10^{-4}$ **; $p\text{-values}<0.05$ *; $N = 10$.

FIG. 39

|  | Proximal LC (mean+/−SEM) | | Distal LC (mean+/−SEM) | |
|---|---|---|---|---|
|  | fLCI [µm] | ACF | fLCI [µm] | ACF |
| Control | 5.15+/−0.05 | 0 | 5.15+/−0.05 | 0 |
| Week 4 | 5.87+/−0.19 | 13.4+/−3.64 | 5.98+/−0.26 | 5.9+/−1.33 |
| Week 8 | 5.88+/−0.27 | 55.1+/−5.60 | 6.14+/−0.24 | 16+/−1.71 |
| Week 12 | 7.23+/−1.21 | 68.6+/−4.74 | 6.10+/−0.39 | 33.3+/−5.95 | all $p\text{-values} < 10^{-4}$ **; $N = 10$.

*FIG. 40*

DUAL WINDOW PROCESSING SCHEMES FOR SPECTROSCOPIC OPTICAL COHERENCE TOMOGRAPHY (OCT) AND FOURIER DOMAIN LOW COHERENCE INTERFEROMETRY

RELATED APPLICATIONS

The present application claims priority to U.S. Provisional Patent Application Ser. No. 61/297,588, filed Jan. 22, 2010, titled "DUAL WINDOW PROCESSING SCHEMES FOR SPECTROSCOPIC OPTICAL COHERENCE TOMOGRAPHY (OCT) AND FOURIER DOMAIN LOW COHERENCE INTERFEROMETRY," which is incorporated herein by reference in its entirety.

The present application is related to U.S. Pat. No. 7,102,758 titled "FOURIER DOMAIN LOW-COHERENCE INTERFEROMETRY FOR LIGHT SCATTERING SPECTROSCOPY APPARATUS AND METHOD," which is incorporated herein by reference in its entirety.

The present application is also related to U.S. patent Reissue application Ser. No. 12/205,248 titled "FOURIER DOMAIN LOW-COHERENCE INTERFEROMETRY FOR LIGHT SCATTERING SPECTROSCOPY APPARATUS AND METHOD," which is incorporated herein by reference in its entirety.

The present application is also related to U.S. Pat. No. 7,595,889 titled "SYSTEMS AND METHODS FOR ENDOSCOPIC ANGLE-RESOLVED LOW COHERENCE INTERFEROMETRY," which is incorporated herein by reference in its entirety.

The present application is also related to U.S. patent application Ser. No. 12/538,309 titled "SYSTEMS AND METHODS FOR ENDOSCOPIC ANGLE-RESOLVED LOW COHERENCE INTERFEROMETRY," which is incorporated herein by reference in its entirety.

The present application is also related to U.S. patent application Ser. No. 12/210,620 titled "APPARATUSES, SYSTEMS AND METHODS FOR LOW-COHERENCE INTERFEROMETRY (LCI)," which is incorporated herein by reference in its entirety.

The present application is also related to U.S. patent application Ser. No. 11/780,879 titled "PROTECTIVE PROBE TIP, PARTICULARLY FOR USE ON FIBER-OPTIC PROBE USED IN AN ENDOSCOPIC APPLICATION," which is incorporated herein by reference in its entirety.

The present application is also related to U.S. patent application Ser. No. 12/350,689 titled "SYSTEMS AND METHODS FOR TISSUE EXAMINATION, DIAGNOSTIC, TREATMENT AND/OR MONITORING," which is incorporated herein by reference in its entirety.

STATEMENT REGARDING FEDERALLY SPONSORED RESEARCH OR DEVELOPMENT

This invention was supported by the National Institute of Health, Grant No. R121-CA-120128, and the National Science Foundation, Grant No. BES-03-48204. The United States Government has certain rights in the invention.

APPENDIX

The Appendix attached hereto the present application lists references that are referenced in this application by corresponding number in the Appendix as indicated by brackets [ ].

BACKGROUND

1. Field of the Disclosure

The technology of the disclosure relates to apparatuses and methods for obtaining depth-resolved spectra using Optical Coherence Tomography (OCT) systems and methods, as well as Fourier domain low-coherence interferometry (f/LCI) and Fourier domain angle-resolved low coherence interferometry (fa/LCI) systems and methods.

2. Technical Background

Accurately measuring small objects or other physical phenomena is a goal that is pursued in many diverse fields of scientific endeavor. For example, in the study of cellular biology and cellular structures, examining the structural features of cells is essential for many clinical and laboratory studies. The most common tool used in the examination for the study of cells has been the microscope. Although microscope examination has led to great advances in understanding cells and their structure, it is inherently limited by the artifacts of preparation. The characteristics of the cells can only been seen at one moment in time with their structure features altered because of the addition of chemicals. Further, invasion is necessary to obtain the cell sample for examination.

Thus, light scattering spectrography (LSS) was developed to allow for in vivo examination applications, including cells. The LSS technique examines variations in the elastic scattering properties of cell organelles to infer their sizes and other dimensional information. In order to measure cellular features in tissues and other cellular structures, it is necessary to distinguish the singly scattered light from diffuse light, which has been multiply scattered and no longer carries easily accessible information about the scattering objects. This distinction or differentiation can be accomplished in several ways, such as the application of a polarization grating, by restricting or limiting studies and analysis to weakly scattering samples, or by using modeling to remove the diffuse component(s).

LSS has received much attention recently as a means for probing cellular morphology and the diagnosing of dysplasia. The disclosures of the following references are incorporated by reference in their entirety: Backman, V., V. Gopal, M. Kalashnikov, K. Badizadegan, R. Gurjar, A. Wax, I. Georgakoudi, M. Mueller, C. W. Boone, R. R. Dasari, and M. S. Feld, IEEE J. Sel. Top. Quantum Electron., 7(6): p. 887 893 (2001); Mourant, J. R., M. Canpolat, C. Brocker, O. Esponda-Ramos, T. M. Johnson, A. Matanock, K. Stetter, and J. P. Freyer, J. Biomed. Opt., 5(2): p. 131 137 (2000); Wax, A., C. Yang, V. Backman, K. Badizadegan, C. W. Boone, R. R. Dasari, and M. S. Feld, Biophysical Journal, 82: p. 2256 2264 (2002); Georgakoudi, I., E. E. Sheets, M. G. Muller, V. Backman, C. P. Crum, K. Badizadegan, R. R. Dasari, and M. S. Feld, Am J Obstet Gynecol, 186: p. 374 382 (2002); Backman, V., M. B. Wallace, L. T. Perelman, J. T. Arendt, R. Gurjar, M. G. Muller, Q. Zhang, G. Zonios, E. Kline, T. McGillican, S. Shapshay, T. Valdez, K. Badizadegan, J. M. Crawford, M. Fitzmaurice, S. Kabani, H. S. Levin, M. Seiler, R. R. Dasari, I. Itzkan, J. Van Dam, and M. S. Feld, Nature, 406(6791): p. 35 36 (2000); Wax, A., C. Yang, M. Mueller, R. Nines, C. W. Boone, V. E. Steele, G. D. Stoner, R. R. Dasari, and M. S. Feld, Cancer Res, (accepted for publication).

As an alternative approach for selectively detecting singly scattered light from sub-surface sites, low-coherence interferometry (LCI) has also been explored as a method of LSS. LCI utilizes a light source with low temporal coherence, such as broadband white light source for example. Interference is only achieved when the path length delays of the interferometer are matched with the coherence time of the light source.

The axial resolution of the system is determined by the coherent length of the light source and is typically in the micrometer range suitable for the examination of tissue samples. Experimental results have shown that using a broadband light source and its second harmonic allows the recovery of information about elastic scattering using LCI. LCI has used time depth scans by moving the sample with respect to a reference arm directing the light source onto the sample to receive scattering information from a particular point on the sample. Thus, scan times were on the order of 5-30 minutes in order to completely scan the sample.

More recently, angle-resolved LCI (a/LCI) has demonstrated the capability of obtaining structural information by examining the angular distribution of scattered light from the sample or object under examination. The a/LCI technique has been successfully applied to measuring cellular morphology and to diagnosing intraepithelial neoplasia in an animal model of carcinogenesis. a/LCI is another means to obtain sub-surface structural information regarding the size of a cell. Light is split into a reference and sample beam, wherein the sample beam is projected onto the sample at different angles to examine the angular distribution of scattered light. The a/LCI technique combines the ability of (LCI) to detect singly scattered light from sub-surface sites with the capability of light scattering methods to obtain structural information with sub-wavelength precision and accuracy to construct depth-resolved tomographic images. Structural information is determined by examining the angular distribution of the back-scattered light using a single broadband light source is mixed with a reference field with an angle of propagation. The size distribution of the cell is determined by comparing the osciallary part of the measured angular distributions to predictions of Mie theory. Such a system is described in *Cellular Organization and Substructure Measured Using Angle-Resolved Low-Coherence Inteferometry*, Biophysical Journal, 82, April 2002, 2256-2265, incorporated herein by reference in its entirety.

The a/LCI technique has been successfully applied to measuring cellular morphology and to diagnosing intraepithelial neoplasia in an animal model of carcinogenesis. Such a system is described in *Determining nuclear morphology using an improved angle-resolved low coherence interferometry system* in Optics Express, 2003, 11(25): p. 3473-3484, incorporated herein by reference in its entirety. The a/LCI method of obtaining structural information about a sample has been successfully applied to measuring cellular morphology in tissues and in vitro as well as diagnosing intraepithelial neoplasia and assessing the efficacy of chemopreventive agents in an animal model of carcinogenesis. a/LCI has been used to prospectively grade tissue samples without tissue processing, demonstrating the potential of the technique as a biomedical diagnostic.

Another technique is optical coherence tomography (OCT). OCT has been established as an excellent technique for cross-sectional imaging of biological samples with high resolution, speed, and sensitivity [1]. In recent years, several specialized extensions of OCT have been developed in order to gain functional information about probed samples [2-5]. One such extension, which seeks to analyze depth-resolved spectroscopic information about experimental samples, is known as spectroscopic OCT (SOCT) when applied as an imaging technique [2, 6] and Fourier domain low coherence interferometry (fLCI) when applied as an analysis method [7, 8]. Because the spectral scattering and absorption properties of an experimental sample vary depending on its molecular makeup, SOCT obtains increased contrast and functional information by spatially mapping spectral characteristics onto coherence gated images.

In order to generate depth resolved spectroscopic information from data collected in a single domain, SOCT typically employs a short time Fourier transform (STFT) or a continuous wavelet transform (CWT). The resulting depth-wavelength distributions are analogous to time-frequency distributions (TFDs) which have been analyzed extensively in the signal processing literature [9, 10], but only recently analyzed in the context of SOCT [11, 12]. Graf and Wax used the Wigner TFD from Cohen's class of functions [13] to show that temporal coherence information contained in the Wigner TFD cross-terms can be utilized to gain structural knowledge of samples via SOCT signals [12]. However, TFDs generated by the STFT are severely limited by the relationship between time and frequency which results in an inherent tradeoff between time (depth) resolution and frequency (wavelength) resolution.

Work in the fields of signal processing and quantum physics have paved the way for a new SOCT processing technique that ameliorates the detrimental effects of the time-frequency resolution tradeoff. Thomson, for example, developed a method particularly well suited for stationary Gaussian signals using orthogonal windows as means for estimating weighted averages for spectral approximations to achieve high-resolution spectral information [9]. Later, Bayram and Baraniuk expanded on Thomson's method by implementing two Hermite-function-based windows to provide a robust analysis of the time-varying spectrum of non-stationary signals, which are pertinent to fields such as radar, sonar, acoustics, biology, and geophysics [10]. More recently, Lee et al [14] showed that using multiple windows simultaneously can avoid a similar resolution tradeoff in measurement of the position and momentum of a light field.

Current methods for analysis of spectroscopic optical coherence tomography (SOCT) signals suffer from an inherent tradeoff between time (depth) and frequency (wavelength) resolution. As higher frequency resolution is sought, there is a concomitant loss of depth resolution.

SUMMARY OF THE DETAILED DESCRIPTION

Embodiments disclosed in the detailed description include multiple window (MW) methods and apparatuses for reconstructing time-frequency distributions (TFDs) that apply two or more windows (e.g., orthogonal Gaussian) can be used to independently determine the information, including spectral information, and temporal resolution such that it is possible to simultaneously obtain high resolution information within a sample.

In one embodiment, the MW technique involves dual windows (DW). For example, in one embodiment, the information may include high resolution spectral information and temporal depth resolution information. The disclosed MW and DW techniques can yield TFDs that contain localized reconstructed fields without the loss of resolution, such as spectral or temporal resolution.

In one embodiment, a method of obtaining depth-resolved spectra of a sample for determining scattering and absorption characteristics within the sample is provided. The method comprises emitting a beam onto a splitter, wherein the splitter splits light from the beam to produce a reference beam, and an input beam to the sample. The method also comprises cross-correlating the reference beam with a sample beam returned from the sample as a result of the input beam by mixing the reference beam and the returned sample beam from the sample to yield a cross-correlated profile having optical, depth-resolved information about the returned sample beam. The method also comprises generating a spectroscopic depth-resolved profile that includes optical properties about the sample by: providing first one or more spectroscopic windows of the cross-correlated profile, each of the first one or more spectroscopic windows having a first width at a given center wavelength to obtain optical information about the sample for each given center wavelength; applying a Fourier transform to the optical information about the sample as a function of wavelength to recover high resolution optical information about the sample at each given center wavelength simultaneously; providing second one or more spectroscopic windows of the cross-correlated profile, each of the second one or more spectroscopic windows having a second width greater than the first width at a given center wavelength to obtain absorption information about the sample for each given center wavelength; applying a Fourier transform to the absorption information about the sample as a function of depth to recover high resolution depth information about the sample at each given center wavelength simultaneously; and co-registering the high resolution optical information and the high resolution depth information about the sample to yield a single high resolution spectroscopic optical-resolved, depth-resolved profile about the sample.

In another embodiment, an apparatus for obtaining depth-resolved information of a sample in order to determine the scattering and absorption characteristics within the sample is provided. The apparatus comprises a receiver adapted to receive a reference beam and a returned sample beam containing light returned from a sample in response to the sample receiving a sample beam, wherein the receiver is further adapted to cross-correlate the reference beam with the returned sample beam. The apparatus also comprises a detector adapted to detect the cross-correlated reference beam and the returned sample beam to yield a cross-correlated profile having depth-resolved information about the returned sample beam. The apparatus also comprises a processor unit. The processor unit is adapted to generate a spectroscopic depth-resolved profile about the sample that includes optical properties by: providing first one or more spectroscopic windows of the cross-correlated profile, each of the first one or more spectroscopic windows having a first width at a given center wavelength to obtain optical information about the sample for each given center wavelength; applying a Fourier transform to the optical information about the sample as a function of wavelength to recover high resolution optical information about the sample at each given center wavelength simultaneously; providing second one or more spectroscopic windows of the cross-correlated profile, each of the second one or more spectroscopic windows having a second width greater than the first width at a given center wavelength to obtain absorption information about the sample for each given center wavelength; applying a Fourier transform to the absorption information about the sample as a function of depth to recover high resolution depth information about the sample at each given center wavelength simultaneously; and co-registering the high resolution optical information and the high resolution depth information about the sample to yield a single high resolution spectroscopic optical-resolved, depth-resolved profile about the sample.

The effectiveness of the dual window apparatuses and methods are demonstrated in simulations and in processing of measured Optical Coherence Tomography (OCT) signals that contain fields which vary in time and frequency. The exemplary DW techniques described herein can yield TFDs that maintain high spectral and temporal resolution and are free or substantially free from the artifacts and limitations commonly observed with other processing methods. The DW technique can be applied to detect modulation of OCT signals due to scattering or absorption; thus posing a well-conditioned problem for the DW technique. The exemplary dual window techniques described herein allow the reconstruction of the Wigner TFD of an SOCT signal using two orthogonal windows which independently determine spectral and temporal resolution, avoiding the time-frequency resolution tradeoff that limits current SOCT signal processing. Simulations and experimental results from scattering and absorption phantoms are presented to justify the capabilities of the approach.

Additional features and advantages will be set forth in the detailed description which follows, and in part will be readily apparent to those skilled in the art from that description or recognized by practicing the embodiments as described herein, including the detailed description that follows, the claims, as well as the appended drawings.

It is to be understood that both the foregoing general description and the following detailed description present embodiments, and are intended to provide an overview or framework for understanding the nature and character of the disclosure. The accompanying drawings are included to provide a further understanding, and are incorporated into and constitute a part of this specification. The drawings illustrate various embodiments, and together with the description serve to explain the principles and operation of the concepts disclosed.

BRIEF DESCRIPTION OF THE FIGURES

FIGS. 3A and 3B are diagrams illustrating an exemplary axial spatial cross-correlation function for a coverslip sample;

FIG. 5A illustrates diagrams of exemplary spectra obtained from a sample with first narrower windows applied to the interference term before performing the Fourier transform operation to obtain higher resolution spectral information about the sample, and second wider windows separately applied to the interference term before performing the Fourier transform operation to obtain higher resolution depth information about the sample;

FIG. 5B illustrates diagrams of exemplary higher resolution depth-resolved spectral information profiles including higher resolution spectral information and higher resolution depth information, respectively, about the sample as a function of wave number and depth after performing Fourier transforms separately using two different sized windows to interference terms in FIG. 5A;

FIG. 5C is an exemplary diagram of combined higher resolution spectral and depth information depth-resolved spectral information profiles in FIG. 5B combined together to provide a single depth-resolved spectral information profile regarding the sample that includes higher resolution spectral and depth information;

FIG. 15A is an illustration of an alternative fiber-optic fa/LCI system that may be employed with the embodiments described herein;

FIG. 15B is an illustration of sample illumination and scattered light collection with distal end of probe in the fa/LCI system illustrated in FIG. 15B;

FIG. 15C is an illustration of an image of the illuminated distal end of probe of the fa/LCI system illustrated in FIG. 15A;

FIG. 18A shows an exemplary TFD of simulation 2 generated by the dual window (DW) processing method;

FIG. 39 is a table containing exemplary measured cell nuclear diameters by depth sections (measurements in µm; $p\text{-values} < 10\text{-}4^{**}$; $p\text{-values} < 0.05^{*}$; $N=10$);

FIG. 40 is a table containing exemplary measured cell nuclear diameters (fLCI measurement) and number of ACF by length segments;

FIG. 41C) plots the measured cell nuclear diameter as a function of the number of ACF; for clarity, the time of measurement is noted next to each point (wk=week)

DETAILED DESCRIPTION

Figure 1A:
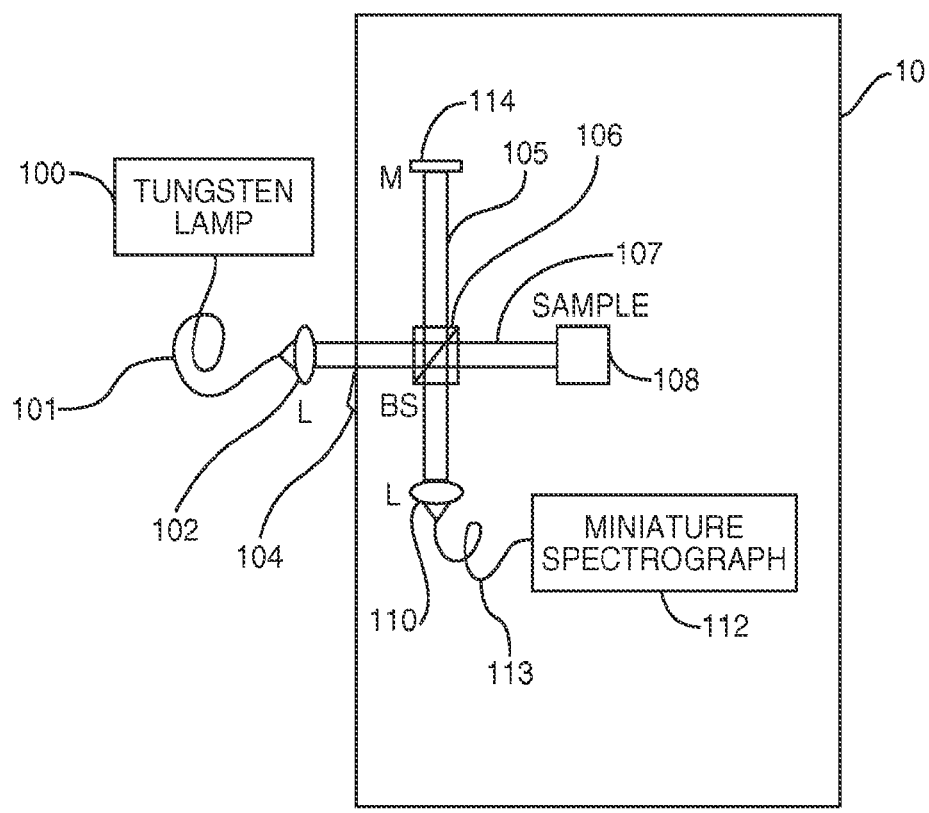
FIG. 1A is a diagram of an exemplary embodiment of an fLCI system.

Reference will now be made in detail to the embodiments, examples of which are illustrated in the accompanying drawings, in which some, but not all embodiments are shown. Indeed, the concepts may be embodied in many different forms and should not be construed as limiting herein; rather, these embodiments are provided so that this disclosure will satisfy applicable legal requirements. Whenever possible, like reference numbers will be used to refer to like components or parts.

Embodiments disclosed in the detailed description include multiple window (MW) methods and apparatuses for reconstructing time-frequency distributions (TFDs) that apply two or more windows (e.g., orthogonal Gaussian) can be used to independently determine the information, including spectral information, and temporal resolution such that it is possible to simultaneously obtain high resolution information within a sample.

In one embodiment, the MW technique involves dual windows (DW). For example, in one embodiment, the information may include high resolution spectral information and temporal depth resolution information. The disclosed MW and DW techniques can yield TFDs that contain localized reconstructed fields without the loss of resolution, such as spectral or temporal resolution.

In one embodiment, a method of obtaining depth-resolved spectra of a sample for determining scattering and absorption characteristics within the sample is provided. The method comprises emitting a beam onto a splitter, wherein the splitter splits light from the beam to produce a reference beam, and an input beam to the sample. The method also comprises cross-correlating the reference beam with a sample beam returned from the sample as a result of the input beam by mixing the reference beam and the returned sample beam from the sample to yield a cross-correlated profile having optical, depth-resolved information about the returned sample beam. The method also comprises generating a spectroscopic depth-resolved profile that includes optical properties about the sample by: providing first one or more spectroscopic windows of the cross-correlated profile, each of the first one or more spectroscopic windows having a first width at a given center wavelength to obtain optical information about the sample for each given center wavelength; applying a Fourier transform to the optical information about the sample as a function of wavelength to recover high resolution optical information about the sample at each given center wavelength simultaneously; providing second one or more spectroscopic windows of the cross-correlated profile, each of the second one or more spectroscopic windows having a second width greater than the first width at a given center wavelength to obtain absorption information about the sample for each given center wavelength; applying a Fourier transform to the absorption information about the sample as a function of depth to recover high resolution depth information about the sample at each given center wavelength simultaneously; and co-registering the high resolution optical information and the high resolution depth information about the sample to yield a single high resolution spectroscopic optical-resolved, depth-resolved profile about the sample.

The dual window apparatuses and methods were designed in one embodiment to be used to recover simultaneous spectral and depth information from a broadband OCT or LCI signal. This approach could also be applicable to detecting multispectral information for angle-resolved low coherence interferometry (a/LCI). In a/LCI, scattered light is detected as a function of angle to determine the structure of scattering objects. As an example, an a/LCI light source may have a bandwidth of 20-40 nm to enable cellular scale depth resolution (30 microns). However, if a light source with a broader bandwidth were used, the dual window apparatuses and methods could be applied to provide simultaneous depth and spectral information in addition to the angle-resolved scattering. The combination of scattering data at a multitude of wavelengths and scattering angles could enable more precise data analysis and lead to improved determinations of structural information. In this scheme, multiple broadband sources could be used or a single source with a large bandwidth. The key determinant here is that there is spectrally resolved data is available. While time domain a/LCI can be Fourier transformed to yield spectral data, the frequency domain data acquisition modalities naturally lend themselves to this type of analysis. Specifically, Fourier domain a/LCI, where spectral data are acquired with a spectrometer, and swept source a/LCI, where data are acquired by sweeping the frequency of a narrowband laser in time, are both well suited for implementation of multispectral a/LCI using the dual window approach.

Before discussing the exemplary DW techniques, exemplary systems that may be employed to capture depth-resolved spectral information regarding a sample using LCI that may then use the exemplary DW techniques described herein to obtain high resolution depth-resolved spectral information about the sample are first discussed below. For example, the DW techniques described herein may also be used in f/LCI systems. Below is a description of one embodiment of an f/LCI system.

Exemplary f/LCI System

The contents of the following references are incorporated by reference in their entirety: Wojtkowski, M., A. Kowalczyk, R. Leitgeb, and A. F. Fercher, Opt. Lett., 27(16): p. 1415 1417 (2002); Wojtkowski, M., R. Leitgeb, A. Kowalczyk, T. Bajraszewski, and A. F. Fercher, J. Biomed. Opt., 7(3): p. 457 463 (2002); Leitgeb, R., M. Wojtkowski, A. Kowalczyk, C. K. Hitzenberger, M. Sticker, and A. F. Fercher, Opt. Lett., 25(11): p. 820 822 (2000).

In general, spectral radar makes use of techniques where depth-resolved structural information is recovered by applying a Fourier transform to the spectrum of two mixed fields. In fLCI, the aforementioned approach used in spectral radar applications is extended to recover not only depth-resolved structure, but also to obtain spectroscopic information about scattered light as a function of depth. The capabilities of fLCI enable extracting the size of polystyrene beads in a sub-surface layer based on their light scattering spectrum. The apparatus and method according to exemplary embodiments described herein can be applied to many different areas. One such area of application is to recover nuclear morphology of sub-surface cell layers.

One exemplary embodiment of the fLCI scheme is shown in FIG. 1A. White light from a Tungsten light source 100 (e.g. 6.5 W, Ocean Optics™) is coupled into a multimode fiber 101 (e.g. 200 μm core diameter). The output of the fiber 101 is collimated by an achromatic lens 102 to produce a beam 104 (e.g. a pencil beam 5 mm in diameter). The beam 104 is then forwarded to an fLCI system 10.

This illumination scheme achieves Kohler illumination in that the fiber acts as a field stop, resulting in the proper alignment of incident or illuminating light and thereby achieving critical illumination of the sample. In the fLCI system 10, the white light beam is split by the beamsplitter 106 (BS) into a reference beam 105 and an input beam 107 to the sample 108. The light returned by the sample 108, or optical information, is recombined at the BS 106 with light reflected by the reference mirror 114 (M). This optical information returned by the sample 108 may include scattering or reflectance properties or information In one embodiment, light scattering by the sample 108 could be recombined at the BS 106 with the light reflected by the reference mirror 114 to generate an interference term having depth-resolved spectral information or properties about the sample 108. Alternatively, the light reflected by the sample 108 could be recombined at the BS 106 with the light reflected by the reference mirror 114 to generate an interference term having depth-resolved optical information or properties about the sample 108. The light returned by the sample 108 may also contain absorption information or properties about the sample 108 in addition to scattering or reflectance properties or information.

The reference beam 105 in conjunction with the reference mirror 114 forms a portion of a reference arm that receives a first reference light and outputs a second reference light. The input beam 107 and the sample 108 form a portion of a sample arm that receives a first sample light and outputs a second sample light.

Those skilled in the art will appreciate that the light beam can be split into a plurality of reference beams and input beams (e.g. N reference beams and N input beams) without departing from the spirit and scope of the embodiments described herein. Further, the splitting of the beams may be accomplished with a beamsplitter or a fiber splitter in the case of an optical fiber implementation of an exemplary embodiment.

In the exemplary embodiment shown in FIG. 1A, the combined beam is coupled into a multimode fiber 113 by an aspheric lens 110. Again, other coupling mechanisms or lens types and configurations may be used without departing from the spirit and scope of the present application. The output of the fiber coincides with the input slit of a miniature spectrograph 112 (e.g. USB2000, Ocean Optics™), where the light is spectrally dispersed and detected.

The detected signal is linearly related to the intensity as a function of wavelength $I(\lambda)$, which can be related to the signal and reference fields ($E_s$, $E_r$) as:

$$<I(\lambda)>=<|E_s(\lambda)|^2>+<|E_r(\lambda)|^2>+ \\ 2Re<E_s(\lambda)E^*_r(\lambda)>\cos\Phi \quad (1)$$

where $\Phi$ is the phase difference between the two fields and $<\ldots>$ denotes an ensemble average.

The interference term is extracted by measuring the intensity of the signal and reference beams independently and subtracting them from the total intensity.

The axial spatial cross-correlation function, $\Gamma_{SR}(z)$ between the sample and reference fields is obtained by resealing the wavelength spectrum into a wavenumber ($k=2\pi/\lambda$) spectrum then Fourier transforming:

$$\Gamma_{SR}(z) = \int dk e^{ikz} <E_s(k)E^*_r(k)> \cos \Phi. \quad (2)$$

This term is labeled as an axial spatial cross-correlation as it is related to the temporal or longitudinal coherence of the two fields.

Figure 1B:
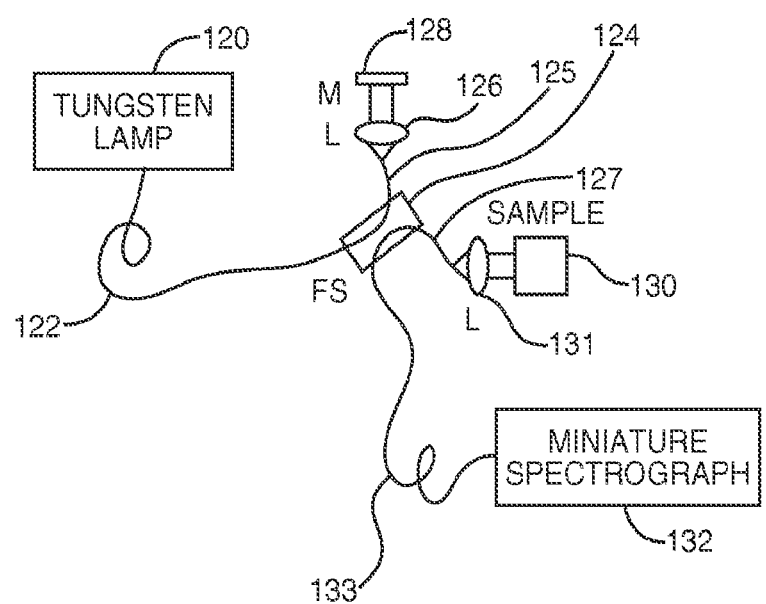
FIG. 1B is a diagram of another exemplary embodiment of an fLCI system using fiber optic coupling.

Another exemplary embodiment of an fLCI scheme is shown in FIG. 1B. In this exemplary embodiment, fiber optic cable is used to connect the various components. Those skilled in the art will appreciate that other optical coupling mechanisms, or combinations thereof, may be used to connect the components without departing from the spirit and scope of the present application.

In FIG. 1B, white light from a Tungsten light source 120 is coupled into a multimode fiber 122 and the white light beam in the multimode fiber is split by the fiber splitter (FS) 124 into a reference fiber 125 and a sample fiber 127 to the sample 130. The fiber splitter 124 is used to split light from one optical fiber source into multiple sources.

The reference light in reference fiber 125, in conjunction with a lens 126 (preferably an aspheric lens) and the reference mirror 128, forms a portion of a reference arm that receives a first reference light and outputs a second reference light. Specifically, reference light in reference fiber 125 is directed to the reference mirror 128 by lens 126, and the reference light reflected by the reference mirror 128 (second reference light) is coupled back into the reference fiber 125 with lens 126. The sample light in sample fiber 127 and the sample 130 form a portion of a sample arm that receives a first sample light and outputs a second sample light. Specifically, sample light in sample fiber 127 is directed to the sample 130 by lens 131 (preferably as aspheric lens), and at least a portion of the sample light scattered by the sample 130 is coupled into the sample fiber 127 by lens 131. In the exemplary embodiment shown in FIG. 1B, the sample 130 is preferably spaced from lens 131 by a distance approximately equal to the focal length of lens 131.

At least a portion of the reflected reference light in reference fiber 125 and at least a portion of the scattered sample light on sample fiber 127 are coupled into a detector fiber 133 by the FS 124. The detector fiber 133 may be placed to collect light scattered from the sample 130 as illustrated, or alternatively to collect light reflected from the sample 130.

The output of detector fiber 133 coincides with the input of a miniature spectrograph 132, where the light is spectrally dispersed and detected.

Figure 2A:
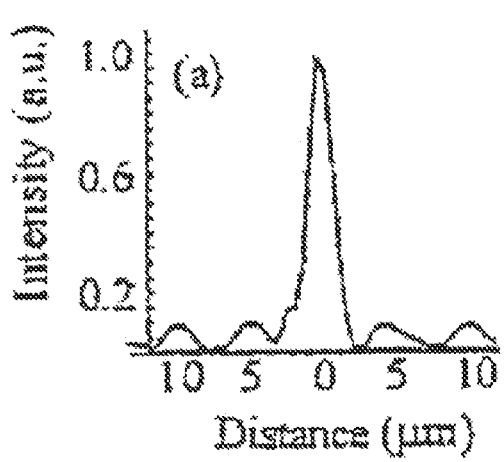
FIGS. 2A and 2B are diagrams illustrating exemplary properties of a white light source.
Figure 2B:
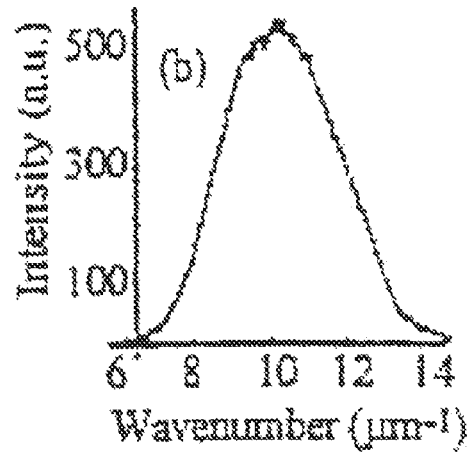

FIGS. 2A and 2B illustrate some of the properties of a white light source. FIG. 2A illustrates an autocorrelation function showing a coherence length ($l_C=1.2$ μm). FIG. 2A shows the cross-correlation between the signal and reference fields when the sample is a mirror, and this mirror is identical to the reference mirror (M). In this exemplary scenario, the fields are identical and the autocorrelation is given by the transform of the incident field spectrum, modeled as a Gaussian spectrum with center wavenumber $k_o=10.3$ μm$^{-1}$ and l/e width $\Delta k_{l/e}=2.04$ μm$^{-1}$ (FIG. 2B).

FIG. 2B shows an exemplary spectrum of light source that can be used in accordance with the embodiments described herein.

From this autocorrelation, the coherence length of the field, $l_C=1.21$ μm is determined. This is slightly larger than the calculated width of $l_c=2/\Delta k_{l/e}=0.98$ μm, with any discrepancy most likely attributed to uncompensated dispersion effects. Note that rescaling the field into wavenumber space is a nonlinear process which can skew the spectrum if not properly executed [13].

In data processing, a fitting algorithm is applied (e.g. a cubic spline fit) to the rescaled wavenumber spectrum and then resampled (e.g. resample with even spacing). The resampled spectrum is then Fourier transformed to yield the spatial correlation of the sample. Those skilled in the art will appreciate that other frequency based algorithms or combinations of algorithms can be used in place of the Fourier transform to yield spatial correlation. One example of a software tool that can be used to accomplish this processing in real time or near real time is to use LabView™ software.

In one exemplary embodiment, the sample consists of a glass coverslip (e.g., thickness, d~200 μm) with polystyrene beads which have been dried from suspension onto the back surface (1.55 μm mean diameter, 3% variance). Thus, the field scattered by the sample can be expressed as:

$$E_s(k) = E_{front}(k)e^{ik\delta_z} + E_{back}(k)e^{ik(\delta_z + nd)} \quad (3)$$

In equation 3, $E_{front}$ and $E_{back}$ denote the field scattered by the front and back surfaces of the coverslip, and $\delta z$ is the difference between the path length of the reference beam and that of the light reflected from the front surface and n the index of refraction of the glass. The effect of the microspheres will appear in the $E_{back}$ term as the beads are small and attached closely to the back surface. Upon substituting equation 3 into equation 2, a two peak distribution with the width of the peaks given by the coherence length of the source is obtained.

In order to obtain spectroscopic information, a Gaussian window is applied to the interference term before performing the Fourier transform operation. Those skilled in the art will appreciate that other probabilistic windowing methodologies may be applied without departing from the spirit and scope of the embodiments described herein. This makes it possible to recover spectral information about light scattered at a particular depth.

The windowed interference term takes the form:

$$<E_s(k)E^*_r(k)>\exp[-((k-k_w)/\Delta k_w)^2]. \quad (4)$$

The proper sizing of a windowed interference term can facilitate the processing operation. For example, by selecting a relatively narrow window ($\Delta k_w$ small) compared to the features of $E_s$ and $E_k$, it is effectively obtained $<E_s(kw)E^*r(kw)>$. In processing the data below, $\Delta k_w=0.12$ μm$^{-1}$ is used, which degrades the coherence length by a factor of 16.7. This exemplary window setting enables the scattering at 50 different wavenumbers over the 6 μm$^{-1}$ span of usable spectrum. In this example, a single Gaussian window is applied to the interference term before performing the Fourier transform. However, as will be discussed in more detail below, two windows may be applied to the interference term.

In FIGS. 3A and 3B, an axial spatial cross-correlation function for a coverslip sample is shown according to one embodiment. FIGS. 3A and 3B shows the depth resolved cross-correlation profiles of the coverslip sample before and after the processing operations. In FIG. 3A, a high resolution scan with arrows indicating a peak corresponding to each glass surface is shown. In FIG. 3B, a low resolution scan is obtained from the scan in FIG. 3A is shown by using a Gaussian window.

Note that the correlation function is symmetric about z=0, resulting in a superposed mirror image of the scan. Since these are represented as cross-correlation functions, the plots are symmetric about z=0. Thus the front surface reflection for z>0 is paired with the back surface reflection for z<0, and vice versa.

In FIG. 3A, the reflection from the coverslip introduces dispersion relative to the reflection from the reference arm, generating multiple peaks in the profile. When the spectroscopic window is applied, only a single peak is seen for each surface, however several dropouts appear due to aliasing of the signal.

To obtain the spectrum of the scattered light, the Gaussian window is repeatedly applied where the center wavenumber is increased by $0.12\ \mu m^{-1}$ between successive applications. As mentioned above, $\Delta k_w = 0.12\ \mu m^{-1}$ is used to degrade the coherence length by a factor of 16.7. This results in the generation of a spectroscopic depth-resolved profile.

Figures 4A, 4B:
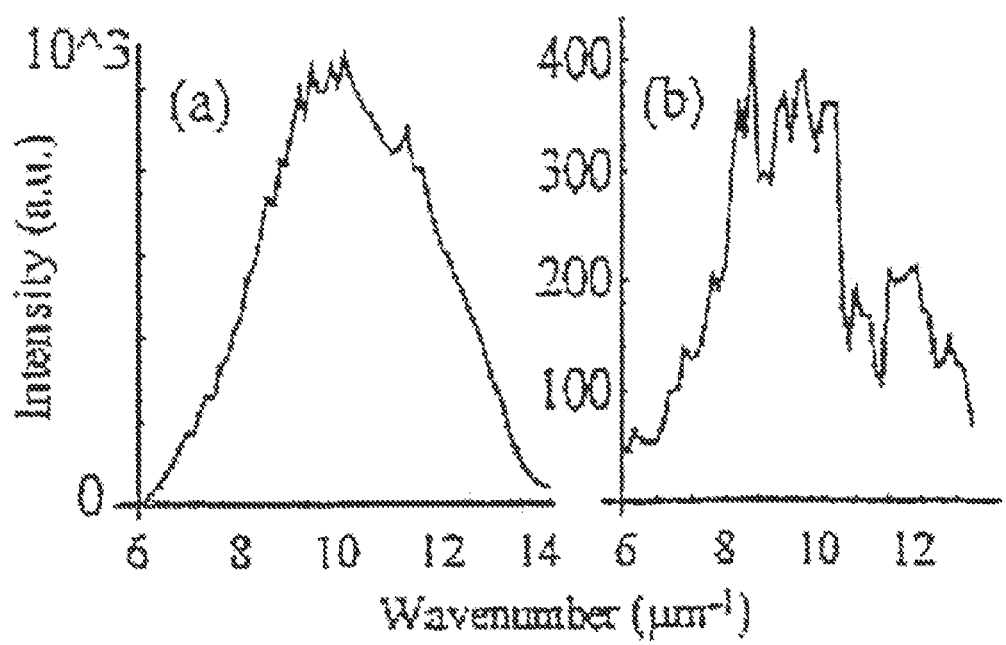
FIGS. 4A and 4B are diagrams of exemplary spectra obtained for front and back surfaces, respectively, of a coverglass sample when no microspheres are present.

FIGS. 4A and 4B show the spectrum obtained for light scattered from the front (a) and back (b) surfaces of a coverglass sample respectively, when no microspheres are present. The reflection from the front surface appears as a slightly modulated version of the source spectrum. The spectrum of the reflection from the rear surface however has been significantly modified. Thus in equation 3, it is now taken that $E_{front}(k) = E_s(k)$ and $E_{back}(k) = T(k)E_s(k)$, where $T(k)$ represents the transmission through the coverslip.

Figures 4C, 4D:
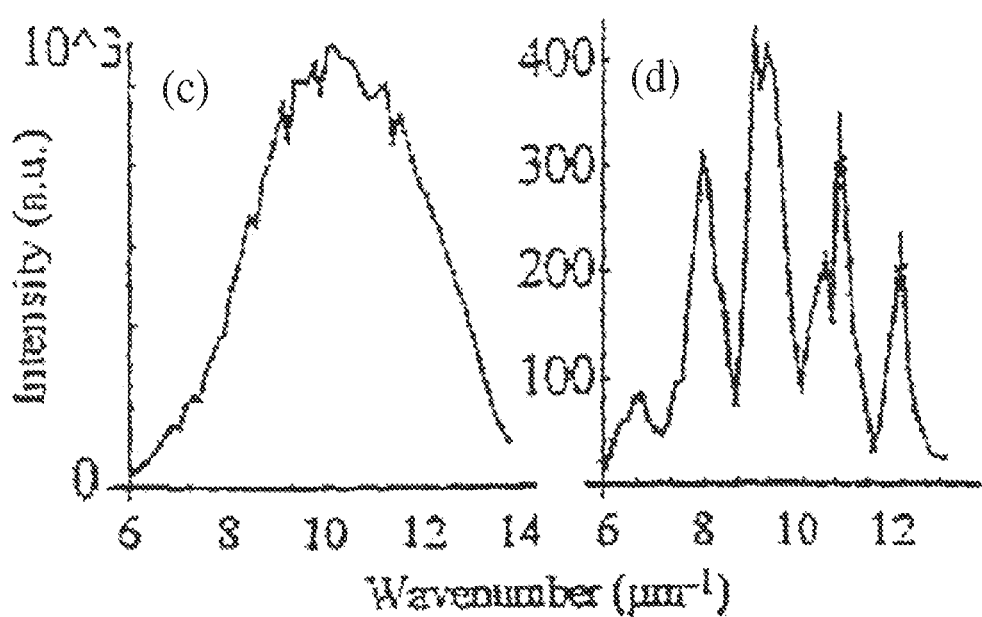
FIGS. 4C and 4D are diagrams of exemplary spectra obtained for front and back surfaces, respectively, of a coverglass sample when microspheres are present.

In FIGS. 4C and 4D, the spectra for light scattering obtained for front (a) and back (b) surfaces of a coverglass sample when microspheres are present on the back surface of the coverslip are shown in FIG. 4C and FIG. 4D. It can be seen that the reflected spectrum from the front surface has not changed significantly, as expected. However, the spectrum for the back surface is now modulated. One can examine the scattering properties $S(k)$ of the microspheres by writing the scattered field as $E_{spheres}(k) = S(k)T(k)E_s(k)$ and taking the ratio $E_{spheres}(k)/E_{back}(k) = S(k)$, which is shown as a solid line in FIG. 6A. It can be seen from this ratio that the microspheres induce a periodic modulation of the spectrum.

As will be discussed in more detail below, it also possible to provide a multiple window (MW), for example a dual window (DW) technique, to obtain depth-resolved spectral information. When providing one window, as discussed above, the same window size is provided for recovering both depth and spectral information. A tradeoff exists when providing a single window size for sampling the interference term. When a single window size is provided, resolution is lost in both the spectral and depth information from the interference term. This is because applying a wide window provides lower resolution spectral information, but provides higher resolution depth information due to the nature of the Fourier transform. Applying a narrow window provides lower resolution depth information, but provides higher resolution spectral information due to the nature of the Fourier transform. Thus, by providing a single window that provides a compromise between a wide and narrow window of the interference term, resolution information is lost for both the spectral and depth information about the sample.

To obtain depth-resolved spectroscopic information, the DW technique is used in certain embodiments disclosed herein. In this regard, FIG. 5A illustrates diagrams of interferograms 500, 502 of exemplary spectra obtained from a sample with first narrower windows 504 applied to the interference term before performing the Fourier transform operation to obtain high resolution spectral information about the sample, and second wider windows 506 applied to the interference term before performing the Fourier transform operation to obtain high resolution depth information about the sample. The DW technique consists of multiplying two STFTs that operate on each interferogram 502, 502. A STFT is implemented by sweeping a window across the interferometric data while simultaneously taking a Fourier transform at each step, thus giving a map of the spectral content confined within a spatial (or axial) region. These maps are known as time-frequency distributions (TFDs). However, TFDs obtained using a single STFT suffer from an inherent tradeoff between the resulting spectral and spatial resolutions. The DW technique, on the other hand, utilizes the high spectral resolution of an STFT using a narrow window, and the high spatial resolution of an STFT using a wide window to avoid the deleterious effects of the time-frequency trade-off. Here in this example, Gaussian windows were used with standard deviations $w1 = 0.029\ \mu m\text{-}1$ and $w2 = 0.804\ \mu m\text{-}1$, resulting in TFDs with an axial resolution of 3.45 μm and spectral resolution of 1.66 nm. Note that this process is conducted for each A-scan, thus giving a spectrum for each point in an OCT image.

FIG. 5B illustrates depth-resolved spectral information profile diagrams 508, 510 of exemplary resulting high resolution spectral and depth information about the sample, respectively, as a function of wave number and depth after performing a Fourier transform to interference term in FIG. 5A. As shown in FIG. 5B, diagram 508 provides higher resolution spectral information, but lower resolution depth information. Diagram 510 in FIG. 5B provides higher resolution depth information, but lower resolution spectral information. This process involves using the images to identify the contour of the tissue surfaces and calibrate the analysis relative to this "zero" depth. Note that if a surface is not clearly discernable at any particular A-scan, no further analysis is conducted there. With this information, the DW TFDs can be properly aligned and thus consistently provide spectral information from specific tissue depths.

Once the spectra are properly aligned in FIG. 5B, regions of interest, both laterally and axially, are identified and averaged in order to provide sufficient signal-to-noise ratio for the spectral analysis that follows. In the lateral direction in this example, twenty (20) DW TFDs are averaged to yield ten (10) different lateral segments in each OCT image. Note that in previous studies, all TFDs in an image were averaged; thus, the analysis provided here produces a ten-fold increase of the spatial information. In the axial direction, the spectral averages of 25 μm depth segments in this example can be calculated from three different sections: at the surface (surface section 0-25 μm), centered about 35 μm in depth (mid section. 22.5-47.5 μm), and centered about 50 μm in depth (low section 37.5-62.5 μm).

To obtain a single depth-resolved spectral information profile that includes both higher resolution spectral and depth information regarding the sample, the depth-resolved spectral information profile diagrams or OCT images 508, 510 in FIG. 5B can be combined or co-registered, as illustrated in FIG. 5C. FIG. 5C is an exemplary diagram 512 of combined higher resolution spectral and depth information depth-resolved spectral information profiles 508, 510 in FIG. 5B combined together to provide a single depth-resolved spectral information profile regarding the sample that includes higher resolution spectral and depth information. The diagram 512 in FIG. 5C is provided by co-registering the OCT images 508, 510 in FIG. 5B with the DW TFDs.

Providing a depth-resolved spectral information profile that includes higher resolution spectral and depth information allows isolation and observation of scattering properties of the sample down to a high resolution, such as down to micrometers of depth, as illustrated in FIG. 5C. This allows observation of absorption features of the cells of the sample. Thus, with higher resolution spectral properties, scattering properties as a function of color may be identified and distinguished at depths, as opposed to a lower resolution depth-resolved spectral information profile, where wavelength information is mixed losing the ability to specifically pinpoint color properties from the scattering properties of the sample as a function of depth.

Obtaining higher resolution scattering properties allows analysis of the scatting properties within a few micrometers, as an example, as opposed to a larger area with scattering properties averaged due to lower resolution information. Thus, obtaining higher resolution scattering properties may also allow providing accurate color information for scattering properties. For example, hemoglobin in blood appears red in color, because hemoglobin absorbs blue light. Thus, by providing higher resolution depth information of scattering properties without compromising higher resolution spectral information, hemoglobin may be accurately identified in the depth-resolved spectral information profile of the sample. Also, absorption of biological absorbers, may be viewable and discernable with higher resolution depth-resolved spectral information profile. Examples of biological absorbers include Hemoglobin and melanin. The biological absorbers may also include contracts agents for example, such as fluoroscene. The present application is not limited to any particular contrast agents.

Figure 6A:
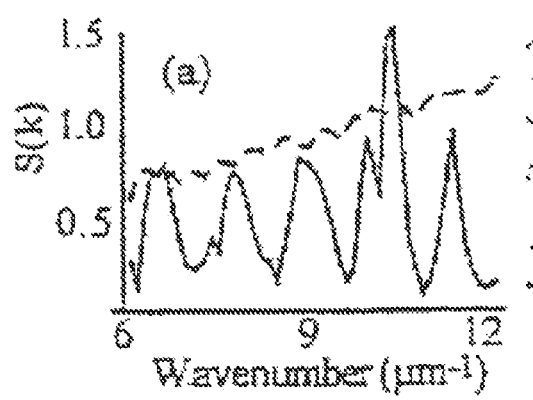
FIGS. 6A and 6B are diagrams of exemplary ratios of spectra in FIGS. 4A through 5C illustrating scattering efficiency of spheres for front and back surface reflections.
Figure 6B:
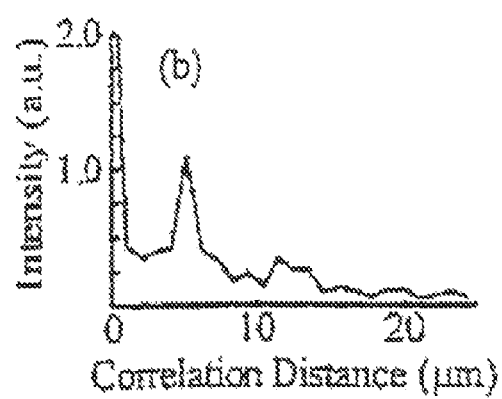

Turning back to an example of a single window technique. in FIG. 6A, ratios of the spectra found in FIGS. 4A and 4B, and FIGS. 4C and 4D are shown. This illustrates the scattering efficiency of spheres for front (represented by the dashed line) and back (represented by the solid line) surface reflections. In FIG. 6B, a correlation function obtained from ratio of back surface reflections is shown. The peak occurs at the round trip optical path through individual microspheres, permitting the size of the spheres to be determined with sub-wavelength accuracy.

For comparison, the same ratio for the front surface reflections (dashed line in FIG. 6A) shows only a small linear variation. Taking the Fourier transform of S(k) yields a clear correlation peak (FIG. 6B), at a physical distance of z=5.24 μm. This can be related to the optical path length through the sphere by z=2nl with the index of the microspheres n=1.59. The diameter of the microspheres to be l=1.65 μm+/−0.33 μm, with the uncertainty given by the correlation pixel size. Thus with fLCI, one is able to determine the size of the microspheres with sub-wavelength accuracy, even exceeding the resolution achievable with this white light source and related art LCI imaging.

There are many applications of the various exemplary embodiments of the present application. One exemplary application of fLCI is in determining the size of cell organelles, in particular the cell nucleus, in epithelial tissues. In biological media, for example, the relative refractive indices are lower for organelles compared to microspheres and thus, smaller scattering signals are expected. The use of a higher power light source will permit the smaller signals to be detected. Other examples include detection of sub-surface defects in manufactured parts, including fabricated integrated circuits, detection of airborne aerosols, such as nerve agents or biotoxins, and detection of exposure to such aerosols by examining epithelial tissues within the respiratory tract.

Additionally, the larger the size of the nucleus (compared to the microspheres in this experiment), the higher the frequency modulation of the spectrum. Those skilled in the art will appreciate that higher frequency oscillations are detected at a lower efficiency in Fourier transform spectroscopy techniques. Therefore, in order to detect these higher frequency oscillations, a higher resolution spectrograph is used.

Figure 7:
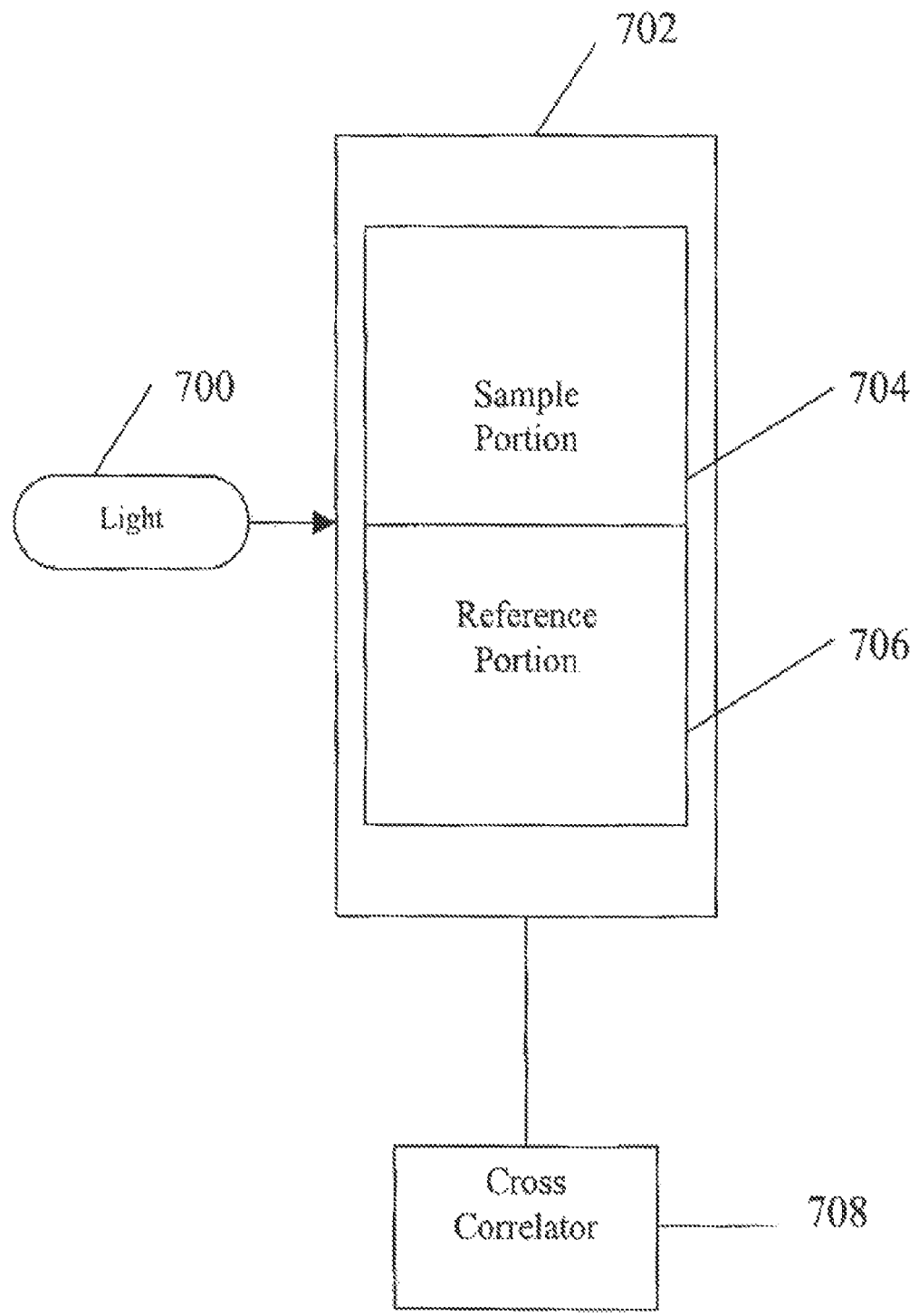
FIG. 7 is a diagram of a generalized version of the system shown in FIGS. 1A and 1B.

FIG. 7 illustrates a generalized embodiment of the fLCI system shown in FIG. 1 and discussed in greater detail above. In FIG. 7, a light source 700 (e.g. a multi-wavelength light) is coupled into an fLCI system 702. Within the fLCI system 702, a sample portion 704 and a reference portion 706 are located. The sample portion 704 includes a light beam and light scattered from a sample. For example, the sample portion 704 may include a sample holder, a free space optical arm, or an optical fiber. The reference portion 706 includes a light beam and light that is reflected from a reference. For example, the reference portion 706 may include an optical mirror. A cross-correlator 708 receives and cross-correlates light from the sample with light from the reference.

Exemplary fa/LCI Systems

The DW technique is also applicable to a/LCI systems, including the a/LCI technique called Fourier domain a/LCI (fa/LCI), which enables data acquisition at rapid rates using a single scan, sufficient to make in vivo applications feasible. Angle-resolved and depth-resolved spectra information may be obtained about a sample, in which depth and size information about the sample can be obtained with a single scan, and wherein the reference arm can remain fixed with respect to the sample due to only one scan required. A reference signal and a scattered sample signal are cross-correlated and dispersed at a multitude of scattered angles off of the sample, thereby representing scatterers from a multitude of points on the sample at the same time in parallel.

Since this angle-resolved, cross-correlated signal is spectrally dispersed, the new data acquisition scheme is significant as it permits data to be obtained in less than one second, a threshold determined to be necessary for acquiring data from in vivo tissues. Information about all depths of the sample at each of the multitude of different points on the sample can be obtained with one scan on the order of approximately 40 milliseconds. From the spatial, cross-correlated reference signal, structural (size) information can also be obtained using techniques that allow size information of scatterers to be obtained from angle-resolved data.

The fa/LCI technique uses the Fourier domain concept to acquire depth resolved information. Signal-to-noise and commensurate reductions in data acquisition time are possible by recording the depth scan in the Fourier (or spectral) domain. The fa/LCI system combines the Fourier domain concept with the use of an imaging spectrograph to spectrally record the angular distribution in parallel. Thereafter, the depth-resolution is achieved by Fourier transforming the spectrum of two mixed fields with the angle-resolved measurements obtained by locating the entrance slit of the imaging spectrograph in a Fourier transform plane to the sample. This converts the spectral information into depth-resolved information and the angular information into a transverse spatial distribution. The capabilities of fa/LCI have been initially demonstrated by extracting the size of polystyrene beads in a depth-resolved measurement.

Figure 8A:
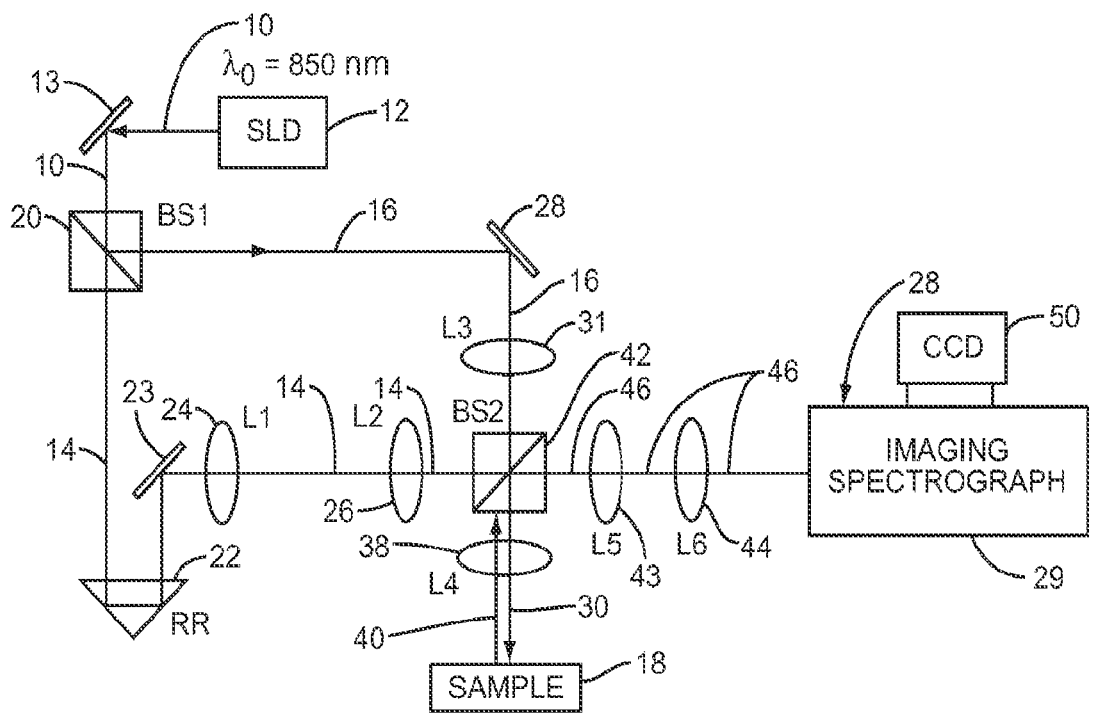
FIG. 8A is a schematic of one exemplary embodiment of the fa/LCI system employing Mach-Zehnder interferometer.
Figure 9:
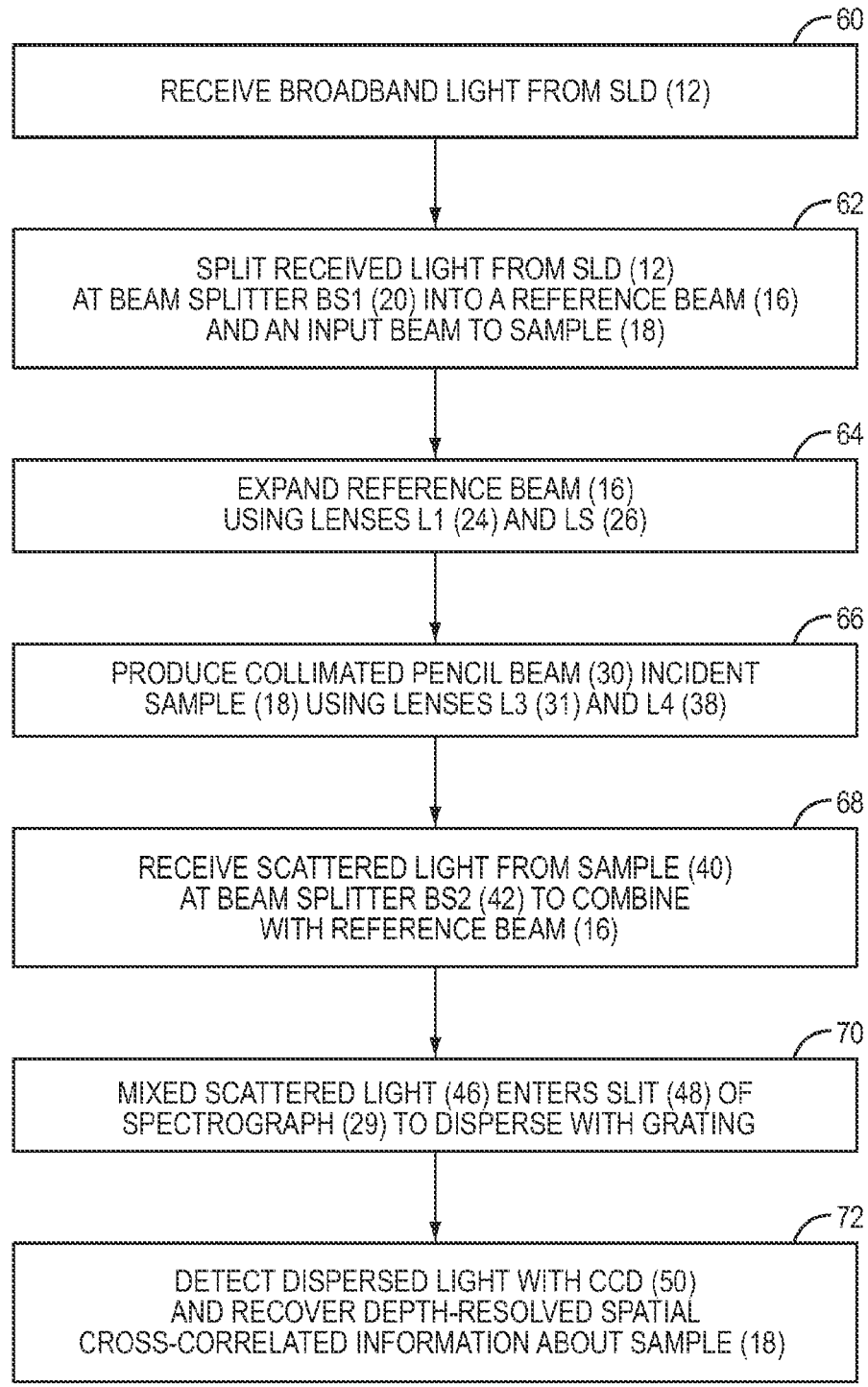
FIG. 9 is a flowchart illustrating the steps performed by an interferometer apparatus to recover depth-resolved spatial cross-correlated information about the sample for analysis.

An exemplary apparatus, as well as the steps involved in the process of obtaining angle and depth-resolved distribution data scattered from a sample, are also set forth in FIG. 9. The fa/LCI scheme in accordance with one embodiment is based on a modified Mach-Zehnder interferometer as illustrated in FIG. 8A. Broadband light 11 from a superluminescent diode (SLD) 12 is directed by a mirror 13 (step 60 in FIG. 9) and split into a reference beam 14 and an input beam 16 to a sample 18 by beamsplitter BS1 20 (step 62 in FIG. 9). The output power of the SLD 12 may be 3 milliWatts, having a specification of $\lambda_0$=850 nm, $\Delta\lambda$=20 nm FWHM for example, providing sufficiently low coherence length to isolate scattering from a cell layer within tissue. The path length of the reference beam 14 is set by adjusting retroreflector RR 22, but remains fixed during measurement. The reference beam 14 is expanded using lenses L1 (24) and L2 (26) to create illumination (step 64 in FIG. 9), which is uniform and collimated upon reaching a spectrograph slit 48 in an imaging spectrograph 29. For example, L1 may have a focal length of 1.5 centimeters, and L2 26 may have focal length of 15 centimeters.

Lenses L3 (31) and L4 (38) are arranged to produce a collimated pencil beam 30 incident on the sample 18 (step 66 in FIG. 9). By displacing lens L4 (38) vertically relative to lens L3 (31), the input beam 30 is made to strike the sample at an angle of 0.10 radians relative to the optical axis. This arrangement allows the full angular aperture of lens L4 (38) to be used to collect scattered light 40 from the sample 18. Lens L4 (38) may have a focal length of 3.5 centimeters.

Figure 8B:
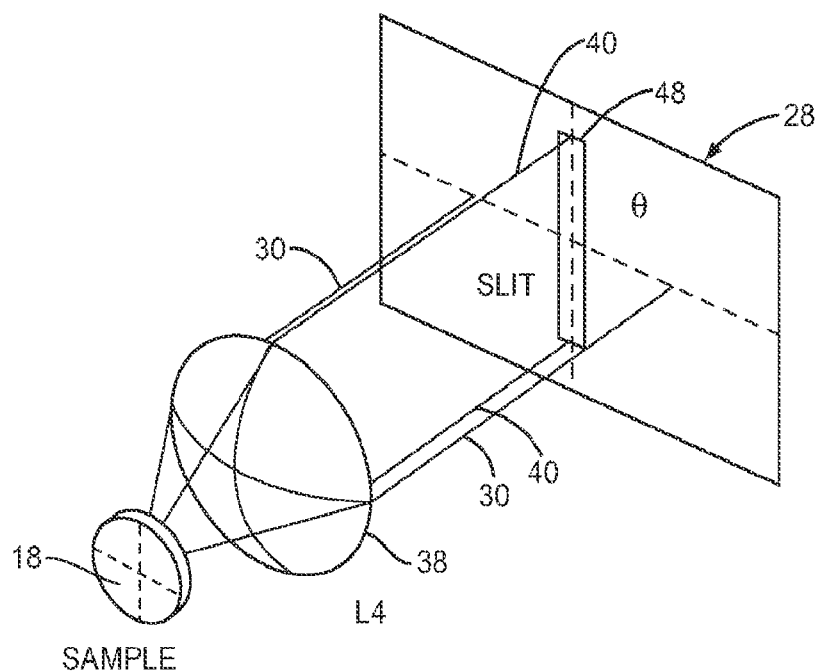
FIG. 8B is an illustration showing the relationship of the detected scattering angle to slit of spectrograph in the interferometer arrangement of FIG. 8A.

The light 40 scattered by the sample 18 is collected by lens L4 (32) and relayed by a 4f imaging system comprised of lenses L5 (43) and L6 (44) such that the Fourier plane of lens L4 (32) is reproduced in phase and amplitude at the spectrograph slit 48 (step 68 in FIG. 9). The scattered light 40 is mixed with the reference field 14 at a second beamsplitter BS2 42 with the combined fields 46 falling upon the entrance slit (illustrated in FIG. 8B as element 48) to the imaging spectrograph 29 (step 70 in FIG. 9). The imaging spectrograph 29 may be the model SP2150i, manufactured by Acton Research for example. FIG. 8B illustrates the distribution of scattering angle across the dimension of the slit 48. The mixed fields are dispersed with a high resolution grating (e.g. 1200 l/mm) and detected using a cooled CCD 50 (e.g. 1340×400, 20 μm×20 μm pixels, Spec10:400, manufactured by Princeton Instruments) (step 72 in FIG. 9).

The detected signal 46 is a function of vertical position on the spectrograph slit 48, y, and wavelength λ once the light is dispersed by the spectrograph 29. The detected signal at pixel (m,n) can be related to the signal 40 and reference fields 16 ($E_s$, $E_r$) as)

$$I(\lambda_m, y_n) = \langle |E_r(\lambda_m, y_n)|^2 \rangle + \langle |E_s(\lambda_m, y_n)|^2 \rangle + 2Re \langle E_s(\lambda_m, y_n) E_r^*(\lambda_m, y_n) \rangle \cos\phi, \quad (5)$$

where ϕ is the phase difference between the two fields 30, 16 and ⟨ ... ⟩ (denotes an ensemble average in time. The interference term is extracted by measuring the intensity of the signal 30 and reference beams 16 independently and subtracting them from the total intensity.

In order to obtain depth resolved information, the wavelength spectrum at each scattering angle is interpolated into a wavenumber (k=2π/λ) spectrum and Fourier transformed to give a spatial cross correlation, $\Gamma_{SR}(z)$ for each vertical pixel $y_n$:

$$\Gamma_{SR}(z, y_n) = dk e^{ikz} \langle E_s(k, y_n) E_r^*(k, y_n) \rangle \cos\phi. \quad (6)$$

The reference field 14 takes the form:

$$E_r(k) = E_o \exp[-((k-k_o)/\Delta k)^2] \exp[-((y-y_o)/\Delta y)^2] \exp[ik\Delta l] \quad (7)$$

where $k_o$ ($y_o$ and $\Delta k$ ($\Delta y$) represent the center and width of the Gaussian wavevector (spatial) distribution and $\Delta l$ is the selected path length difference. The scattered field 40 takes the form $$E_s(k,\theta) = E_o \exp[-((k-k_o)/\Delta k)^2] \exp[ikl_j] S_j(k,\theta) \quad (8)$$

where $S_j$ represents the amplitude distribution of the scattering originating from the jth interface, located at depth $l_j$. The angular distribution of the scattered field 40 is converted into a position distribution in the Fourier image plane of lens L4 through the relationship y=$f_4$θ. For the pixel size of the CCD 50 (e.g. 20 μm), this yields an angular resolution (e.g. 0.57 mrad) and an expected angular range (e.g. 228 mrad.).

Inserting Eqs. (7) and (8) into Eq. (6) and noting the uniformity of the reference field 14 (Δy>>slit height) yields the spatial cross correlation at the nth vertical position on the detector 29:

$$\Gamma_{SR}(z, y_n) = \sum_j \int dk |E_o|^2 \exp[-2((k-k_o)/\Delta k)^2] \exp[ik(z-\Delta l + l_j)] \times S_j(k, \theta_n = y_n/f_4) \cos\phi. \quad (9)$$

Evaluating this equation for a single interface yields:

$$\Gamma_{SR}(z, y_n) = |E_o|^2 \exp[-((z-\Delta l + l_j)\Delta k)^2/8] S_j(k_o, \theta_n = y_n/f_4) \cos\phi. \quad (10)$$

Here in this example, it is assumed that the scattering amplitude S does not vary appreciably over the bandwidth of the source light 12. This expression shows that one can obtain a depth resolved profile of the scattering distribution 40 with each vertical pixel corresponding to a scattering angle.

Figure 10A:
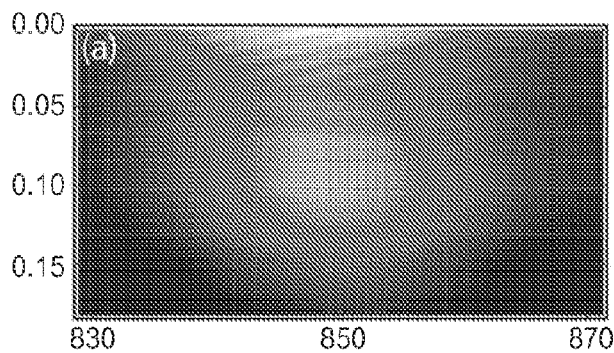
FIGS. 10A-D illustrate examples of fa/LCI data recovered in the spectral domain for an exemplary sample of polystyrene beads, comprising the total acquired signal (FIG. 10A), the reference field intensity (FIG. 10B), the signal field intensity (FIG. 10C), and the extracted, cross-correlated signal between the reference and signal field intensities (FIG. 10D)

FIG. 10A below shows typical data representing the total detected intensity (Equation (5), above) of the sum of the reference field 16 and the field scattered 40 by a sample of polystyrene beads, in the frequency domain given as a function of wavelength and angle, given with respect to the backwards scattering direction. In an exemplary embodiment, this data was acquired in 40 milliseconds and records data over 186 mrad, approximately 85% of the expected range, with some loss of signal at higher angles.

Figure 10B:
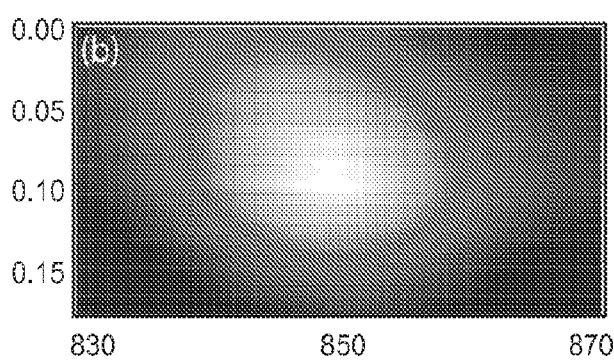
Figure 10C:
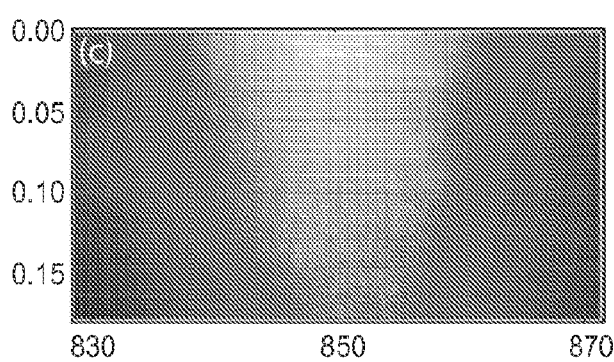
Figure 10D:
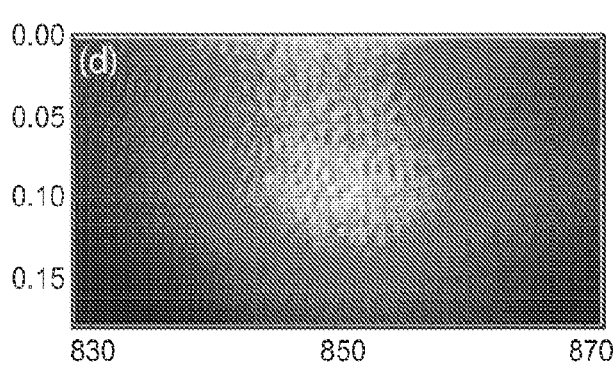
Figure 11A:
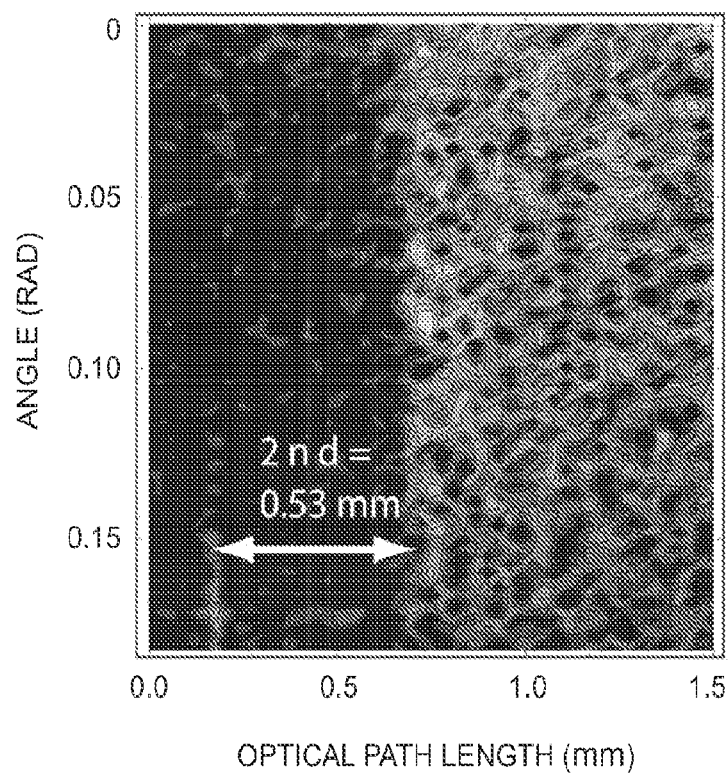
FIG. 11A is an illustration of the axial spatial cross-correlated function performed on the cross-correlated fa/LCI data illustrated in FIG. 10D as a function of depth and angle.

FIGS. 10B and 10C illustrate the intensity of the reference and signal fields 14, 30 respectively. Upon subtraction of the signal and reference fields 14, 30 from the total detected intensity, the interference 46 between the two fields is realized as illustrated in FIG. 10D. At each angle, interference data 46 are interpolated into k-space and Fourier transformed to give the angular depth resolved profiles of the sample 18 as illustrated in FIG. 11A. The Fourier transform of the angle-resolved, cross correlated signal 46, which is the result of signal 40 scattered at a multitude of angles off the sample 18 and obtained in the Fourier plane of lens L4 (32), produces depth-resolved information about the sample 18 as a function of angle and depth. This provides depth-resolved information about the sample 18. Because the angle-resolved, cross-correlated signal 46 is spectrally dispersed, the data acquisition permits data to be obtained in less than one second. Information about all depths of the sample 18 at each of the multitude of different points (i.e. angles) on the sample 18 can be obtained with one scan on the order of approximately 40 milliseconds. Normally, time domain based scanning is required to obtain information about all depths of a sample at a multitude of different points, thus requiring substantial time and movement of the reference arm with respect to the sample.

In the experiments that produced the depth-resolved profit of the sample 18 illustrated in FIG. 11A, the sample 18 consists of polystyrene microspheres (e.g. n=1.59, 10.1 μm mean diameter, 8.9% variance, NIST certified, Duke Scientific) suspended in a mixture of 80% water and 20% glycerol (n=1.36) to provide neutral buoyancy. The solution was prepared to obtain a scattering length l=200 μm. The sample is contained in a round well (8 mm diameter, 1 mm deep) behind a glass coverslip (thickness, d~170 μm) (not shown). The sample beam 30 is incident on the sample 18 through the coverslip. The round trip thickness through the coverslip (2 n d=2 (1.5) (170 μm)=0.53 mm—see FIG. 11A) shows the depth resolved capability of the approach. The data are ensemble averaged by integrating over one mean free path (MFP). The spatial average can enable a reduction of speckle when using low-coherence light to probe a scattering sample. To simplify the fitting procedure, the scattering distribution is low pass filtered to produce a smoother curve, with the cutoff frequency chosen to suppress spatial correlations on length scales above 16 μm.

Figure 11B:
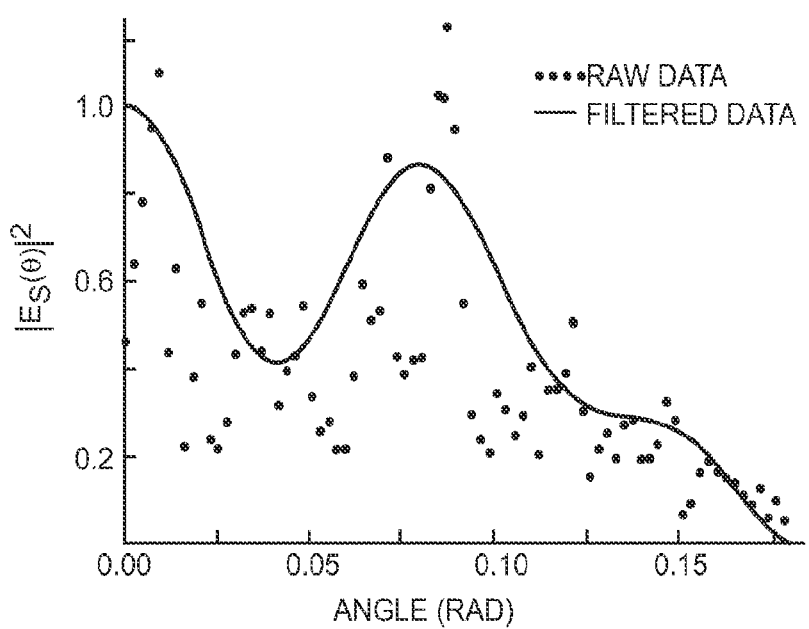
FIG. 11B is an illustration of an angular distribution plot of raw and filtered data regarding scattered sample signal intensity as a function of angle in order to recover size information about the sample.
Figure 12A:
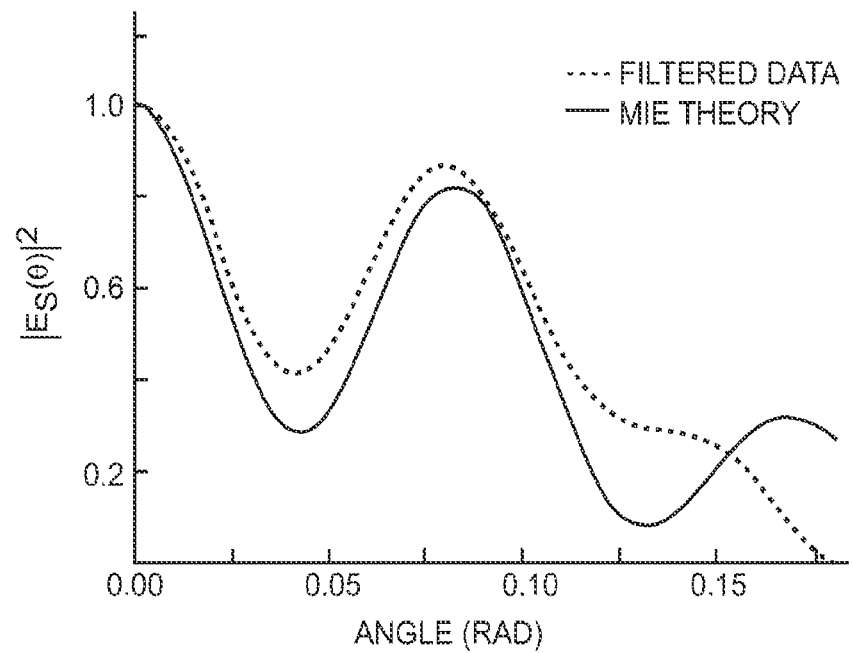
FIG. 12A is an illustration of the filtered angular distribution of the scattered sample signal intensity compared to the best fit Mie theory to determine size information about the sample.

In addition to obtaining depth-resolved information about the sample 18, the scattering distribution data (i.e. a/LCI data) obtained from the sample 18 using the disclosed data acquisition scheme can also be used to make a size determination of the nucleus using the Mie theory. A scattering distribution 74 of the sample 18 is illustrated in FIG. 11B as a contour plot. The raw scattered information 74 about the sample 18 is shown as a function of the signal field 30 and angle. A filtered curve is determined using the scattered data 74. Comparison of the filtered scattering distribution curve 76 (i.e. a representation of the scattered data 74) to the prediction of Mie theory (curve 78 in FIG. 12A) enables a size determination to be made.

In order to fit the scattered data 76 to Mie theory, the a/LCI signals are processed to extract the oscillatory component which is characteristic of the nucleus size. The smoothed data 76 are fit to a low-order polynomial ($4^{th}$ order was used for example herein, but later studies use a lower $2^{nd}$ order), which is then subtracted from the distribution 76 to remove the background trend. The resulting oscillatory component is then compared to a database of theoretical predictions obtained using Mie theory 78 from which the slowly varying features were similarly removed for analysis.

A direct comparison between the filtered a/LCI data 76 and Mie theory data 78 may not possible, as the chi-squared fitting algorithm tends to match the background slope rather than the characteristic oscillations. The calculated theoretical predictions include a Gaussian distribution of sizes characterized by a mean diameter (d) and standard deviation (δD) as well as a distribution of wavelengths, to accurately model the broad bandwidth source.

Figure 12B:
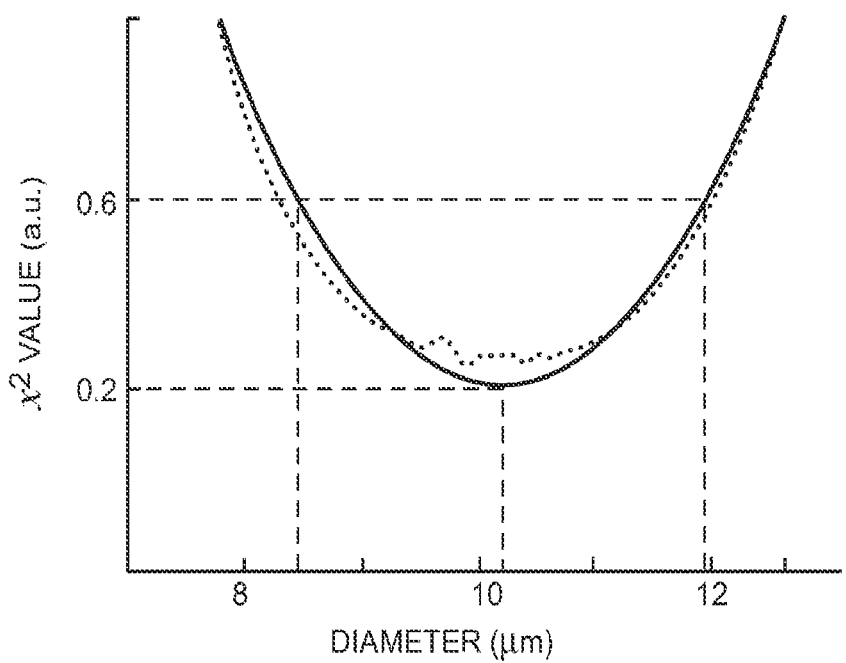
FIG. 12B is a Chi-squired minimization of size information about the sample to estimate the diameter of cells in the sample.

The best fit (FIG. 12A) is determined by minimizing the Chi-squared between the data 76 and Mie theory (FIG. 12B), yielding a size of 10.2+/−1.7 μm, in excellent agreement with the true size. The measurement error is larger than the variance of the bead size, most likely due to the limited range of angles recorded in the measurement.

As an alternative to processing the a/LCI data and comparing to Mie theory, there are several other approaches which could yield diagnostic information. These include analyzing the angular data using a Fourier transform to identify periodic oscillations characteristic of cell nuclei. The periodic oscillations can be correlated with nuclear size and thus will possess diagnostic value. Another approach to analyzing a/LCI data is to compare the data to a database of angular scattering distributions generated with finite element method (FEM) or T-Matrix calculations. Such calculations may offer superior analysis as there are not subject to the same limitations as Mie theory. For example, FEM or T-Matrix calculations can model non-spherical scatterers and scatterers with inclusions while Mie theory can only model homogenous spheres.

Figure 13:
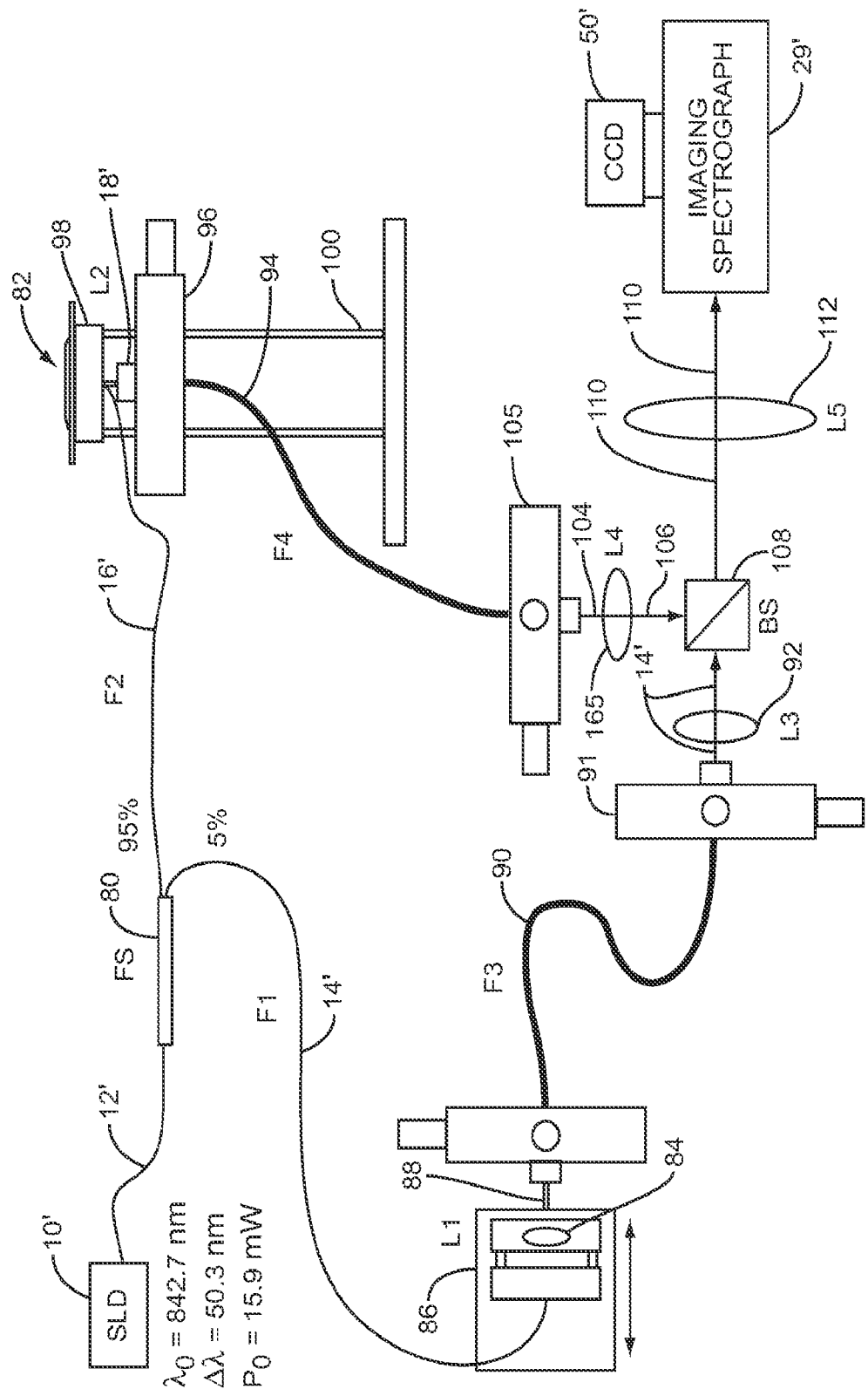
FIG. 13 is a schematic of an exemplary embodiment of the fa/LCI system employing an optical fiber probe.

As an alternative embodiment, the systems described herein can also employ optical fibers to deliver and collect light from the sample of interest to use in the a/LCI system for endoscopic applications. This alternative embodiment is illustrated in FIG. 13.

The fiber optic a/LCI scheme for this alternative embodiment makes use of the Fourier transform properties of a lens. This property states that when an object is placed in the front focal plane of a lens, the image at the conjugate image plane is the Fourier transform of that object. The Fourier transform of a spatial distribution (object or image) is given by the distribution of spatial frequencies, which is the representation of the image's information content in terms of cycles per mm.

In an optical image of elastically scattered light, the wavelength retains its fixed, original value and the spatial frequency representation is simply a scaled version of the angular distribution of scattered light.

In the fiber optic a/LCI scheme, the angular distribution is captured by locating the distal end of the fiber bundle in a conjugate Fourier transform plane of the sample using a collecting lens. This angular distribution is then conveyed to the distal end of the fiber bundle where it is imaged using a 4f system onto the entrance slit of an imaging spectrograph. A beamsplitter is used to overlap the scattered field with a reference field prior to entering the slit so that low coherence interferometry can also be used to obtain depth resolved measurements.

Turning now to FIG. 13, the fiber optic fa/LCI scheme is shown. Light 12' from a broadband light source 11' is split into a reference field 14' and a signal field 16' using a fiber splitter (FS) 80. A splitter ratio of 20:1 is chosen in one embodiment to direct more power to a sample 18' via the signal arm 82 as the light returned by the tissue is typically only a small fraction of the incident power. Alternatively, the light source 11' could be provided by another light source, such as a super continuum laser, or swept-source laser, as described in U.S. patent application Ser. No. 12/210,620 titled "APPARATUSES, SYSTEMS AND METHODS FOR LOW-COHERENCE INTERFEROMETRY (LCI)," which is incorporated herein by reference in its entirety.

Light in the reference fiber 14' emerges from fiber F1 and is collimated by lens L1 (84), which is mounted on a translation stage 86 to allow gross alignment of the reference arm path length. This path length is not scanned during operation but may be varied during alignment. A collimated beam 88 is arranged to be equal in dimension to the end 91 of fiber bundle F3 (90) so that the collimated beam 88 illuminates all fibers in F3 with equal intensity. The reference field 14' emerging from the distal tip of F3 (90) is collimated with lens L3 (92) in order to overlap with the scattered field conveyed by fiber F4 (94). In an alternative embodiment, light emerging from fiber F1 (14') is collimated then expanded using a lens system to produce a broad beam.

Figure 14A:
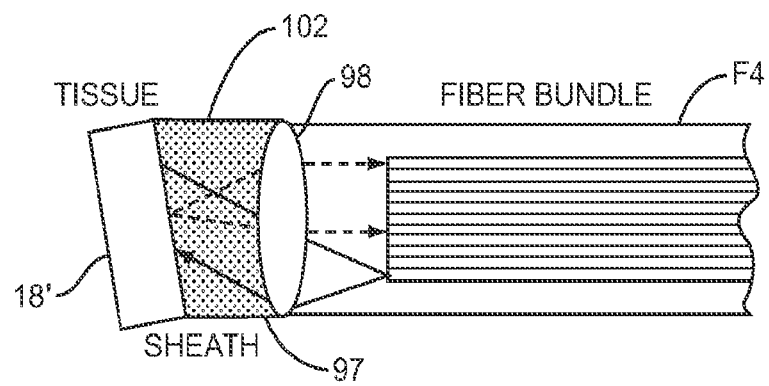
FIG. 14A is a cutaway view of an a/LCI fiber-optic probe tip that may be employed by the fa/LCI system illustrated in FIGS. 6A and 6B.

The scattered field is detected using a coherent fiber bundle. The scattered field is generated using light in the signal arm 82 which is directed toward the sample 18' of interest using lens L2 (98). As with the free space system, lens L2 (98) is displaced laterally from the center of single-mode fiber F2 such that a collimated beam is produced which is traveling at an angle relative to the optical axis The fact that the incident beam strikes the sample at an oblique angle is essential in separating the elastic scattering information from specular reflections. The light scattered by the sample 18' is collected by a fiber bundle consisting of an array of coherent single mode or multi-mode fibers. The distal tip of the fiber is maintained one focal length away from lens L2 (98) to image the angular distribution of scattered light. In the embodiment shown in FIG. 13, the sample 18' is located in the front focal plane of lens L2 (98) using a mechanical mount 1100. In the endoscope compatible probe shown in FIG. 14A, the sample is located in the front focal plane of lens L2 (98) using a transparent sheath (element 1102).

Figure 14B:
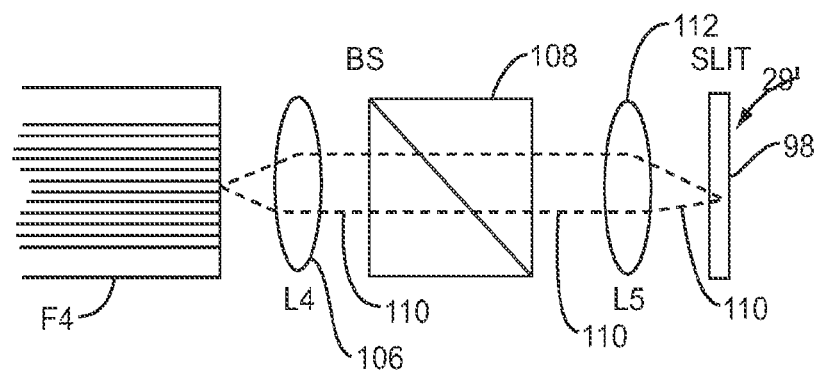
FIG. 14B illustrates the location of the fiber probe in the fa/LCI system illustrated in FIG. 14A.

As illustrated in FIG. 13 and also FIG. 14B, scattered light 1104 emerging from a proximal end 1105 of the fiber probe F4 (94) is recollimated by lens L4 (1104) and overlapped with the reference field 14' using beamsplitter BS (1108). The two combined fields 1110 are re-imaged onto the slit (element 48' in FIG. 14) of the imaging spectrograph 29' using lens L5 (1112). The focal length of lens L5 (1112) may be varied to optimally fill the slit 48'. The resulting optical signal contains information on each scattering angle across the vertical dimension of the slit 48' as described above for the apparatus of FIGS. 8A and 8B.

It is expected that the above-described a/LCI fiber-optic probe will collect the angular distribution over a 0.45 radian range (approx. 30 degrees) and will acquire the complete depth resolved scattering distribution 1110 in a fraction of a second.

There are several possible schemes for creating the fiber probe which are the same from an optical engineering point of view. One possible implementation would be a linear array of single mode fibers in both the signal and reference arms. Alternatively, the reference arm 96 could be composed of an individual single mode fiber with the signal arm 82 consisting of either a coherent fiber bundle or linear fiber array.

The fiber probe tip can also have several implementations which are substantially equivalent. These would include the use of a drum or ball lens in place of lens L2 (98). A side-viewing probe could be created using a combination of a lens and a mirror or prism or through the use of a convex mirror to replace the lens-mirror combination. Finally, the entire probe can be made to rotate radially in order to provide a circumferential scan of the probed area.

Yet another data acquisition embodiment could be a fa/LCI system is based on a modified Mach-Zehnder interferometer as illustrated in FIG. 15A. The output 10" from a fiber-coupled superluminescent diode (SLD) source 12" (e.g. Superlum, $P_o$=15 mW, $\lambda o$=841.5 nm, $\Delta\lambda$=49.5 nm, coherence length=6.3 µm) is split into sample arm delivery fiber 16" and a reference arm delivery fiber 14" by a 90/10 fiber splitter FS (80') (e.g. manufactured by AC Photonics). The sample arm delivery fiber 16" can consist of either of the following for example: (1) a single mode fiber with polarization control integrated at the tip; or (2) a polarization maintaining fiber. A sample probe 1113 is assembled by affixing the delivery fiber 16"(NA=0.12) along the ferrule 1114 at the distal end of a fiber bundle 1116 such that the end face of the delivery fiber 16" is parallel to and flush with the face of the fiber bundle 1116. Ball lens L1 (1115) (e.g. $f_1$=2.2 mm) is positioned one focal length from the face of the probe 1113 and centered on the fiber bundle 1116, offsetting the delivery fiber 16" from the optical axis of lens L1 (1115). This configuration, which is also depicted in FIG. 15B, produces a collimated beam 1120 (e.g. P=9 mW) with a diameter (e.g. $2f_1$NA) of 0.5 mm incident on the sample 18" at an angle of 0.25 rad. for example.

The scattered light 1122 from the sample is collected by lens L1 (1115) and, via the Fourier transform property of the lens L1 (1115, the angular distribution of the scattered field 1122 is converted into a spatial distribution at the distal face of the multimode coherent fiber bundle 1116 (e.g. Schott North America, Inc., length=840 mm, pixel size=8.2 µm, pixel count=13.5K) which is located at the Fourier image plane of lens L1 (1115). The relationship between vertical position on the fiber bundle, y', and scattering angle, θ is given by $y'=f_1\theta$. As an illustration, the optical path of light scattered 122 at three selected scattering angles is shown in FIG. 15B. Overall, the angular distribution is sampled by approximately 130 individual fibers for example, across a vertical strip of the fiber bundle 16", as depicted by the highlighted area in FIG. 15C. The 0.2 mm, for example, thick ferrule ($d_1$) separating the delivery fiber 16" and fiber bundle 1116 limits the minimum theoretical collection angle ($\theta_{min,th}=d_1/f_1$) to 0.09 rad in this example. The maximum theoretical collection angle is determined by $d_1$ and $d_2$, the diameter of the fiber bundle, by $\theta_{max,th}=(d_1+d_2)/f_1$ to be 0.50 rad. Experiments using a standard scattering sample 1122 indicate the usable angular range to be $\theta_{min}$=0.12 rad. to $\theta_{max}$=0.45 rad. $d_1$, for example, can be minimized by fabricating a channel in the distal ferrule 1123 and positioning the delivery fiber 16" in the channel.

The fiber bundle 1116 is spatially coherent, resulting in a reproduction of the collected angular scattering distribution at the proximal face. Additionally, as all fibers in the bundle 1116 are path length matched to within the coherence length, the optical path length traveled by scattered light 1122 at each angle is identical. "The system disclosed in "Fiber-optic-bundle-based optical coherence tomography," by T. Q. Xie, D. Mukai, S. G. Guo, M. Brenner, and Z. P. Chen in *Optics Letters* 30(14), 1803-1805 (2005) (hereinafter "Xie"), incorporated by reference herein in its entirety, discloses a multi-mode coherent fiber bundle into a time-domain optical coherence tomography system and demonstrated that the modes of light coupled into an individual fiber will travel different path lengths. In one example, it was experimentally determined that the higher order modes are offset from the fundamental mode by 3.75 mm, well beyond the depth (~100 µm) required for gathering clinically relevant data. Additionally, the power in the higher order modes had a minimal affect on dynamic range as the sample arm power is significantly less than the reference arm power. Finally, it should be noted that while the system disclosed in Xie collected data serially through individual fibers, the example disclosed herein uses 130 fibers to simultaneously collect scattered light across a range of angles in parallel, resulting in rapid data collection.

The angular distribution exiting a proximal end 1124 of the fiber bundle 1116 is relayed by the 4f imaging system of L2 and L3 ($f_2$=3.0 cm, $f_3$=20.0 cm) to the input slit 48" of the imaging spectrograph 29" (e.g. Acton Research, InSpectrum 150). The theoretical magnification of the 4f imaging system is ($f_3/f_2$) 6.67 in this example. Experimentally, the magnification was measured to be M=7.0 in this example with the discrepancy most likely due to the position of the proximal face 1124 of the fiber bundle 1116 with relation to lens L2 (126). The resulting relationship between vertical position on the spectrograph slit 48", y, and θ is $y=Mf_1(\theta-\theta_{min})$. The optical path length of the reference arm is matched to that of the fundamental mode of the sample arm. Light 1127 exiting the reference fiber 14" is collimated by lens L4 (1128) (e.g. f=3.5 cm, spot size=8.4 mm) to match the phase front curvature of the sample light and to produce even illumination across the slit 48" of the imaging spectrograph 29". A reference field 1130 may be attenuated by a neutral density filter 1132 and mixed with the angular scattering distribution at beamsplitter BS (1134). The mixed fields 1136 are dispersed with a high resolution grating (e.g. 1200 lines/mm) and detected using an integrated, cooled CCD (not shown) (e.g. 1024×252, 24 µm×24 µm pixels, 0.1 nm resolution) covering a spectral range of 99 nm centered at 840 nm, for example.

The detected signal 1136, a function of wavelength, λ, and θ, can be related to the signal and reference fields (Es, Er) as:

$$I(\lambda_m,\theta_n)=\langle |E_r(\lambda_m,\theta_n)|^2 \rangle + \langle |E_s(\lambda_m,\theta_n)|^2 \rangle +2Re\langle E_s(\lambda_m,\theta_n)E_r^*(\lambda_m,\theta_n)\cos(\phi)\rangle, \quad (11)$$

where φ is the phase difference between the two fields, (m,n) denotes a pixel on the CCD, and ⟨ . . . ⟩ denotes a temporal average. $I(\lambda_m, \theta_n)$ is uploaded to a PC using LabVIEW manufactured by National Instruments software and processed in 320 ms to produce a depth and angle resolved contour plot of scattered intensity. The processing of the angle-resolved scattered field to obtain depth and size information described above, and in particular reference to the data acquisition apparatus of FIGS. 8A and 8B, can then used to obtain angle-resolved, depth-resolved information about the sample 18" using the scattered mixed field 1136 generated by the apparatus in FIGS. 15A-15C.

Dual Window (DW) Techniques

Figure 42:
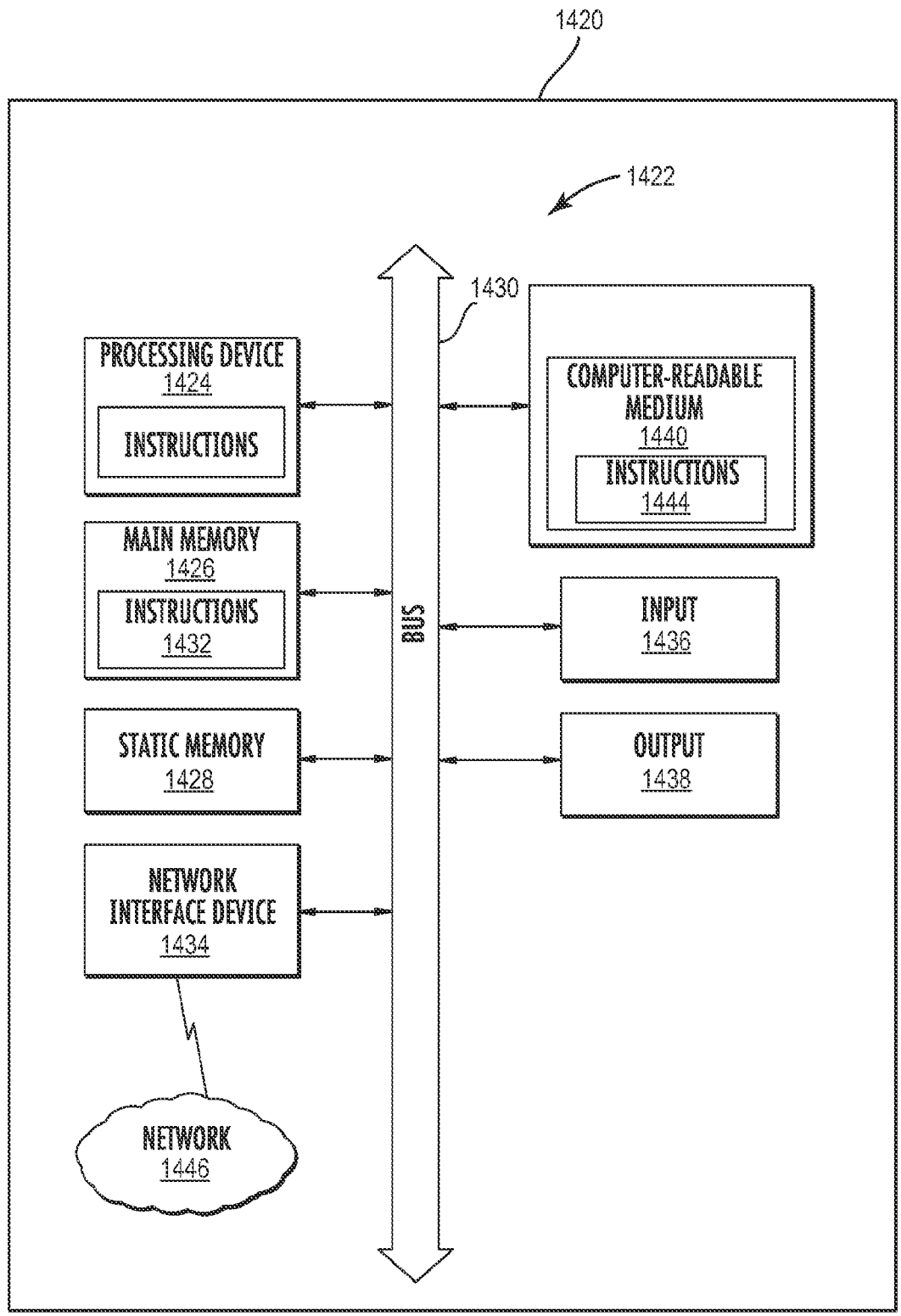
FIG. 42 is a schematic diagram representation of an exemplary machine in the exemplary form of an exemplary computer system adapted to execute instructions from an exemplary computer-readable medium to perform the DW techniques described herein.

The DW apparatuses and methods of the embodiments disclosed herein may be calculated by software executing on a microprocessor coupled to the spectrographs 112 (FIG. 1A), 29 (FIG. 8A), and 29' (FIG. 13), as examples. FIG. 42 discussed below at the end of this disclosure provides a schematic diagram representation of an exemplary machine in the exemplary form of an exemplary computer system adapted to execute instructions from an exemplary computer-readable medium to perform the DW techniques described herein.

The DW apparatuses and methods are based on calculating two or more separate STFTs and then combining the results. In this example, two STFTs are obtained. The first STFT in this example uses a broad spectral Gaussian window to obtain high temporal/depth resolution while the second STFT in this example uses a narrow spectral window to generate high spectroscopic resolution. The two resulting TFDs are then multiplied together to obtain a single TFD with simultaneously high spectral and temporal resolutions.

Mathematical analysis of this approach shows the DW technique is equivalent to probing the Wigner TFD with two orthogonal Gaussian windows, which can be independently tuned in the spectral and spatial/temporal dimensions, thus avoiding the tradeoff that hinders the STFT.

To understand what the DW technique in this example is revealing, consider the FDOCT signal:

$$I(k) = I_R(k) + I_S(k) + 2E_R(k)E_S^*(k) \cdot \cos(k \cdot d), \quad (12)$$

where $I(k)$ is the total detected intensity, $I_R$ and $I_S$ are the intensities of the reference and sample fields, respectively, and $d$ is a constant optical path difference between the sample and reference arms. The STFT of the cross correlation term, $2E_R E_S^* \cdot \cos(k \cdot d)$ can be expressed as:

$$S(k,z) = \int 2E_R(k') E_S^*(k') \cdot \cos(k' \cdot d) \cdot e^{-\frac{(k'-k)^2}{2u^2}} \cdot e^{-ik' \cdot z} dk'. \quad (13)$$

Note that $u$, the width or standard deviation of the Gaussian window, should be chosen carefully in order to obtain acceptable spectral or temporal resolution. If, for example, $u$ is chosen to be the same order of magnitude as the bandwidth of the source, then the STFT produces a TFD that has good temporal/depth resolution, but possibly poor spectral resolution. On the other hand, if $u$ is chosen to be much smaller than the bandwidth of the source, then the STFT generates a TFD with good spectral resolution, but possibly poor temporal resolution. The DW technique, however, can avoid this resolution tradeoff.

Consider the TFDs resulting from two STFTs, $S_1$ and $S_2$, generated by a narrow spectral window and a wide spectral window, respectively. Assuming that the reference field in Eq. (12) is slowly varying over the frequencies of interest, the processed signal is given by:

$$DW(k,z) = S_1(k,z) \cdot S_2^*(k,z) \quad (14)$$

$$= \int\int 4 E_S^*(k_1) E_S(k_2) \cdot \cos(k_1 \cdot d) \cos(k_2 \cdot d) \times$$

$$e^{-\frac{(k_1-k)^2}{2a^2}} \cdot e^{-\frac{(k_2-k)^2}{2b^2}} \cdot e^{-i(k_1-k_2)z} dk_1 dk_2,$$

where $a$ and $b$ are independent parameters that set the widths of the windows, and $b \gg a$. In order to obtain a more insightful form of the processed signal, consider a coordinate change such that:

$$\Omega = \frac{k_1 + k_2}{2}, \quad q = k_1 - k_2, \quad k_1 = \Omega + \frac{q}{2}, \quad (15)$$

and $$k_2 = \Omega - \frac{q}{2},$$

where the Jacobian of the transform is unity. Thus, the processed signal DW can be written as:

$$DW(k,z) = \quad (16)$$

$$\int\int 4 E_S^*\left(\Omega + \frac{q}{2}\right) E_S\left(\Omega - \frac{q}{2}\right) \cdot \cos\left(\left(\Omega + \frac{q}{2}\right) \cdot d\right) \cos\left(\left(\Omega - \frac{q}{2}\right) \cdot d\right) \times$$

$$e^{-\frac{(\Omega+\frac{q}{2}-k)^2}{2a^2}} \cdot e^{-\frac{(\Omega-\frac{q}{2}-k)^2}{2b^2}} \cdot e^{-iqz} d\Omega dq.$$

The term $$E_S^*\left(\Omega + \frac{q}{2}\right) E_S\left(\Omega - \frac{q}{2}\right)$$

from Eq. (16) can be expressed in terms of a Wigner TFD by utilizing the ambiguity function [12, 13]:

$$E_S^*\left(\Omega + \frac{q}{2}\right) E_S\left(\Omega - \frac{q}{2}\right) = \int W_S(\Omega, \zeta) \cdot e^{-iq\zeta} d\zeta, \quad (17)$$

where $W_S(\Omega, \xi)$ is the Wigner TFD of the sample field in the new coordinate system. After substituting Eq. (17) into Eq. (16) and simplifying, the processed signal yields:

$$DW(k,z) = \int\int\int 4 \cdot W_S(\Omega, \zeta) \cdot e^{-iq\zeta} d\zeta \cdot \cos(2\Omega \cdot d) \cos(q \cdot d) \times \quad (18)$$

$$e^{-((\Omega-k)+\frac{q}{2})^2 \cdot \left(\frac{1}{2a^2}+\frac{1}{2b^2}\right)+\frac{q(\Omega-k)}{b^2}} \cdot e^{-iqz} d\Omega dq.$$

By integrating Eq. (18) with respect to $q$ and assuming $a$ is small compared to $b$, such that $a^2/b^2 \ll 1$, the DW signal simplifies to:

$$DW(k,z) = \quad (19)$$

$$4b\sqrt{\pi} \int\int W_S(\Omega, \zeta) \cdot e^{-\frac{2(\Omega-k)^2}{b^2}} e^{-2(d+\zeta+z)^2 a^2} \cos(2\Omega \cdot d) \cdot d\Omega d\zeta.$$

Equation (19) shows that the DW technique is equivalent to probing the Wigner TFD of the sample field with two orthogonal Gaussian windows, one with a standard deviation of $b/2$ in the spectral dimension and another with a standard deviation of $1/(2a)$ in the spatial/temporal dimension. Furthermore, $a$ and $b$ independently tune the spectral and spatial/temporal resolutions, respectively, thus avoiding the tradeoff that hinders the STFT. Equation (19) also shows that the processed signal is modulated by an oscillation that depends on the constant path difference, d, between the sample and reference arms. This phenomenon is also observed in the cross terms of the Wigner TFD, which have been identified to contain valuable information about phase differences [12]. The utility of this oscillatory term is explored below.

Another interesting result is obtained if a approaches zero and b is taken to be much larger than the bandwidth of the source, Δk. In these limits, the window with standard deviation a→0 approaches the delta function, while the second window whose standard deviation b>>Δk, becomes a constant across the spectrum. If our signal F(k)=2$E_R E_S$·cos(k·d), and f(z)⇔F(k) is a Fourier transform pair, Eq. (14) yields:

$$DW(k, z)|_{a\to 0, b>>\Delta k} = S_1(k, z)|_{a\to 0} S_2(k, z)|_{b>>\Delta k} \quad (20)$$

$$= \frac{1}{\sqrt{2\pi}} f(z) F(k) e^{-ik\cdot z}.$$

Equation (20) is equivalent to the Kirkwood & Rihaczek TFD, and if the real part is taken, it is equal to the Margenau & Hill (MH) TFD [13]. Either of these two distributions can be simply transformed to produce any of the Cohen's class functions, such as the Wigner TFD [13].

DW Simulations

To illustrate the power of the DW technique, two different simulations are presented. In the first, a signal consisting of two optical fields separated in time and center frequency is simulated. The total sample field is given by $E_S = E_1 + E_2$, where $E_1 = E_0 \exp(-z^2)\exp(i \cdot k_1 \cdot z)$, $E_2 = E_0 \exp(-(z-z_0)^2)\exp(i \cdot k_2 \cdot z)$, and $k_1 > k_2$. The Wigner distribution of the total sample field is given by:

$$W(k, z) = \frac{1}{2\pi} \int E_S^*\left(z - \frac{\zeta}{2}\right) E_S\left(z + \frac{\zeta}{2}\right) e^{ik\zeta} d\zeta, \quad (21)$$

and the MH distribution of the total sample field is given by:

$$MH(k, z) = \text{Re} \frac{1}{\sqrt{2\pi}} \overline{E}_S(k) E_S(z) e^{-ikz}, \quad (22)$$

where $\overline{E}_s(k) \Leftrightarrow E_s(z)$ is a Fourier transform pair. FIGS. 16A-16D illustrate the resulting TFDs.

Figures 16A, 16B, 16C, 16D:
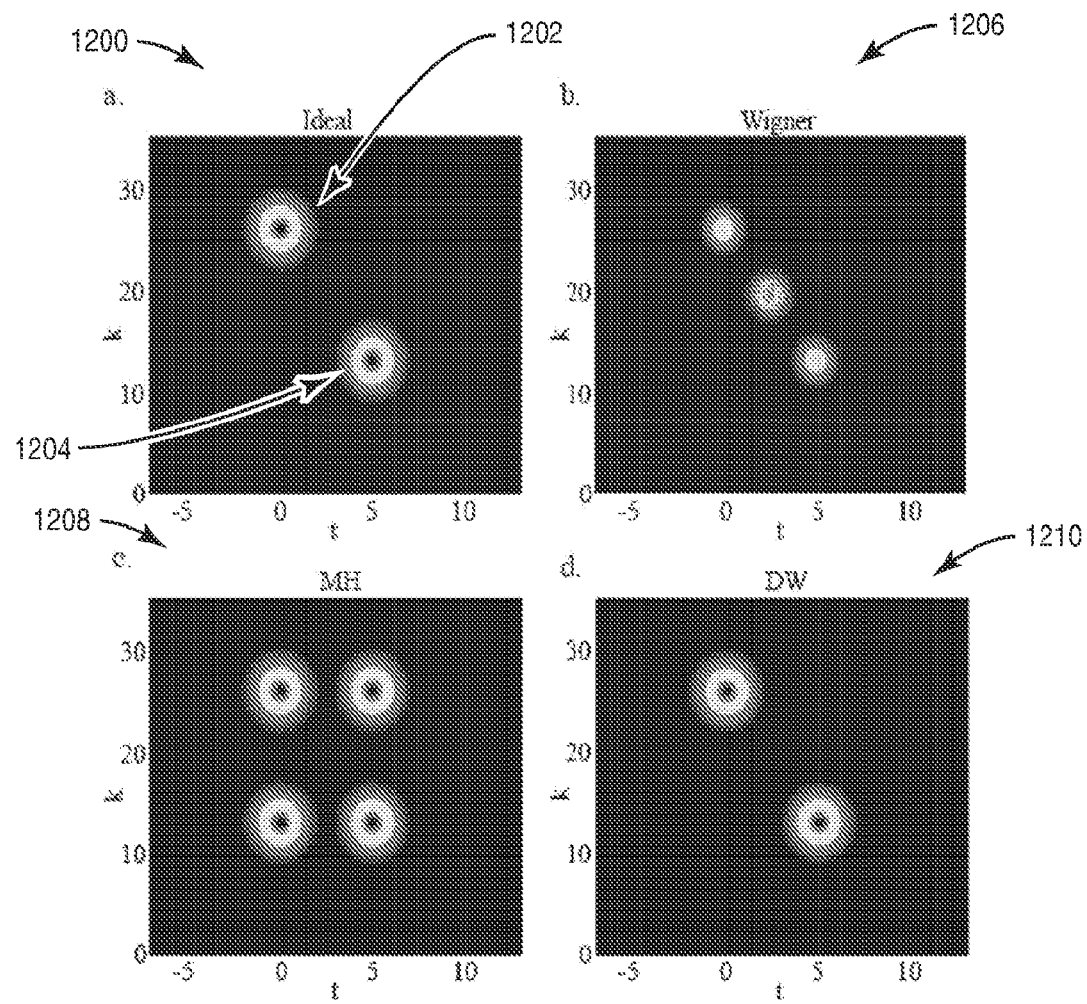
FIG. 16A shows an exemplary ideal time-frequency distribution (TFD) with $E_1$ centered at $z_0=5$ and $k_1=13$ and $E_2$ centered at $z_0=0$ and $k_2=26$ in a first simulation.
FIG. 16B shows an exemplary Wigner TFD in the first simulation.
FIG. 16C shows an exemplary MH TFD in the first simulation.
FIG. 16D shows the exemplary TFD generated using the Dual Window method in the first simulation.

An example ideal TFD 1200, shown in FIG. 16A, is produced by treating each pulse as an individual field and superimposing their respective TFDs onto one map. However, this can be obtained with prior knowledge of the individual fields. The ideal TFD 1200 in FIG. 16A contains two pulses 1202, 1204 with Gaussian shapes in both the temporal and spectral dimensions. The pulses 1202, 1204 are well separated in each dimension. FIGS. 16B-16D show different exemplary TFDs 1206, 1208, 1210 that can be generated from a single mixed field. The Wigner distribution 1206, shown in FIG. 16B, reveals the two Gaussian pulses along with an additional cross term that appears between them. The cross term contains modulations in each dimension which, in some cases, reveal important information about the temporal phase differences [12]. More often, however, these cross terms are viewed as undesirable artifacts as they yield non-zero values at times/depths and frequencies that do not exist in the field. Moreover, as more components are added to the field, the cross terms may interfere with the local signals.

The exemplary MH distribution 1208, shown in FIG. 16C, contains four pulses. In addition to the two pulses comprising the signal field, the MH TFD 1208 also contains two artifact pulses known as 'reflections in time' [13]. As is the case with the Wigner distribution, these artifacts yield non-zero intensities at times and frequencies that should contain no signal.

The TFD 1210 generated using the exemplary DW technique is presented in FIG. 16D. The exemplary TFD 1210 is generated by simply computing the product of two STFTs processed with wide and narrow spectral windows respectively. In FIG. 16D, the cross terms that are present in the Wigner and MH distributions 1206, 1208 are suppressed as a result of the use of two orthogonal windows.

The second simulation models a SOCT signal from a Michelson interferometer with an experimental sample containing two distinct reflecting surfaces. The first sample surface reflects the entire Gaussian spectrum of the source while the second sample surface absorbs the high frequency portion (upper half) of the source spectrum. This simulation is analogous to the absorbing phantom experiment discussed below. In the scenario of this simulation, i.e., a SOCT system, neither the Wigner nor the MH distributions can be constructed because the detected signal is the intensity of the field and therefore the phase information is lost. Thus, the TFDs are reconstructed in this example via the STFT and the DW technique.

Figures 17A, 17B, 17C, 17D, 17E, 17F:
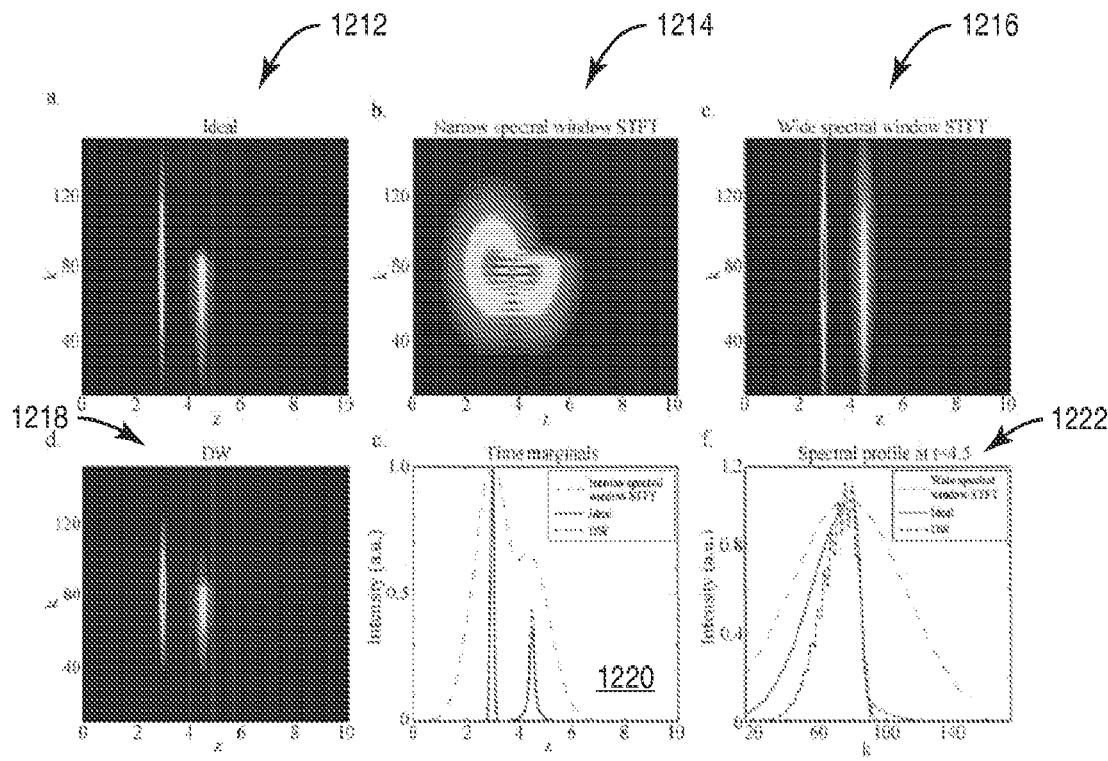
FIG. 17A shows an exemplary ideal TFD with simulated source bandwidth of $\Delta k=35$ length$^{-1}$ units in a second simulation modeling a SOCT signal from a Michelson interferometer.
FIG. 17B shows an exemplary TFD generated by a narrow spectral window STFT with standard deviation=2 length$^{-1}$ units in the second simulation.
FIG. 17C shows an exemplary TFTD generated by a wide spectral window STFT with standard deviation=45 length$^{-1}$ units in the second simulation.
FIG. 17D shows an exemplary TFD generated by using the double window method which computes the product of the TFDs shown in FIGS. 17B and 17C.
FIG. 17E shows exemplary time marginals (depth profile) computed from FIGS. 17A, 17B, and 17D.
FIG. 17F shows an exemplary spectral profile of the rear surface reflection in FIGS. 17B-17D illustrating that the DW technique maintains higher spectral fidelity.

FIG. 17A shows an exemplary ideal TFD 1212 of the simulated signal while FIGS. 17B and 17C show exemplary TFDs 1214, 1216 generated by the STFT using narrow and wide spectral windows, respectively. In each case, the effects of the time-frequency resolution tradeoff are obvious. The TFD generated with the wide spectral window suffers from degraded temporal resolution while the TFD generated with the narrow spectral window suffers from degraded spectral resolution. As Xu et al. showed, the STFT window can be optimized for specific applications, but regardless of the window size, a resolution tradeoff must be made [11]. FIG. 17D shows an exemplary TFD 1218 generated using the DW technique, which computes the product of the TFDs 1214, 1216 shown in FIGS. 17B and 17C. FIG. 17E shows exemplary time marginals 1220 computed from FIGS. 17B-17D, which demonstrate that the DW technique resolves the two sample surfaces with a resolution comparable to that of the ideal case, whereas the narrow spectral window STFT does not. FIG. 17F shows an exemplary spectral profile 1222 of the rear surface reflection in FIGS. 17B-17D illustrating that the DW technique maintains higher spectral fidelity than the wide spectral window STFT. Note that the DW technique is able to accurately portray the absorbed wavenumbers, while the wide spectral window STFT reveals no absorption information. The DW frequency profile also reveals the same spectral modulation that is seen in the narrow window STFT and that is characteristic of the Wigner TFD. This modulation results from cross correlations between field components that overlap in time and is analyzed further below.

Local Oscillations

It has been shown previously that temporal coherence information from Wigner TFD cross-terms can be utilized to gain structural knowledge of samples via the SOCT signal [12]. However, these cross terms are typically viewed as undesirable artifacts as they yield non-zero values at times/depths and frequencies that do not actually exist in the field.

Equation (19) shows that signals processed by the DW technique are modulated by a cosine term whose frequency depends on the constant path difference, d, between the sample and reference arms. This is the same phenomenon that is observed in the cross terms of the Wigner TFD, and these oscillations can be used to gain valuable information about phase differences.

Figures 18B, 18C:
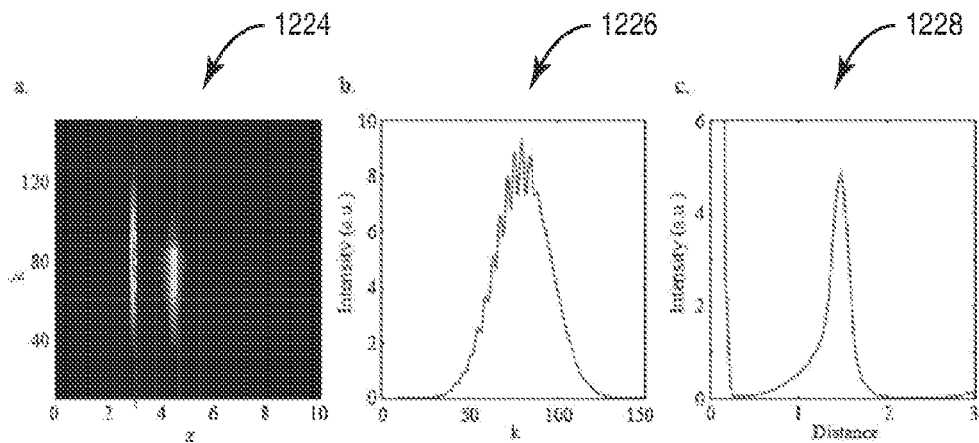
FIG. 18B shows an exemplary spectral profile from the front reflecting surface of the sample shown in FIG. 18A.
FIG. 18C shows an exemplary correlation plot with peak corresponding to sample spacing distance of 1.5 units.

FIG. 18B shows an exemplary frequency profile 1226 from the front reflecting surface of the sample in simulation 2 (FIGS. 17A-17F). This frequency spectrum is taken from depth 3 of a TFD 1224 shown in FIG. 18A, which was generated by the DW technique. The spectral modulation that is present can be further processed to reveal structural information about the simulated experimental sample. Fourier transforming the spectrum of the frequency profile 1226 from FIG. 18B generates a correlation plot 1228 shown in FIG. 18C, which exhibits a clear correlation peak corresponding to a physical distance of 1.5. This distance agrees with the 1.5 unit spacing of the surfaces in the simulated sample, thus providing additional information about the structure of the sample.

EXPERIMENTAL RESULTS

Absorption Phantom Experiments

Figures 19A, 19B, 19C:
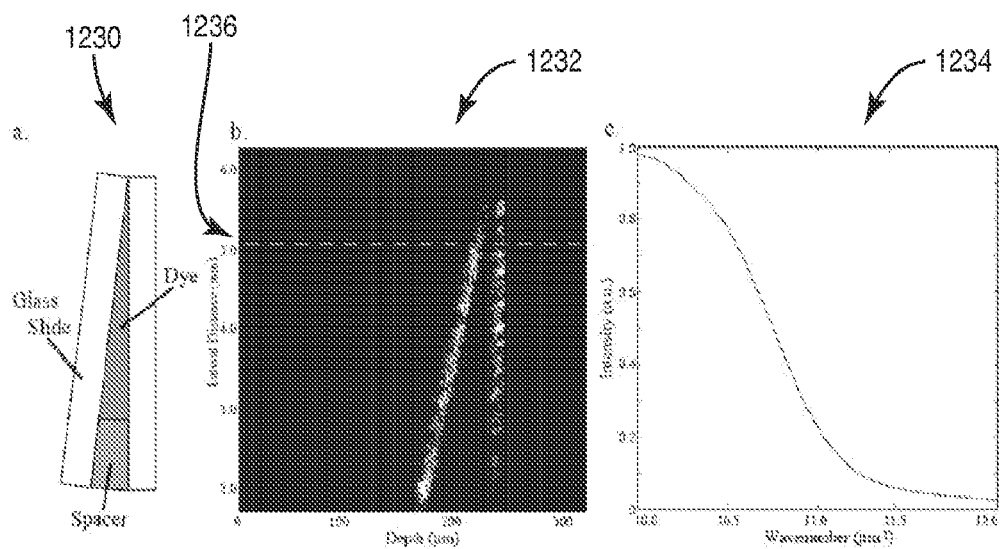
FIG. 19A is an illustration of an exemplary absorption phantom constructed of a glass wedge filled with an absorbing dye.
FIG. 19B shows an exemplary parallel frequency domain OCT (pfdOCT) image of the absorption phantom with the two inner glass surfaces clearly visible.
FIG. 19C shows an exemplary transmission spectrum of absorbing dye used in absorption phantom which shows strong absorption in the high wavenumber range of the detected spectrum.

Exemplary experiments were performed using the white light parallel frequency domain OCT (pfdOCT) system previously described by Graf et al. in [15]. To evaluate the ability of the DW processing method to generate TFDs with simultaneously high spectral and temporal resolution, an absorption phantom is constructed consisting of a glass wedge filled with an absorbing dye 1230, as shown in FIG. 19A. FIG. 19B shows an exemplary pfdOCT scan 1232 of the absorption phantom with the two inner glass surfaces clearly visible. Note that the signal from the rear surface is significantly attenuated at the thicker end of the wedge due to considerable signal absorption due to the greater volume of absorbing dye present. Because the experimental system operates in the visible wavelength band, a visible absorbing dye consisting of a red food-coloring gel and water solution could be used. FIG. 19C shows a transmission spectrum 1234 of the absorbing dye, which shows strong absorption in the high wavenumber range of the detected spectrum. One would expect signals returning from the front surface of the phantom to exhibit a relatively flat spectrum, while signals reflected by the back surface of the phantom would exhibit spectra with significant attenuation of the higher wavenumbers, mirroring the absorption spectrum of the dye through which it passed.

Figures 20A, 20B, 20C, 20D:
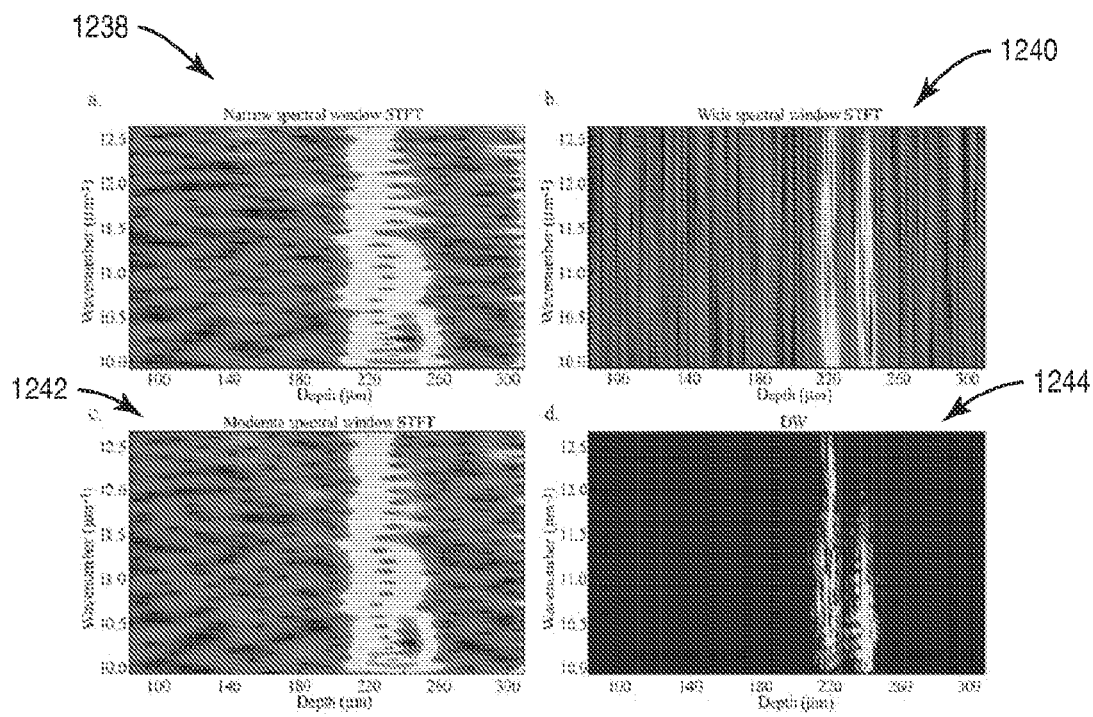
FIG. 20A illustrates an exemplary TFD of the absorption phantom generated by a narrow spectral window STFT.
FIG. 20B illustrates an exemplary TFD of the absorption phantom generated by a wide spectral window STFT.
FIG. 20C illustrates an exemplary TFD of the absorption phantom generated by a moderate spectral window STFT.
FIG. 20D illustrates an exemplary TFD of the absorption phantom generated by the dual window technique.

The raw data corresponding to the position of an exemplary dashed red line 1236 in FIG. 19B was processed with four different methods to yield the four TFDs shown in FIGS. 20A-20B. FIG. 20A was generated using the exemplary STFT processing method with a narrow spectral window of 0.0405 $\mu m^{-1}$. A resulting exemplary TFD 1238 has excellent spectral resolution, showing a relatively flat spectrum across all wavelengths at the depth corresponding to the front surface of the phantom. The sharp spectral cut-off at high wavenumbers, characteristic of the dye absorption, is evident at deeper depths. However, the narrow spectral window used to generate this TFD yields very poor temporal resolution, resulting in an inability to resolve the two surfaces of the phantom. FIG. 20B was also processed using the exemplary STFT method, but in this case a wide spectral window of 0.665 $\mu m^{-1}$ was used. A resulting TFD 1240 has excellent temporal resolution, clearly resolving the two surfaces of the phantom. However, the spectral resolution of the resulting TFD is too poor to resolve the spectral modulation expected for the rear surface spectrum. FIG. 20C shows the exemplary TFD generated using the STFT method with a window of moderate spectral width, 0.048 $\mu m^{-1}$. As expected, the spectral and temporal resolutions of a resulting TFD 1242 fall between those of FIGS. 20A and 20B, illustrating the temporal-spatial resolution tradeoff associated with the STFT processing method. While the spectral characteristics of the absorbing dye are apparent in this TFD, the two phantom surfaces still cannot be resolved.

An exemplary TFD 1244 in FIG. 20D was generated using the DW technique. By processing the raw data with both a narrow and a wide spectral window, the TFD simultaneously achieves high spectral and temporal resolution. The front phantom surface exhibits a relatively flat spectrum across all wavelengths while the rear surface spectrum clearly reveals a spectral cutoff at high wavenumbers due to the absorbing dye through which the signal field has passed. Additionally, the front and back surfaces of the phantom are clearly resolved in depth.

Figures 21A, 21B, 21C:
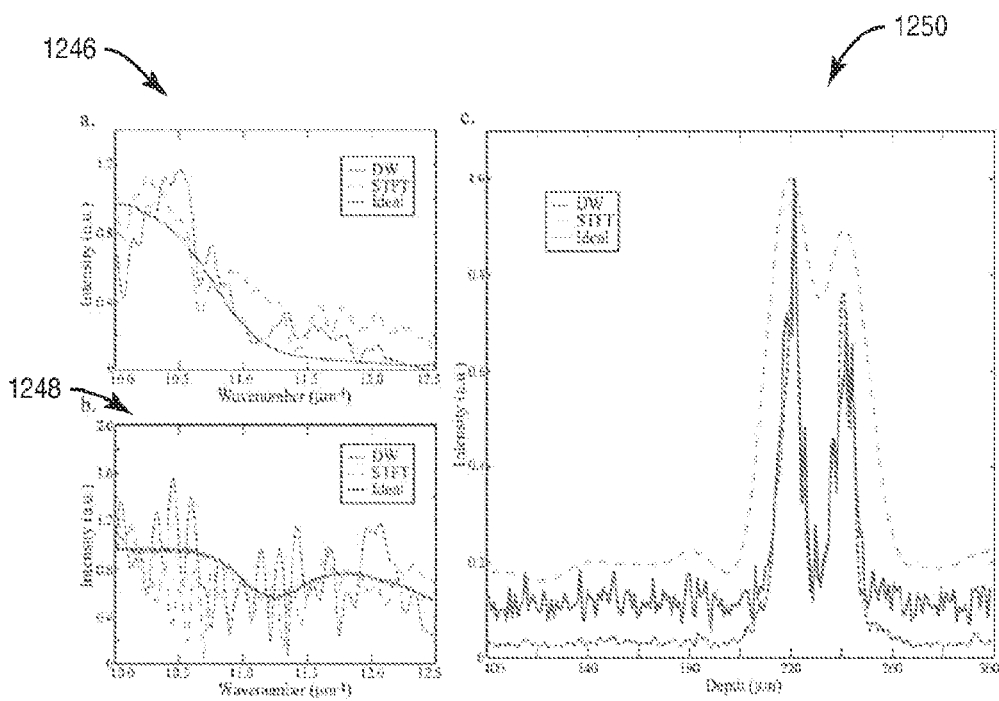
FIG. 21A displays exemplary spectral profiles from depths corresponding to the absorption phantom's rear surface in the TFDs of FIGS. 20C and 20D.
FIG. 21B shows exemplary spectral cross-sections from depths corresponding to the absorption phantom's front surface, along with the source's reflectance spectrum for reference.
FIG. 21C displays an exemplary time marginals for each TFD from FIGS. 20C and 20D, along with the corresponding A-scan from FIG. 19B.

The utility of the DW processing method is further demonstrated by examining spectral cross-sections and time marginals of the generated TFDs. FIG. 21A displays exemplary spectral profiles 1246 from depths corresponding to the absorption phantom's rear surface in the TFDs 1242, 1244 of FIGS. 20C and 20D. For reference, the absorbing dye transmission spectrum is displayed as well. FIG. 21B shows exemplary spectral cross-sections 1248 from depths corresponding to the phantom's front surface, along with the phantom's reflectance spectrum for reference. Exemplary time marginals 1250 of each TFD 1246, 1248 are displayed in FIG. 21C along with the corresponding A-scan from FIG. 19B. It is evident that the TFD generated by the DW technique maintains the ability to resolve the two peaks of the absorption phantom, while the TFD generated by the STFT method does not.

Figures 22A, 22B:
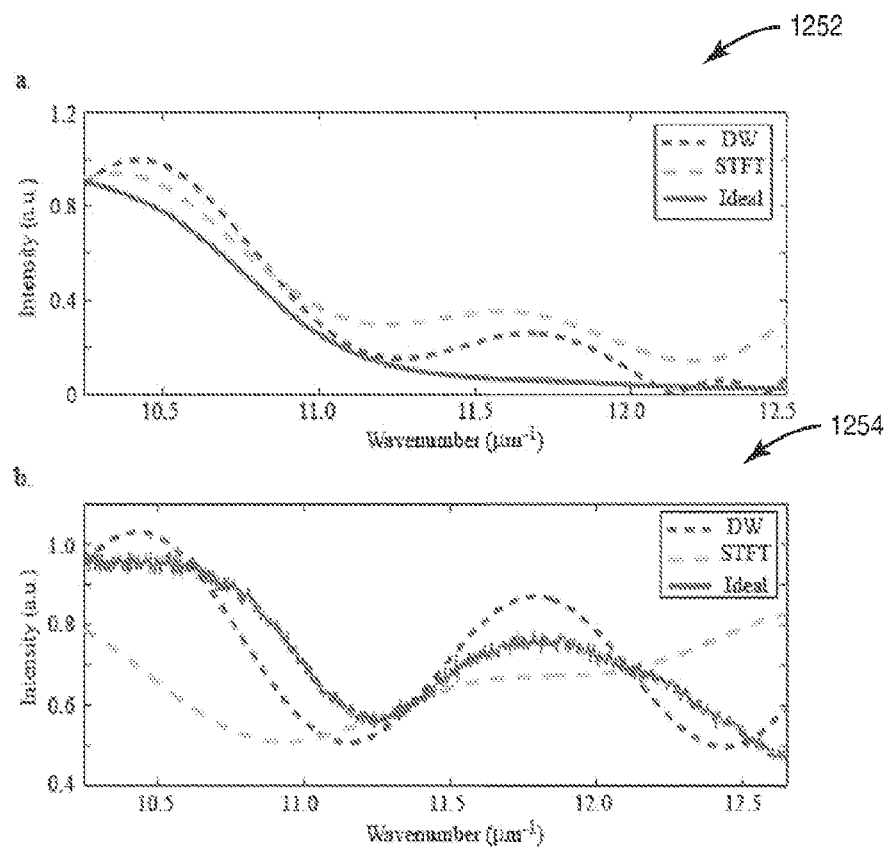
FIG. 22A shows exemplary spectral profiles of FIG. 21A with high frequency modulations removed.
FIG. 22B shows exemplary spectral profiles of FIG. 21B with high frequency modulations removed.

In addition to limiting the resolution tradeoff associated with the STFT, the exemplary DW technique also achieves an increase in the spectral fidelity of generated TFDs. The exemplary normalized spectra from FIGS. 21A and 21B are plotted in FIGS. 22A and 22B with the high frequency modulation removed by a low-pass filter. By separating the low frequency content from the high frequency local oscillations, one can assess the fidelity with which each processing method recreates the ideal spectrum. Chi-squared values for each processing method were calculated to assess goodness-of-fit. Table 1 below summarizes exemplary chi-squared values. For both exemplary rear surface spectra 1252 in FIG. 22A and front surface spectra 1254 in FIG. 22B, the chi-squared values associated with the DW technique are lower than those of the STFT indicating that the DW processing method recreates the ideal signal with greater spectral fidelity. In addition, the goodness of fit for the square of the STFT is calculated in this example to account for the fact that the DW technique produces a bi-linear distribution. The exemplary DW technique is also seen to produce superior spectral fidelity than the STFT squared.

TABLE 1

Chi-squared calculations

|  | DW | STFT |
|---|---|---|
| Rear surface spectrum | 0.0980 | 0.1329 |
| Front surface spectrum | 0.0248 | 0.0305 |

Figures 23A, 23B, 23C:
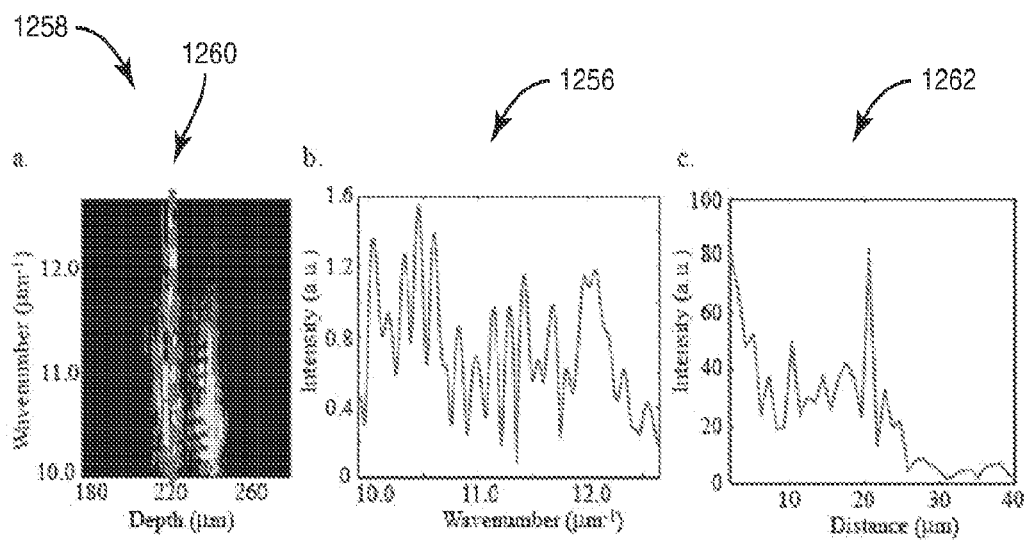
FIG. 23A illustrates an exemplary absorption phantom TFD generated with the DW technique.
FIG. 23B shows an exemplary spectral profile from the front surface of the absorption phantom corresponding to the dashed line in FIG. 23A.
FIG. 23C shows an exemplary correlation plot with peak corresponding to phantom spacing distance that is in good agreement with the OCT thickness measurement.

As with the simulated SOCT signals, the local oscillations seen in the TFD obtained from probing the absorption phantom (FIGS. 22A and 22B) can also be analyzed to gain structural information about the experimental sample. FIG. 23B shows exemplary spectral profile 1256 from the front surface of an absorption phantom 1258 indicated by a dashed red line 1260 in FIG. 23A. Fourier transforming this spectrum produces an exemplary correlation plot 1262 as shown in FIG. 23C with a clear correlation peak corresponding to a physical distance of 20.60 µm. This measurement represents the spacing between the phantom surfaces and is in excellent agreement with the spacing measured in the OCT image of the phantom, 20.60 µm±5.97 µm. Here the measurement uncertainty is larger than the 1.22 µm depth resolution due to the fact that the glass surface was slightly abraided to increase the signal, producing a broader range of path lengths.

Animal Tissue Experiments

To show the utility of the DW technique for processing SOCT and fLCI signals from biological samples, the pfdOCT system was applied in this example to capture spectra from ex vivo hamster cheek pouch epithelial tissue. The tissue sample was freshly excised and placed between two coverglasses prior to scanning. Data was collected without the need for any fixation, staining, or further preparation of the tissue. The raw data was processed using the DW technique and resulted in an exemplary TFD 1264 shown in FIG. 24A.

Figures 24A, 24B, 24C:
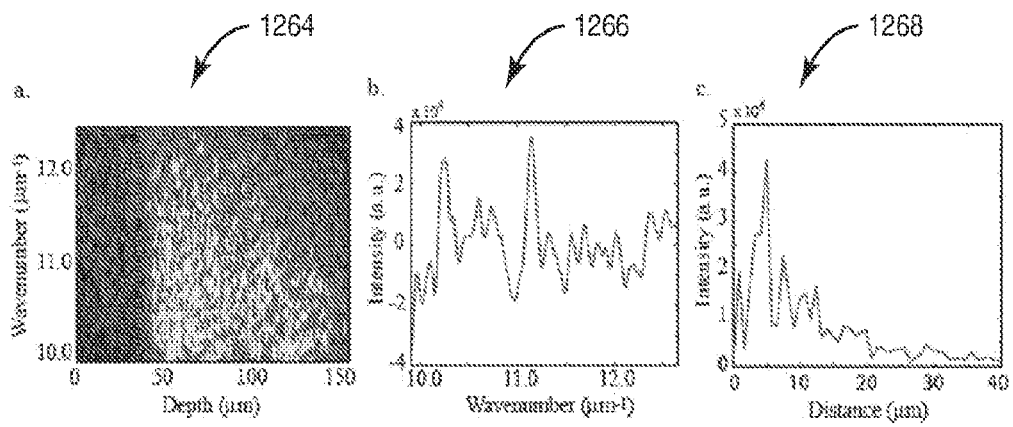
FIG. 24A shows an exemplary TFD from hamster cheek pouch tissue generated with the DW technique.
FIG. 24B shows an exemplary average spectrum from a 15 µm depth segment corresponding to the basal tissue layer.
FIG. 24C shows an exemplary correlation plot with peak corresponding to scatterer diameter of 4.94 µm.

The generated TFD can be used to identify spectral modulation due to scattering within the sample, specifically to assess nuclear morphology in situ based on scattering signatures. In epithelial tissues, the majority of nuclear scattering occurs in the basal layer, approximately 40 µm beneath the tissue surface, as determined by histopathological analysis. The corresponding depth of the exemplary TFD 1264 in FIG. 24A was selected and the spectra from 15 adjacent lines were averaged in order to increase the signal-to-noise ratio. The averaged spectrum was first fit by a power-law and an exemplary residual spectrum 1266 is shown in FIG. 24B. The local oscillations present in this signal contain valuable structural information about the scatterers in the tissue. It has been previously shown that these local oscillations can be used to quantitatively determine nuclear morphology by analyzing the Fourier transform of the spectrum, producing a plot of the depthwise correlation function [8]. Upon Fourier transforming the exemplary residual spectrum 1266 from FIG. 24B, a correlation plot 1268 shown in FIG. 24C is obtained, showing a clear correlation peak corresponding to a mean scatterer diameter of 4.94 µm. This diameter corresponds nicely with the nuclear diameter expected for the basal tissue layer of hamster cheek pouch epithelium.

In summary, the exemplary DW techniques disclosed herein may be used for processing SOCT signals and can simultaneously maintain high spectral and temporal resolution. Moreover, the nature of SOCT signals provides a well-conditioned and optimal problem for the DW technique, even though it is expected that this approach may break down for signals with sharply varying frequency content, such as those due to a chirped pulse. It has been shown that the DW techniques probe the Wigner TFD of the signal field with two orthogonal windows that independently determine spectral and temporal resolution and thus avoid the resolution tradeoff that hinders traditional SOCT and fLCI processing methods. In addition, it has been shown that local oscillations contained in the TFDs generated by the DW technique contain valuable information about the structure of experimental samples. By comparing the performance of the DW and STFT processing methods in analyzing SOCT signals from an absorption phantom, it has been shown that the DW technique recovers TFDs with superior fidelity while simultaneously maintaining high spectral and temporal resolution. It has also been shown the utility of the DW technique for processing SOCT and fLCI signals from biological samples to gain morphological information about scatterers.

Since its introduction, SOCT has held promise for gaining spatial and functional knowledge of a biological sample by mapping spectral information onto depth resolved images. Unfortunately, traditional SOCT processing methods such as the STFT and CWT have been limited by an inherent tradeoff between spectroscopic and depth resolution. This time-frequency tradeoff greatly reduces the utility of the analysis by degrading either the depth or spectral resolution to the point that important features cannot be accurately reconstructed. It is expected that by avoiding this tradeoff, the DW processing method will enable new directions in SOCT and depth resolved spectroscopy.

The exemplary DW techniques disclosed herein have been used to process measurements of morphological features in a thick turbid sample using light scattering spectroscopy (LSS) and Fourier-domain low coherence interferometry (fLCI). A parallel frequency domain optical coherence system with a white light source is used to image a two-layer phantom containing polystyrene beads of diameters 4.00 µm and 6.98 µm on the top and bottom layers, respectively. The DW technique decomposes each OCT A-scan into a time-frequency distribution with simultaneously high spectral and spatial resolution. The spectral information from localized regions in the sample is used to determine scatterer structure. The results show that the two bead populations can be accurately and precisely differentiated using LSS and fLCI.

Light scattering spectroscopy (LSS) [17] has served as one exemplary foundation for a number of technologies including Fourier-domain low-coherence interferometry (fLCI) [18], which has been developed to measure the enlargement of epithelial cell nuclei associated with precancerous development [19]. In fLCI, depth resolution is obtained by coherence gating with spectral information acquired using a short time Fourier transform (STFT). This process is similar to what is done in spectroscopic optical coherence tomography (SOCT) [20]. However, in fLCI, after processing with a STFT, the spectrum from a given depth is quantitatively analyzed to determine the size of scattering objects [18].

SOCT, an extension of optical coherence tomography, provides the same cross-sectional tomographic imaging capabilities of OCT [21] with the added benefit of spectroscopic based contrast [20]. As described above, SOCT uses STFTs or wavelet transforms to obtain spectroscopic information, which provides additional information about a sample. Unfortunately, the windowing process of STFTs introduces an inherent trade off between spatial and spectral resolution, which limits further quantitative processing of the depth resolved spectra. The dual window (DW) method for processing SOCT signals achieves both high spectral and spatial resolution, allowing for a more thorough quantitative treatment of the depth resolved spectral information [22].

Morphological measurements of different populations of scatterers in a turbid medium may be processed with the DW technique, and analyzed with LSS and fLCI techniques. The DW technique decomposes each depth resolved A-scan from the OCT signal into a time-frequency distribution (TFD), which inherently aligns the quantitative spectral analysis with the OCT image to determine the local scatterer structure. The approach is demonstrated through imaging and analysis of a two-layer phantom, with each layer containing a suspension of different size polystyrene beads.

A white light parallel frequency domain OCT system, as described by Graf et al [23], can be used. In short, a Michelson interferometer geometry can be modified with four additional lenses, to form a 4F imaging system, thereby limiting the number of spatial modes illuminating the sample and reference arm. In this example, the light returned by the two arms are combined and imaged onto the entrance slit of an imaging spectrograph. The interference signal is obtained in parallel across one dimension comprising 150 spatial lines and spanning 3.75 mm. The spectrograph can disperse each channel into its wavelength components, where a 150 nm bandwidth centered at $\lambda_0=550$ nm is analyzed, yielding an axial resolution of 1.22 µm. The spectrograph may be configured to disperse each channel into color channels, such as for red, green, and blue wavelength components that can be used to display information using RGB values on an RGB display To process the OCT image, six steps can be taken as an example. 1. The sample and reference arm intensities are acquired separately and subtracted from the signal. 2. The resulting interferometric signal is divided by intensity of the reference field to normalize for the source spectrum and detector efficiencies as a function of λ. This step is of particular importance for quantitative comparison of depth resolved spectra, since the remaining spectral dependence is assumed to arise solely from absorption of forward scattered light and scattering cross sections of backscattered light. 3. The data are re-sampled into a linear wave-number vector, $k=2\pi/\lambda$. 4. Chromatic dispersion is digitally corrected. 5. A fast Fourier transform is executed to obtain an A-scan, and 6. The process can be repeated for each of the 150 spatial lines to obtain the OCT image.

Similar to the generation of the OCT image, the exemplary DW technique can use the interferometric information and provide exemplary steps 1-4, as described above. As a last step, a product of two STFTs is taken: one STFT with a narrow window for high spectral resolution and another with a wide window for high spatial resolution. Eq. 23 describes the distribution obtained with the exemplary DW technique from a single spatial line, $$DW(k,z) = \int 2\langle E_S \rangle \cos(\kappa_1 \cdot \Delta OPL) e^{-\frac{(\kappa_1-k)^2}{2a^2}} e^{-i\kappa_1 z} d\kappa_1 \times \int \left( 2\langle E_S \rangle \cos(\kappa_2 \cdot \Delta OPL) e^{-\frac{(\kappa_2-k)^2}{2b^2}} e^{-i\kappa_2 z} \right)^* d\kappa_2, \quad (23)$$

where z is the axial distance, and a and b are the standard deviations of the windows. Robles et al. have shown that the DW, a product of two linear operations, can be described by Cohen's class bilinear functions [22]. With b>>a, the DW samples the Wigner TFD with two orthogonal windows that are independently set by the parameters a and b, resulting in suppression of many common artifacts.

The exemplary DW contains two components that relay information, which are analyzed independently in this example. The first component, contained in the low frequencies of the DW(k, $z_0$), corresponds to the spectral dependence of the optical signal at $z_0$ and arises from absorption and scattering in the sample. This component is analyzed with LSS. The second component is the morphological features about $z_0$, arising from the temporal coherence of the scattered light and contained in the local oscillations (high frequencies) of the signal [22]. This is analyzed with fLCI.

Figures 25A, 25B:
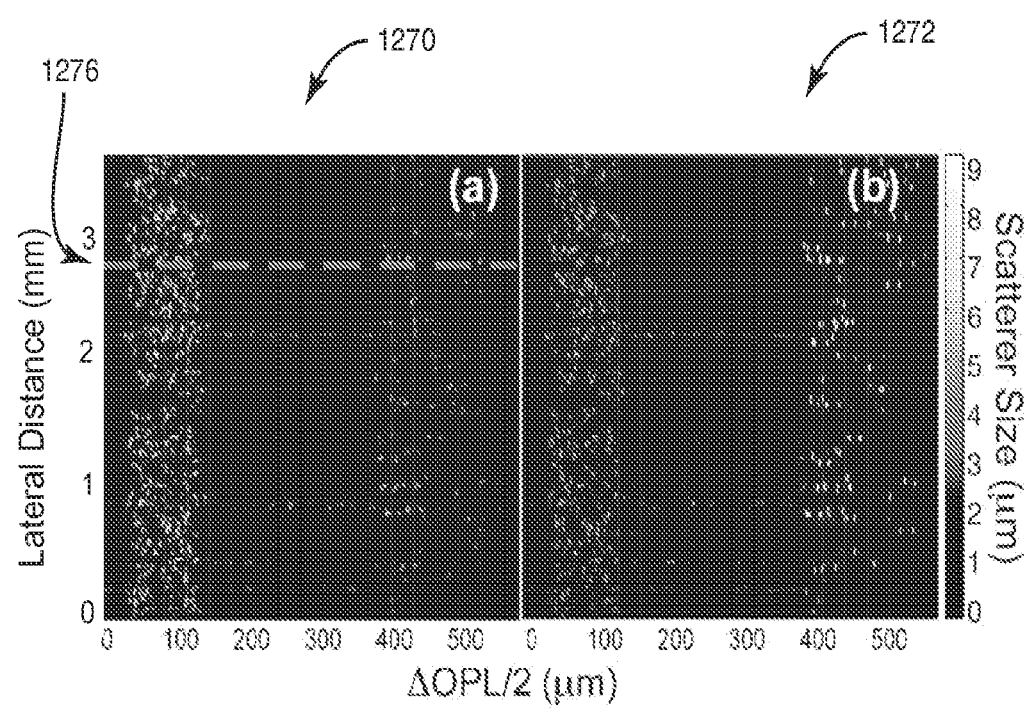
FIGS. 25A and 25B show an exemplary OCT image of a phantom acquired by a single 0.3 second exposure with no scanning.

This study seeks to analyze scattering structures in a thick turbid sample using LSS and fLCI methods. Thus, a two-layer phantom containing polystyrene beads ($n_b=1.59$) of different sizes (d=6.98 µm and 4.00 µm in top and bottom layers respectively) suspended in a mixture of Agar (2% by weight) and water, with $n_a=1.35$, is used. The scatterer concentration is chosen to yield a mean free scattering path length of $l_s=1$ mm to ensure sufficient SNR at deeper depths. FIG. 25A shows an OCT image 1270 of the phantom acquired by a single 0.3-sec exposure, with no scanning needed.

Figures 26A, 26B:
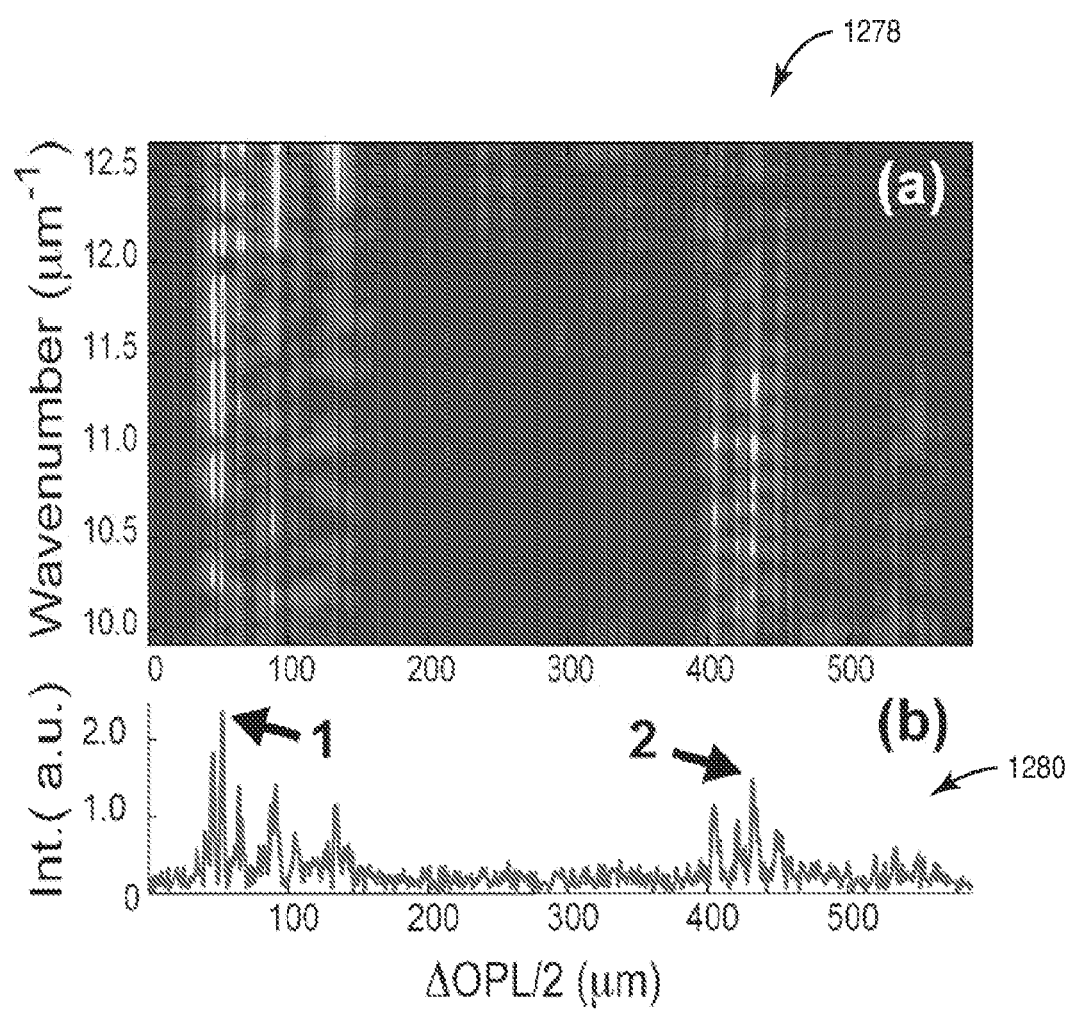
FIG. 26A shows an exemplary processed TFD of the image in FIGS. 25A and 25B using the DW technique.
FIG. 26B shows an exemplary corresponding A-scan to the TFD of FIG. 26A.
Figures 27A, 27B, 27C, 27D:
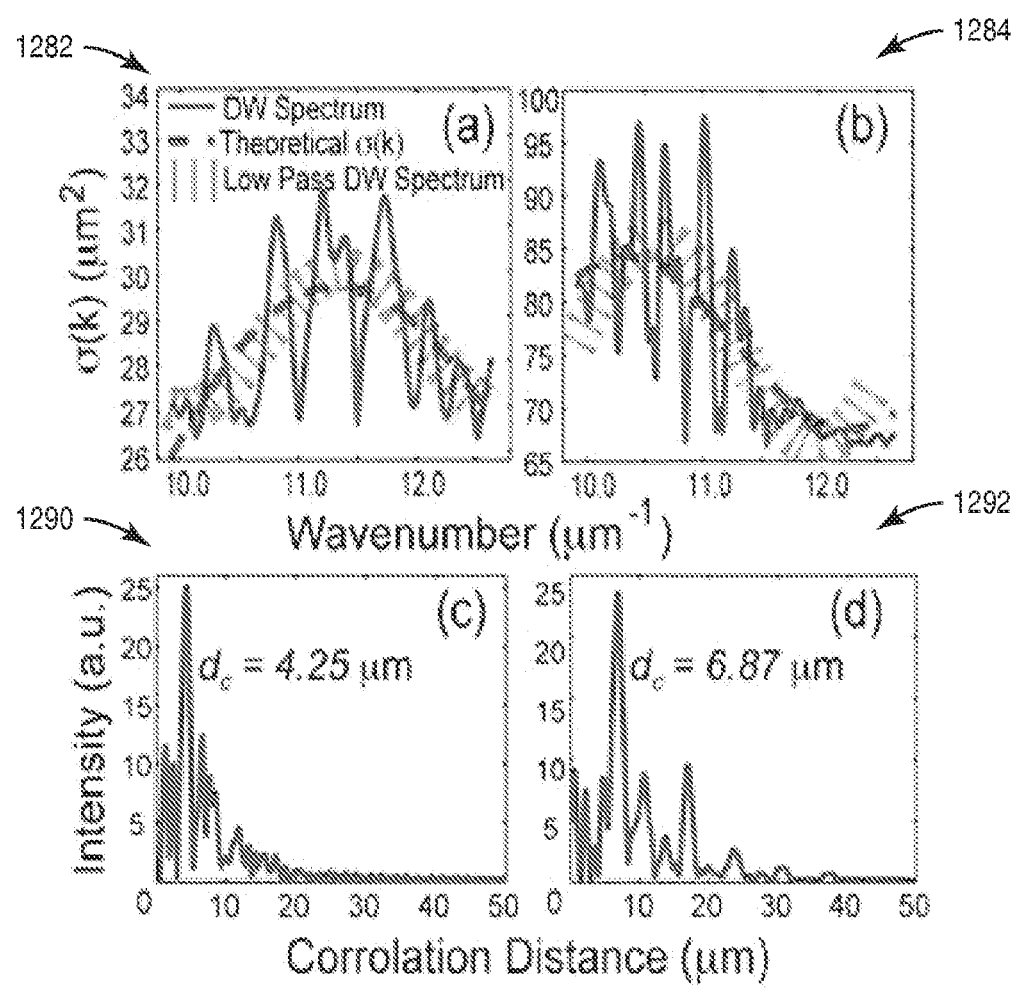
FIGS. 27A and 27B show exemplary spectral profiles of two points from the A-scan of FIG. 26B.
FIGS. 27C and 27D show exemplary correlation plots for the two points from the A-scan of FIG. 26B.

The exemplary DW technique can be used to calculate a TFD for each lateral line, yielding a spectrum for each point in the OCT image with high spectral and spatial resolution (DW parameters set to a=0.0454 µm$^{-1}$ and b=0.6670 µm$^{-1}$). FIG. 25B shows a processed TFD 1272 of a representative line 1276 (dashed red line in FIG. 25A), with a corresponding A-scan 1280 (FIG. 26B). Two representative points are selected and the spectrum from each is analyzed as an example. FIGS. 27A and 27B give spectral profiles 1282, 1284 (solid blue lines) from points 1 and 2, respectively.

The low frequencies of the depth resolved spectra contain information about absorption and scattering cross sections in this example. Since no chromophores are present, the spectral dependence gives the scattering cross section of the beads; thus, the Van de Hulst approximation [24] can be used to determine the bead size. To achieve this, the DW spectral profile is low-pass filtered with a hard cut off frequency of 3.5 µm (three cycles); then, a least-squares fit is used to obtain the scatterer diameter. In FIGS. 27A and 27B, dotted green lines 1286, 1288 show the low pass filtered data used for fitting, which yield $d_1=3.97$ µm and $d_2=6.91$ µm for points 1 and 2, respectively, in good agreement with the true bead sizes. The dashed red line gives the theoretical scattering cross section corresponding to the best fits: note that these are in excellent agreement with the processed signals.

The high frequency components of DW(k,$z_0$) in this example give the fLCI measurement. First, the spectral dependence is removed by subtracting the line of best fit from the analysis above. Then, the residuals are Fourier transformed to yield a correlation function where the maxima give the distance between dominant scattering features in the analyzed region. For the bead phantom, the local oscillations predominately result from scattering by the front and back surfaces. Further, simulated OCT images by Yi et al., show that a single microsphere gives rise to multiple peaks [25] which are also taken into account. FIGS. 27C and 27D plot a correlation function 1290, 1292 for points 1 and 2 respectively, giving correlation peaks at $d_c=\Delta OPL/(2n_b)=4.25$ µm and 6.87 µm, in good agreement with both the LSS measurements and true bead sizes.

The procedure in this example was repeated for all points in the OCT image, where an automated algorithm selected peaks that were above a threshold (int.>100) and 10% higher than other maxima in the correlation function. Further, only points where the LSS and fLCI measurements were in agreement within the system's resolution (±1.22 µm) were considered. FIG. 25B shows an overlay 1272 of the fLCI measurements with the OCT image. In the top layer, the average scatterer size was 3.82±0.67 µm and 3.68±0.41 µm for the fLCI and LSS measurements, respectively, with 82% agreement (112 points). In the bottom layer, the average scatterer size was 6.55±0.47 µm and 6.75±0.42 µm for fLCI and LSS, respectively, with a lower 35% agreement (113 points) due to the lower SNR at the deeper sample depth. These results show that by utilizing two independent methods to analyze scattering structure (fLCI and LSS), our technique yields accurate and precise measurements throughout the whole OCT image.

Sources of error for the fLCI measurement can arise due to partial volume effects where multiple beads lie within a single pixel region (25 μm×1.15 μm) giving multiple maxima in the correlation function.

In summary, accurate measurements of morphological features with wavelength precision using LSS and fLCI by processing with the exemplary DW technique have been achieved. Recently, Yi et al. presented results that use a similar optical system and STFT processing to discriminate fluorescent and non-fluorescent microspheres in a weakly scattering medium [25]. The Yi et al. analysis was restricted to a thin (<100 μm) layer and did not assess structure, as they intentionally discarded the high frequency spectral modulations due to the scatterer's structure (i.e. diameter). In comparison, the results presented here confirm the potential to measure enlargement of epithelial cell nuclei, which are non-absorbing, to detect precancerous development within intact tissues.

The novel dual window approach disclosed herein has also been used for spectroscopic OCT measurements and applied to probe nuclear morphology in tissue samples drawn from the hamster cheek pouch carcinogenesis model. The dual window approach enables high spectral and depth resolution simultaneously, allowing detection of spectral oscillations which are isolated to determine the structure of cell nuclei in the basal layer of the epithelium. The measurements were executed with our parallel frequency domain OCT system which uses light from a thermal source, providing high bandwidth and access to the visible portion of the spectrum. The structural measurements show a highly statistically significant difference between untreated (normal) and treated (hyperplastic/dysplastic) tissues, indicating the potential utility of this approach as a diagnostic method.

Cancers typically develop slowly over time, beginning with just a few abnormal cells that grow and proliferate. The majority of malignancies develop through precancerous states characterized by varying levels of architectural and cytologic abnormality. [27] Detecting these structural changes in tissues at the earliest possible stages could provide an increased opportunity for therapeutic intervention and thus, greatly reduce rates of mortality and morbidity. However, detecting precancerous development is a great challenge for available screening techniques.

The current "gold standard" for detecting cancer of epithelial tissues is the histopathologic analysis of biopsy samples. Biopsy samples are excised from the tissue under examination and then fixed, sectioned, stained, and ultimately examined by a pathologist for morphological abnormalities. Although this procedure is the standard practice for cancer diagnosis, there are several drawbacks to this approach, including the subjectivity of diagnoses, the inherent invasiveness of biopsies, the time delay between biopsy and diagnosis, and the poor coverage of at-risk tissue.

It is clear that improved screening and diagnostic technologies are needed to overcome these limitations. In recent years, large amounts of research have focused on developing optical methods for early cancer detection [28-30] because such methods hold great promise to overcome the limitations of the traditional biopsy listed above. One specific technique, elastic light scattering spectroscopy, is an optical technique that analyzes scattered light to obtain information about the structures with which the light interacts. For decades, elastic light scattering has been utilized in a variety of applications where direct measurement of physical properties is impractical or impossible. Most recently, advances in biophotonics have enabled application of elastic light scattering to biology and medicine. Using powerful, broadband light sources, elastic scattering spectroscopy (ESS) has been used by several groups to investigate the cellular morphology of in vivo and ex vivo tissue samples [31-34]. Because enlargement of the nuclear diameter is a key indicator of precancerous growth [27], the morphology of the cell nucleus has become a strategic target for light scattering studies.

These advancements have paved the way for an elastic light scattering technique known as Fourier domain low coherence interferometry (fLCI) [35, 36]. The fLCI approach uses interferometry to obtain depth-resolved spectroscopic information which can then be analyzed to recover structural information, such as nuclear morphology, from specific layers in a sample. For early cancer detection, fLCI may be applied to detect enlargement of nuclear diameter which can serve as a biomarker of precancerous transformation. This biomarker, either alone or in conjunction with other information derived from the light scattering signal, can provide the quantitative information necessary to distinguish between normal and dysplastic epithelial tissue with high sensitivity and specificity.

The results of the first study assessing the ability of the fLCI technique to distinguish between normal and dysplastic ex vivo epithelial tissues is hereby presented. In the study, quantitative nuclear morphology measurements are used as a biomarker to distinguish between normal and dysplastic hamster cheek pouch epithelium.

Materials and Methods

Animal Model

The animal study was completed using the hamster cheek pouch carcinogenesis model. For the animal study, all experimental protocols were approved by the Institutional Animal Care and Use Committees of Duke University and North Carolina Central University and in accordance with the National Institutes of Health (NIH). Male Syrian golden hamsters, six weeks of age, were obtained from Harlan Laboratories (Indianapolis, Ind.) and housed at North Carolina Central University. The animals were housed four per cage in a room with controlled temperature and humidity and in a twelve hour light/dark cycle. Regular cage changes ensured maintenance of hygienic conditions. All animals were given the AlN-93M diet (Research Diets, New Brunswick, N.J.). The diet consisted of 14% casein, 0.18% 1-cystine, 49.5% corn starch, 12.5% maltodextrin 10, 10% sucrose, 5% cellulose, 4% soybean oil, 0.0008% t-Butylhydroquinone, 3.5% mineral mix, 1% vitamin mix, and 0.25% choline bitartrate. Tap water was available ad libitum. After an acclimatization period of one week, the left cheek pouch of each animal was topically treated with 100 μl of 0.5% 7,12-dimethylbenz[a]anthracene (DMBA) (Sigma Chemical Company, St. Louis, Mo.) in mineral oil with a paintbrush three times per week for six weeks. The right cheek pouch was left untreated and served as the control group.

Experimental Protocol

At 24 weeks after the initial treatment of DMBA, the hamsters were shipped to Duke University for optical spectroscopic analysis. The hamsters were euthanized by $CO_2$ asphyxiation before being subjected to gross necropsy. The entire left and right cheek pouches were excised and cut into two pieces. The samples were laid flat between two coverglasses, moistened with PBS, and immediately scanned by the parallel frequency domain optical coherence tomography (pfdOCT) system. Following the optical measurements, scanned areas were marked with India ink and the tissue samples were fixed in 10% PBS buffered formalin. The fixed samples were later embedded in paraffin, sectioned, and stained with hematoxylin and eosin (H&E) for histopathological analysis.

The complete animal trial analyzed tissue samples from 21 hamsters. Although one treated and one untreated sample was extracted from each animal and scanned by the fLCI system, only 16 of 21 untreated samples were used in the study. The signal-to-noise ratio of the scans from the remaining five untreated samples was insufficient to provide useful data. Therefore, these scans were not included in the spectroscopic analysis.

Parallel Frequency Domain Optical Coherence Tomography

Figure 28:
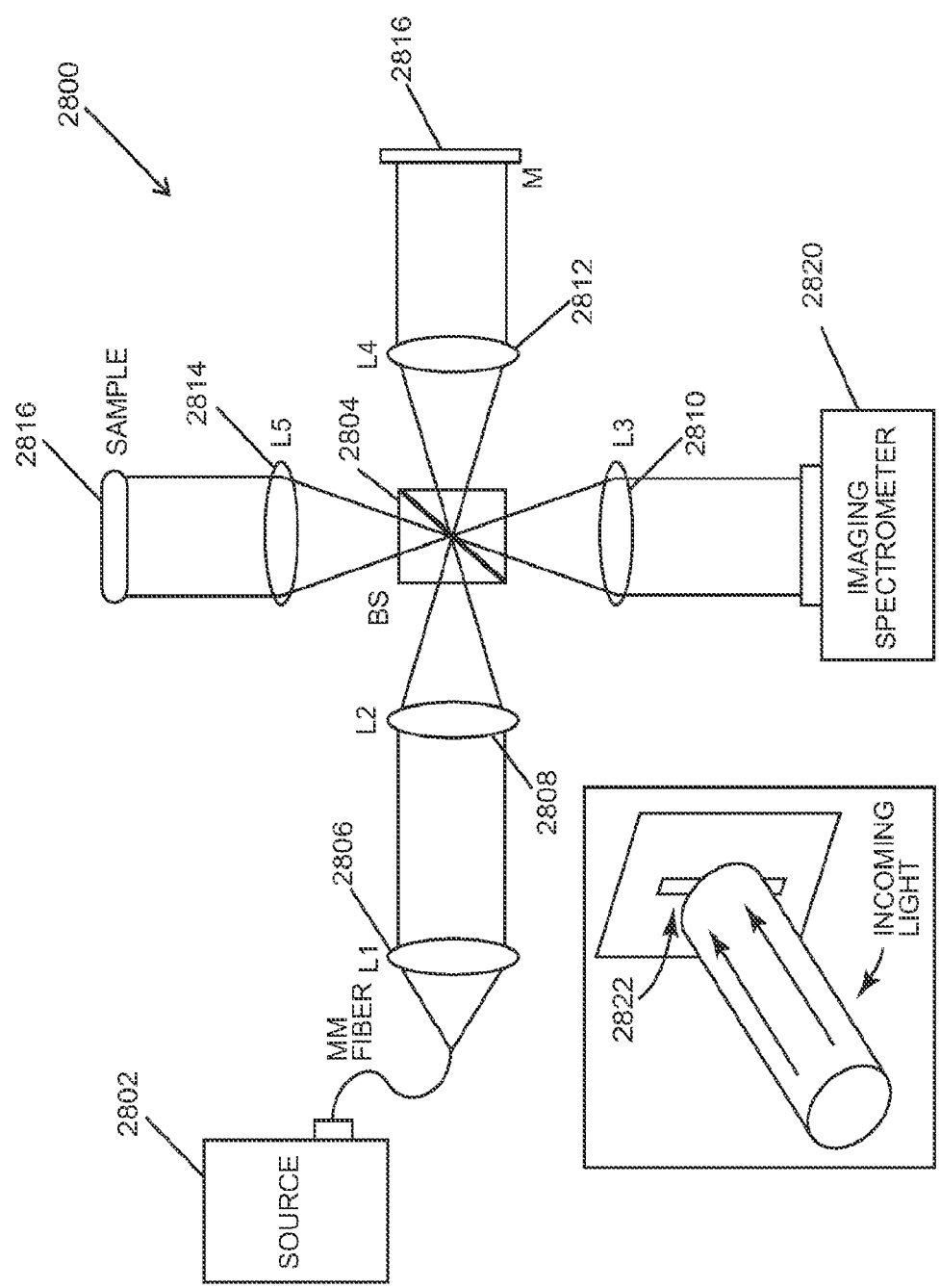
FIG. 28 shows an exemplary schematic of an exemplary pfdOCT system.

Ex vivo tissue samples were examined using the pfdOCT system first described by Graf et al. [37] A pfdOCT system 2800, shown in FIG. 28, is based on a modified Michelson interferometer geometry and utilizes a 4f interferometer first demonstrated by Wax, et al. [38] The system utilizes a light source 2802, which in one embodiment may be a Xenon arc-lamp source (150 W, Newport Oriel, Stratford, Conn.) for illumination. The 4f interferometer uses two 4f imaging systems to spatially resolve light from the light source 2802 to the detector. The system 2800 may also include a beamsplitter 2804; lenses 2806, 2808, 2810, 2812, and 2814; and a reference mirror 2816. The system 2800 of FIG. 28 may be used to examine a sample 2817. The detection plane of the imaging system coincides with an entrance slit 2822 of an imaging spectrometer 2820, which in one embodiment may be a spectrometer such as model Shamrock 303i, Andor Technology, South Windsor, Conn., which spatially resolves 255 detection channels, each 25 μm in width. The entrance slit 2822 allows only a small slice of incoming light to enter the imaging spectrometer 2820. The imaging spectrometer 2820 includes optics, along with the combination of the 600 lines/mm grating and the 1024 pixel CCD array, and limits the detected spectrum to the 500-625 nm range. Data from the imaging spectrometer 2820 may be downloaded in real time to a laptop PC via a USB 2.0 interface, and spectrometer control and data acquisition may be achieved using custom LabVIEW (National Instruments, Austin, Tex.) software.

The fLCI method seeks to recover structural information about scatterers by examining the wavelength dependence of the intensity of elastically scattered light. The technique determines scatterer sizes by analyzing the Fourier transform of the spectra originating from specific subsurface layers of a sample. Depth resolution is obtained by employing the coherence gating methods commonly used in frequency domain OCT. By exploiting the low temporal coherence length of a broadband light source in an interferometry scheme, fLCI can selectively analyze spectral information from the most diagnostically relevant layers in probed samples.

In order to perform depth resolved spectroscopy, fLCI data must be processed to simultaneously obtain depth resolution and spectral resolution, from data acquired in a single domain. To implement this processing, fLCI and spectroscopic OCT have typically employed a short-time Fourier transform (STFT) in which a Gaussian window is applied to the interference signal before taking a Fourier transform, yielding a depth scan centered about a particular center wavenumber. By shifting the center of the Gaussian window and repeating the process, a data set with both depth and spectral resolution can be generated. It should be noted, however, that with this approach any attempt to increase spectral resolution results in degradation of depth resolution and vice versa. Most recently, Robles et al. introduced the Dual Window (DW) method for processing spectroscopic OCT (SOCT) signals, which can be incorporated to the fLCI analysis [39]. The DW technique is based on performing two separate STFTs and combining the results to achieve simultaneously high depth and spectral resolution.

Figures 29A, 29B:
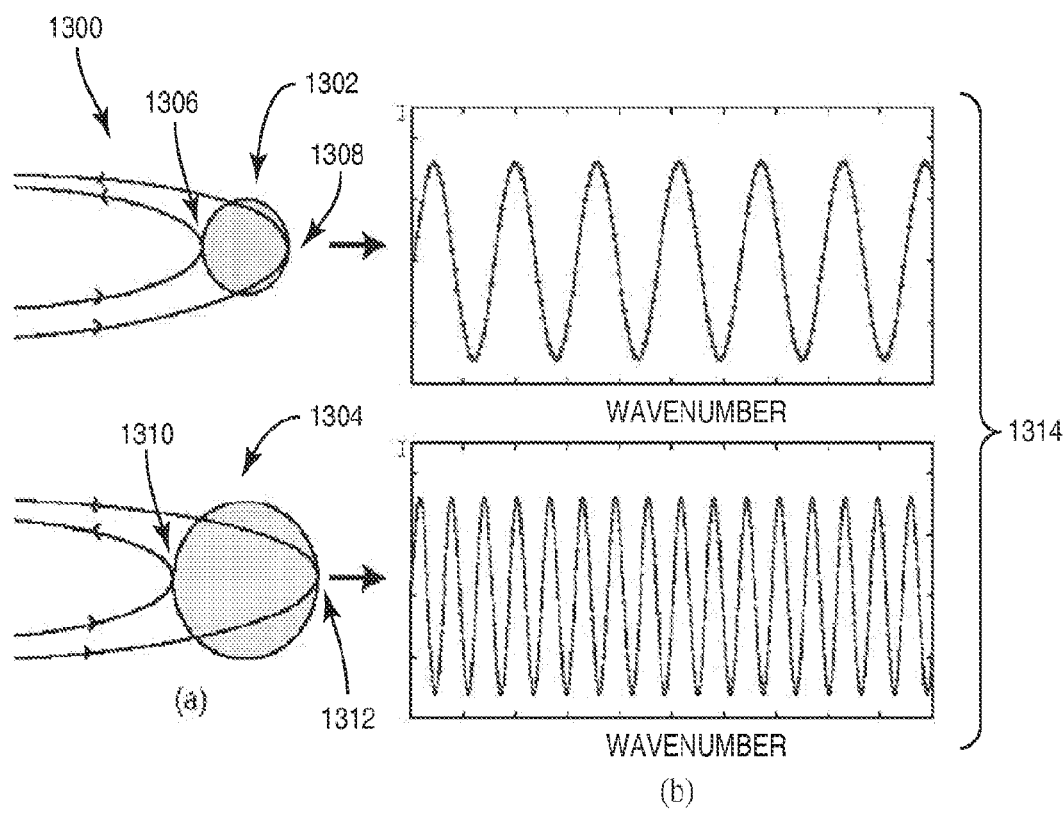
FIG. 29A shows exemplary cell nuclei with incident and scattered fields indicated.
FIG. 29B shows exemplary interference spectra with wavenumber dependent oscillations caused by interference between front and back surface reflections.

From the depth resolved spectroscopic information, fLCI seeks to determine structural information by analyzing oscillations in the spectrum of light returned from a specific depth of interest. More specifically, fLCI seeks to distinguish between normal and dysplastic epithelial tissue by detecting the nuclear enlargement that occurs at the earliest stages of precancerous development. FIG. 29A shows an illustration 1300 representing two nuclei 1302, 1304 as well as the scattering events that take place at both a front and back surface 1306, 1308 (for nucleus 1302) and 1310, 1312 (for nucleus 1304) of each nucleus 1302, 1304 where an index of refraction change is present. Depending on the coherence of the field induced by the sample [40], the reflections from the front and back surfaces 1306, 1308, 1310, 1312 of the nuclei 1302, 1304 will interfere with one another, producing constructive or destructive interference 1314, as shown in FIG. 29B. The frequency of this oscillation is directly dependent on the diameter and refractive index of the scatterer with larger particles resulting in a higher frequency of oscillation and smaller particles resulting in a lower frequency of oscillation. The fLCI method seeks to detect and analyze these spectral oscillations to measure nuclear diameter.

Data Processing

Figures 30A, 30B:
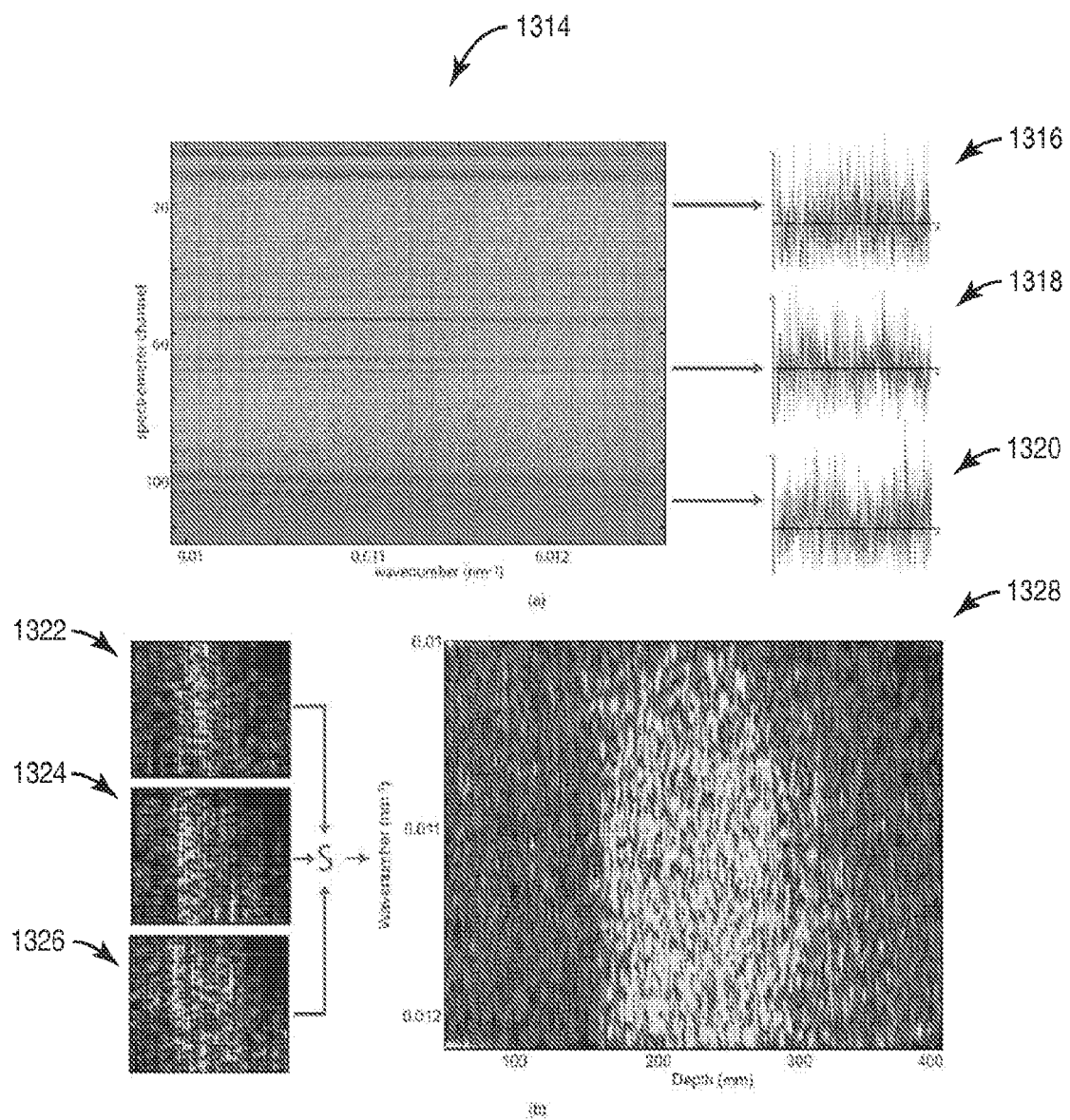
FIG. 30A shows exemplary raw data from the complete animal trial with spectra from three spectrometer channels shown.
FIG. 30B shows three exemplary typical depth-resolved spectroscopic plots produced by DW processing the spectra in FIG. 30A and summing the plots from all 120 channels produces the final TFD as shown.

The raw data acquired by the pfdOCT system consisted of 120 spectra, each of which originates from adjacent 25 μm diameter spatial points on the experimental sample. The raw interference data 1314, along with the plots of three such spectra 1316, 1318, 1320, are shown in FIG. 30A. The diameter of the signal beam was shaped to illuminate only 120 of the 255 spectral channels of the imaging spectrometer to preserve the signal to noise ratio of the measurements.

To analyze spectra from specific tissue layers in this example, the spectrum detected by each channel of the imaging spectrometer was processed using the DW technique [39]. Briefly, the DW technique uses the product of two STFTs to reconstruct the time-frequency distribution (TFD) of the interferometric signal: one STFT with a narrow window for high spectral resolution and another with a wide window for high spatial resolution. Equation 24 gives a mathematical description of the distribution obtained with the DW technique from a single spatial line, $$DW(k, z) = \int 2\langle E_S \rangle \cos(\kappa_1 \cdot \Delta OPL) e^{-\frac{(\kappa_1 - k)^2}{2a^2}} e^{-i\kappa_1 z} d\kappa_1 \times \int \left( 2\langle E_S \rangle \cos(\kappa_2 \cdot \Delta OPL) e^{-\frac{(\kappa_2 - k)^2}{2b^2}} e^{-i\kappa_2 z} \right)^* d\kappa_2, \quad (24)$$

with a and b given as the standard deviations of the windows. In this particular arrangement, the spectral resolution is limited by the actual resolution of the spectrometer used while the depth resolution is limited by the coherence length of the detected light.

Robles et al. have shown that the distribution obtained from the DW technique can be related to Cohen's class of bilinear functions [39], even though it is constructed using two linear operations. In one limit, where $a^2/b^2 \ll 1$, the DW distribution gives a measurement of the Wigner TFD with spectral and depth resolution set independently by the width of the two orthogonal windows, a and b. Significantly, the use of the two orthogonal windows eliminates many common artifacts in other TFD's, such as the cross term artifacts from the Wigner TFD and the reflections in time artifacts from the Margenau & Hill TFD. Further, the DW contains local oscillations in the spectral dimension, which reveal morphological information about the sample; specifically, the distance between scattering surfaces in the vicinity to the point of analysis.

The exemplary DW technique was implemented using a custom Matlab program to process the data with both a narrow spectral window of 0.0405 $\mu m^{-1}$ FWHM and a wide spectral window of 0.665 $\mu m^{-1}$ FWHM. The depth resolved spectra generated by each window were multiplied together to produce a plot with simultaneously high spectral and depth resolution. Resulting 120 depth resolved spectroscopic plots 1322, 1324, 1326 were summed together to improve the signal-to-noise ratio, producing a single depth resolved spectroscopic plot 1328 for each tissue sample as shown in FIG. 30B.

In neoplastic transformation, nuclear morphology changes are first observed in the basal layer of the epithelial tissue. In hamster buccal pouch tissue, the basal layer lies approximately 30 to 50 µm beneath the surface for normal tissue, and approximately 50 to 150 µm beneath the surface for dysplastic tissue. Because examination of the basal layer offers the earliest opportunity for detecting developing dysplasia, it is the target tissue layer for the fLCI technique and for this study.

Figures 31A, 31B:
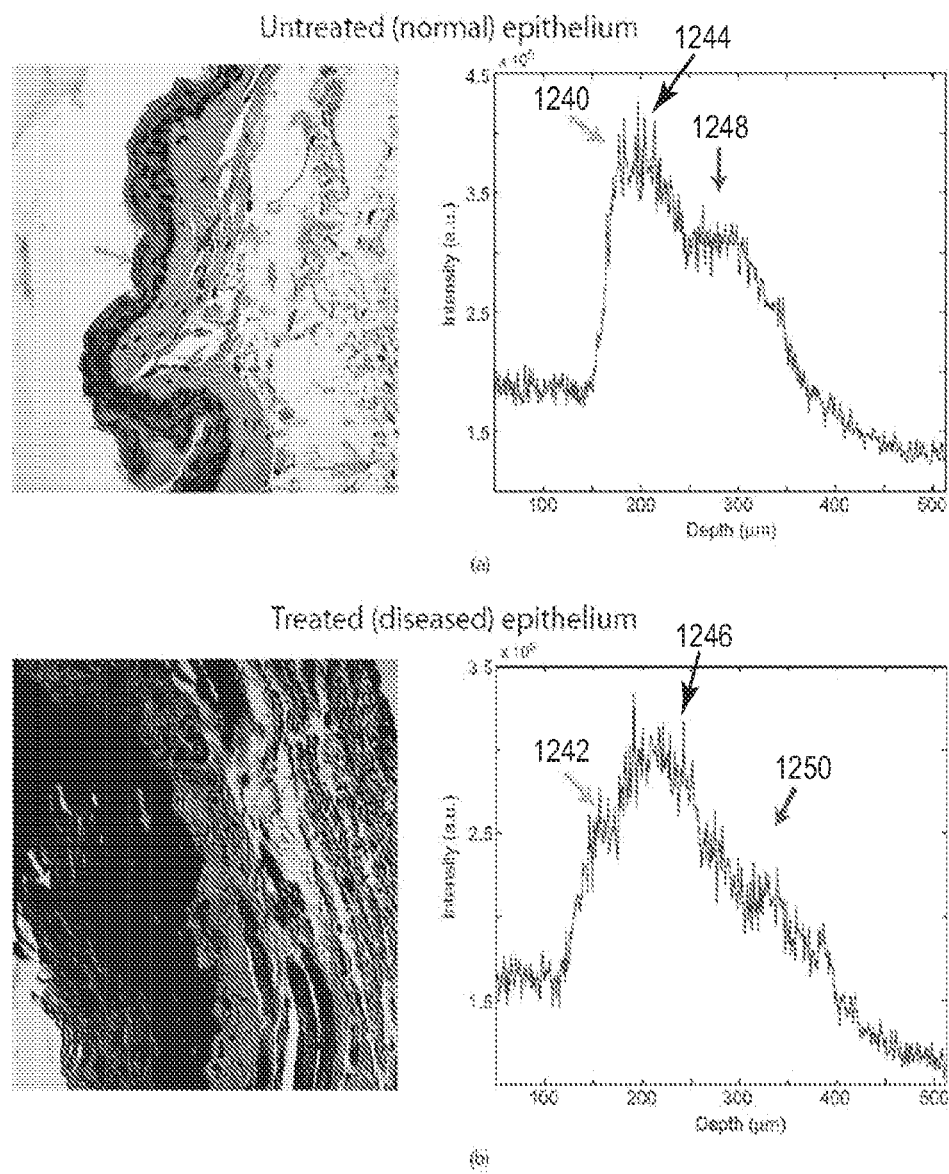
FIG. 31A shows an exemplary histopathology image and corresponding depth plot for untreated epithelium.
FIG. 31B shows an exemplary histopathology image and corresponding depth plot for treated epithelium.

In order to target the basal layer of the epithelium, the raw experimental data were first processed to yield a parallel FDOCT image by a line-by-line Fourier transform. These 'B-mode' images were summed across the transverse axis to generate single depth plots (A-scan) like those presented in FIGS. 31A and 31B. Several important histological features can be identified in the depth scans and co-registered with the corresponding histopathology images. FIGS. 31A and 31B indicate the location of a keratinized layer 1340, 1342 (green arrow), a basal layer 1344, 1346 of the epithelium (red arrow), and underlying lamina propria 1348, 1350 (blue arrow) in the micrographs of fixed and stained histological sections from untreated and treated tissue samples. Scattering peaks corresponding to the same tissue layers were identified in each depth scan. To correlate the distances in the histology images with distances in the depth scans, the index of refraction of the tissue was taken into account. An average refractive index for the tissue of n=1.38 was used to convert depth scan distances to optical path lengths [41, 42]. Variation of the refractive index within the tissue is a potential limitation of the current method and is discussed further below.

Figures 32A, 32B, 32C, 32D:
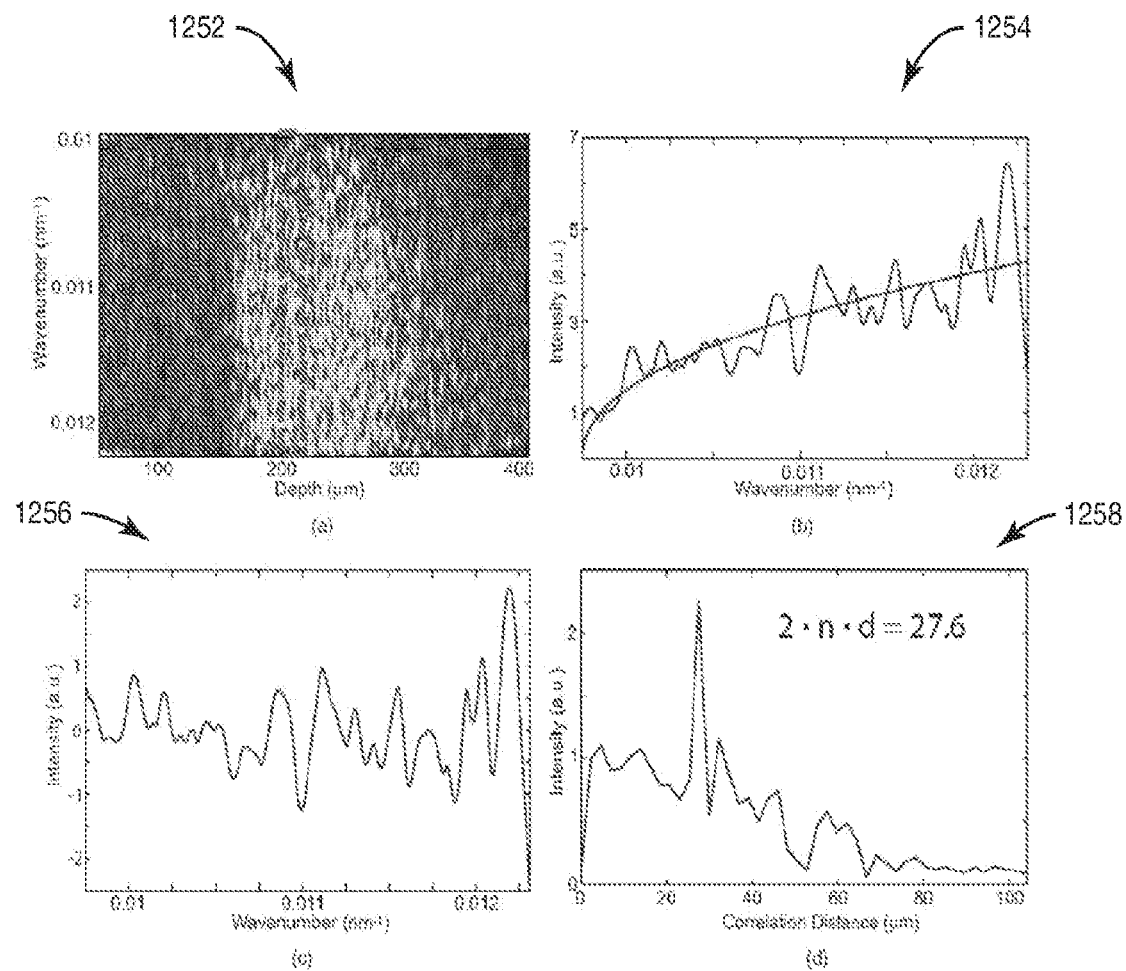
FIG. 32A illustrates an exemplary depth-resolved spectroscopic plot with basal layer indicated by dashed box.
FIG. 32B shows an exemplary spectrum from basal tissue layer along with power law fit.
FIG. 32C shows an exemplary residual spectrum from the basal tissue layer.
FIG. 32D shows an exemplary correlation plot generated by Fourier transforming the spectrum in FIG. 32C, where the peak correlation distance can be related directly to scatterer size.

For each sample, a 15 µm depth segment corresponding to the location of the basal layer was selected from the depth scan and used to guide analysis of a depth resolved spectroscopic plot 1352, as shown in FIG. 32A. The spectra from the depth identified with the basal layer in each A-scan were averaged to generate a single spectrum for light scattered by the basal layer. As shown in FIG. 32B, a power law curve 1354 of the form $y=b \cdot x^a$ was initially fit to each spectrum, modeling the spectral dependence resulting from the fractal structure of cellular organelles [43-45], including heterogeneity of the sub-structure of the nucleus. The residual of each spectrum was calculated by subtracting the power law curve from the experimental spectrum to produce a normalized spectrum 1356 which isolates the oscillatory features as shown in FIG. 32C.

The normalized spectra showed clear oscillations resulting from interference produced by scattering from the front and back surfaces of basal cell nuclei. Each normalized spectrum was Fourier transformed to generate a correlation plot 1358 similar to that shown in FIG. 32D, which shows a clear peak corresponding to the dominant frequency in the normalized spectrum. Peak detection was carried out by an automated, custom Matlab program (Mathworks, Natick, Mass.). The script first high-pass filtered the spectrum with a cutoff of 4 cycles in order to remove any low frequency content not removed by the power law fit. The location of the peak in the correlation plot was then automatically detected by the Matlab script and related to scatterer diameter with the simple equation d=correlation distance/(2·n), where n is the refractive index and d is the diameter of the cell nuclei. An nuclear index of refraction of n=1.395 was assumed (9).

Results

Figure 33:
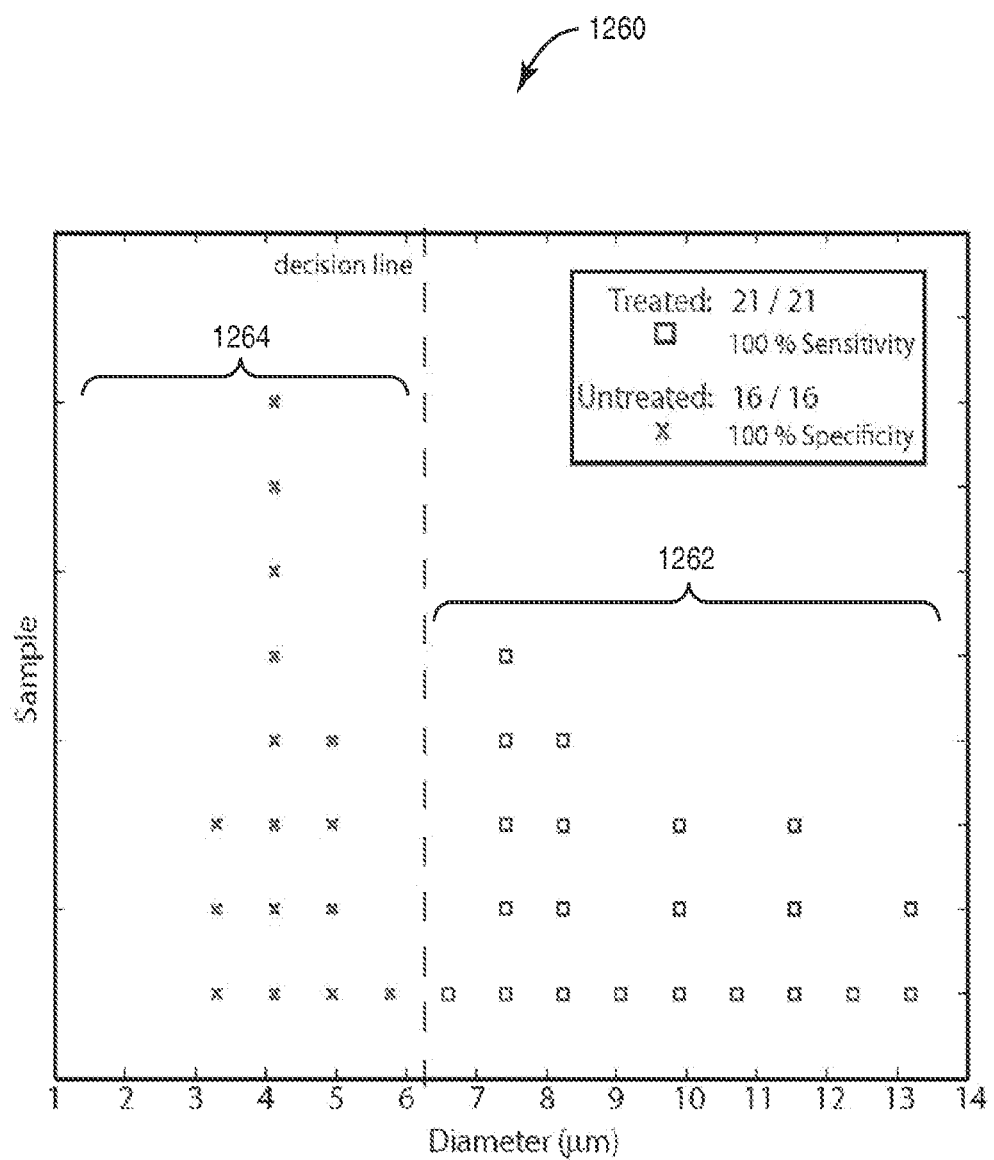
FIG. 33 shows exemplary nuclear diameter measurements for each sample of the complete animal trial.

The results of the complete animal trial are summarized in Table 2 and presented graphically in chart 1360 in FIG. 33.

TABLE 2

Summary of nuclear diameter measurements from the complete animal trial.

|  | Untreated | Treated |
| --- | --- | --- |
| N | 16 | 21 |
| Mean (µm) | 4.28 | 9.50 |
| Std. Dev | 0.69 | 2.08 | p-value <0.0001**

The sixteen (16) untreated tissue samples had a mean basal layer nuclear diameter of 4.28 µm with a standard deviation of 0.69 µm. The 21 treated tissue samples had a mean basal layer nuclear diameter of 9.50 µm with a standard deviation of 2.08 µm. A statistical t-test revealed a p-value of less than 0.0001, indicating a highly statistically significant difference between the basal layer nuclear diameters of the two populations. Histological analysis revealed that untreated samples appeared as unaltered epithelium while the treated samples all showed a diseased tissue state ranging from inflammation and hyperplasia to dysplasia.

FIG. 33 plots each treated (blue square) tissue sample 1362 and untreated (red x) tissue sample 1364 as a function of its measured basal layer nuclear diameter. The presented decision line results in excellent separation between the normal and diseased samples. Using the indicated decision line, the study results correctly categorize 21 of 21 treated samples, providing 100% sensitivity and correctly categorize 16 of 16 untreated samples providing 100% specificity.

Discussion

The experimental results of the complete animal trial show that fLCI has great potential as a technique for distinguishing between normal and dysplastic epithelial tissues. Experimental measurements showed an excellent ability to precisely and accurately distinguish between treated and untreated animal tissue using in situ measurements of nuclear diameter as a biomarker. The measured diameters correspond nicely with the nuclear diameter expected for the basal tissue layer of hamster cheek pouch epithelium [46] when measurements are adjusted to account for fLCI's measurement of the mirror axis of cell nuclei. [47] It should be noted that the development of dysplasia results in thickening in the basal tissue layer and a breakdown of cellular organization. As a result, fLCI measurements likely probe the major axis of some nuclei in diseased tissue, further contributing to the detected nuclear enlargement when compared with normal tissue.

The use of the DW technique to extract depth resolved spectra from animal tissue data is an important advance. The DW processing method permitted the measurement of spectral oscillations induced by nuclear scattering that could not be detected in data processed with the STFT. fLCI data processed with the STFT suffers from an inherent tradeoff between spectral resolution and depth resolution. As a result of this tradeoff, achieving an acceptable spectral resolution necessarily requires the degradation of depth resolution to the point that spectral oscillations induced by nuclear scattering are washed out. This washout is likely due to phase and frequency differences in the spectra originating from the different tissue layers, which were combined as a result of the poor depth resolution. In contrast, the DW technique produced depth resolved spectroscopic plots with simultaneously high depth and spectral resolutions. The DW technique generated satisfactory spectral resolution while maintaining high depth resolution, therefore permitting the spectral analysis of thin tissue segments. By avoiding the unwanted combination of signals from many tissue layers, the oscillatory components of spectra originating from the basal tissue layer were preserved and available for analysis.

Though the results of the animal study are extremely promising, the current methods are not without limitation. The dependence on refractive index in selecting tissue layers of interest is a challenge that must be further examined in the future. The current fLCI data processing algorithm does not account for potential variations of refractive index within a tissue. The current method also does not adjust for potential index changes induced by the onset of dysplasia which also may be a confounding factor. In order to accurately measure optical path lengths within a tissue sample, a dynamic model of refractive index must be developed. Similarly, a robust method to account for the varying thickness and location of the basal layer during neoplastic transformation should be implemented.

Additionally, a more complex model of scatterers within the tissue should be developed for future studies. Other light scattering research [47-49] indicates that, in addition to spectral modulations, spectral shape can yield insight into tissue micro-architecture and health. Developing a light scattering model that can capture this information will be a priority as the fLCI technology is further developed. Although the detection of peaks in the correlation plots for this study was automated to eliminate bias, subsequent analysis of the correlation data revealed that some plots contained multiple prominent peaks. Understanding how correlations between neighboring cellular structures and correlations between tissue layers contribute to generated correlation plots will facilitate the development of an advanced scattering model.

It is believed that the correlation peak represents nuclear diameter, as opposed to the separation between nuclei, for three primary reasons. First, the front and back surfaces of each nucleus are relatively well aligned for interference in the axial direction, whereas the alignment between different nuclei is not as well ordered and therefore less likely to produce oscillations in the spatially averaged spectrum. Second, because the distances between nuclei would have a much larger variation than the diameters of individual nuclei, it is expected that the separation between nuclei to yield a much broader distribution of distances rather than the narrow correlation peaks seen in the correlation plots. Finally, this study finds that the correlation peak shifts to longer distances for treated (diseased) samples while remaining at smaller distances for normal samples. This finding is consistent with the measurement of nuclear enlargement seen in hyperplastic and dysplastic tissues. On the other hand, if the correlation plot was measuring nucleus-to-nucleus correlation, it is expected to see the peak shift to smaller distances in diseased tissue due to the increase in nucleus-to-cytoplasmic ratio observed in dysplastic tissue.

The results of this study demonstrate fLCI's ability to distinguish between normal and diseased (DMBA-treated) epithelial tissue with high sensitivity and high specificity. The in situ nuclear morphology measurements are acquired without the need for exogenous staining agents or fixatives. The ability of the fLCI technique to make quantitative nuclear morphology measurements demonstrates its potential as an effective technology for non-invasively detecting dysplasia using an optical measurement. The results of these experiments lay the groundwork for further development of fLCI into a technique for clinical diagnostic applications such as the detection of early cancer development.

The techniques described herein can also be used to detect early cancerous cells development. For example, experiments were performed using the techniques described herein to detect early colorectal cancer development in an azoxymethane rat carcinogenesis model with fLCI.

Colorectal cancer (CRC) is the third most common cancer and the third leading cause of cancer death in men and women in the United States [50]. As is commonly known, the most successful practice for preventing cancer mortality is to regularly screen people at risk. This is particularly important for CRC since the disease is largely asymptomatic until it has reached an advanced stage; fortunately, if diagnosed early, the survival rate dramatically improves. Today, the gold standard for screening CRC is conventional colonoscopy, which relies on visual inspection through an endoscope to detect polyps and adenomas. Once identified, the decision to remove these mucosal growths is based on size, where it is recommended that lesions >5 mm in diameter be removed [51]. This approach, however, suffers from serious weaknesses: 1. There is no reliable metric for determining whether lesions are adenomatous or metaplastic; hence, the decision to remove these lesions is left to the discretion of the physician. Note that approximately 90% of all cases of CRC originate through benign adenomas [51]. 2. Despite the fact that small lesions (<5 mm) are not typically removed, some studies have presented evidence that these are very likely to contain neoplasias, particularly for lesions proximal to the left colon [52]. 3. Flat adenomas, which are ten times more likely to contain malignancy compared to similarly sized polyps, appear similar to the surrounding tissue, and are consequently very difficult to detect with colonoscopy [53]. 4. Because all detected polyps are considered adenomatous [51], many unnecessary biopsies and polypectomies are performed, which increase the probability of complications [54]. Lastly, while other screening tests are available, including fecal occult blood tests, sigmoidoscopy, and virtual colonoscopy, these are more limited and less effective; further, in the event that an abnormality is detected with these alternative screening tests, patients must then undergo a colonoscopy [55].

The weaknesses of colonoscopy, as described above, highlight the need for technologies that assess tissue health quantitatively and in a minimally invasive manner. To this end, biomedical optics has emerged as a promising field, in which various techniques have been developed to probe different biomarkers accessible via optical absorption and/or scattering measurements. For example, 4-dimensional elastically scattered light fingerprinting (4D ELF) [56] and diffuse reflectance spectroscopy [57] have been able to quantify tissue hemoglobin concentration as a surrogate biomarker for malignancy. Further, low-coherence enhanced backscattering spectroscopy (LEBS) [58] and angle-resolved low coherence interferometry [59] have retrieved information regarding nano- and micro-tissue morphology, thus providing insight to precancerous states.

In this disclosure, another exemplary application of an emerging optical technique, namely Fourier domain low coherence interferometry (fLCI), to measure early CRC changes using an analysis of ex-vivo tissues drawn from the azoxymethane (AOM) rat carcinogenesis model. fLCI measures oscillatory features in depth resolved spectra, also known as local oscillations, which result from coherent fields induced by the scattering by the front and back surfaces of cell nuclei in tissue [60]. Thus, fLCI uses nuclear morphology as a biomarker of disease, making it sensitive to the earliest stages of precancerous development. To achieve depth resolved spectroscopic analysis, the dual window (DW) techniques described herein can be employed, which obtain simultaneously high spectral and depth resolution, and yield access to the local oscillations [61]. Further, fLCI signals can be processed to yield cross sectional images of samples, as in Fourier domain optical coherence tomography (FD-OCT) [62], thereby enabling co-registration of the structural information with the spectroscopic analysis. The capabilities of fLCI using the DW technique have been demonstrated using scattering phantoms [63] and ex-vivo samples from a hamster cheek pouch model [60]. Here in this example, fLCI is used to provide a spatially resolved, functional analysis of ex-vivo tissue samples at three depths and along two different sections of the left colon to demonstrate fLCI's ability to detect early CRC development.

Materials and Methods

Animal model

This study used the AOM rat carcinogenesis model, a well characterized and established model for colon cancer research and drug development [64]. The cancerous progression of this model is similar to that seen in humans and is a good surrogate for human colon cancer development. In addition, the short induction period and high incidence of aberrant crypt foci (ACF), which are preneoplastic lesions [65], make this model a practical choice for testing the ability of fLCI to detect precancerous development in the colon.

All animal experimental protocols were approved by the Institutional Animal Care and Use Committee of The Hamner Institute and Duke University. Forty F344 rats (six-week old, male; Charles River Laboratories Inc., Kingston, N.Y.) were housed in The Hamner's animal facility for a 10-day acclimation period prior to any testing. All the animals were provided with a regular National Institutes of Health-07 diet (Ziegler Brothers, Gardners, Pa.) for the first 4 days of acclimation. Thereafter, the diet was switched to the pellet form of American Institute of Nutrition (AIN)-76A (Dyets Inc., Bethlehem, Pa.) and continued for the rest of study period. Two animals per cage were housed in polycarbonate, solid-bottom cages with Alpha-dry bedding in an animal room with a 12-hr light/dark cycle. Cages were changed twice a week. Pelleted, semipurified AIN-76A diet and water were available ad libitum. Weekly body weights were collected during the whole study period, and clinical observations were performed to monitor the health of the animals.

Figure 34:
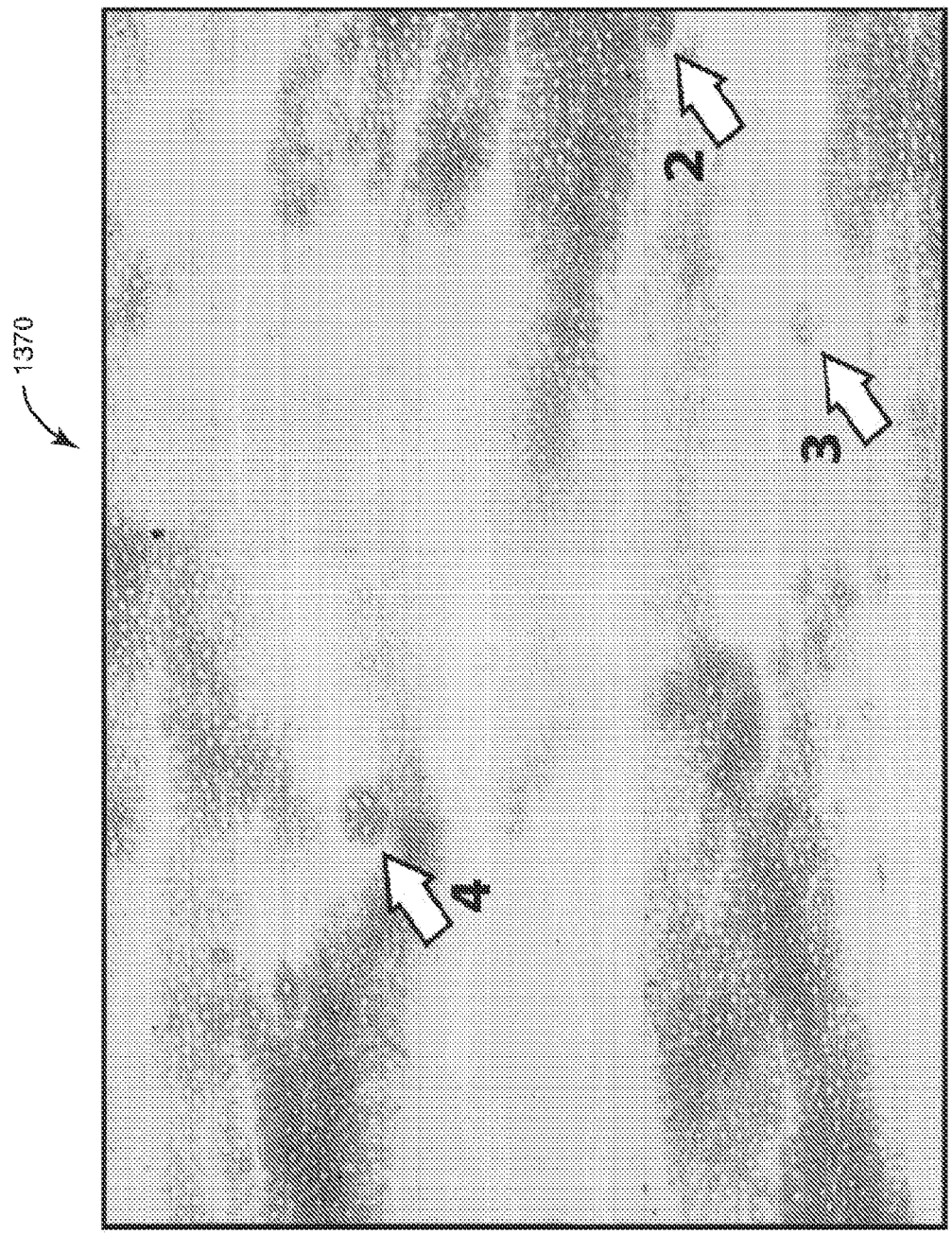
FIG. 34 is a picture of an exemplary stained tissue sample, four (4) weeks post treatment with three (3) aberrant crypt foci (ACF) containing 2, 3, and 4 aberrant crypts.

After 10 days of acclimation, the 40 rats were randomized into groups of 10. Thirty animals received intraperitoneal (IP) injections of AOM >90% pure with a molar concentration of 13.4 M (Sigma, St. Louis Mo.) at a dose level of 15 mg/kg body weight, once per week, for 2 consecutive weeks (2 doses per animal). The remaining ten animals received saline by IP and served as the control group. At 4, 8, and 12 weeks after the completion of the dosing regimen, the animals (10 AOM-treated and 3 or 4 saline-treated rats per time point) were sacrificed by $CO_2$ asphyxiation. The colon tissues were harvested, opened longitudinally, and washed with saline. Then, the tissues were split into 4-5 different segments, each with a length of 3-4 cm. Only the two most distal segments of the colon were analyzed for these experiments: the distal left colon (LC) and proximal LC. Then, the samples were placed on a cover glass for examination with the parallel frequency domain OCT system as described above. Finally, the tissue samples were fixed in formalin and stained with methylene blue in order to be scored based on the number of ACF, which are defined as foci containing more than two aberrant crypts. FIG. 34 shows an image 1370 of an exemplary stained tissue sample, four (4) weeks post treatment with three ACF that contain "2," "3," and "4" aberrant crypts.

Detection System

Figure 35:
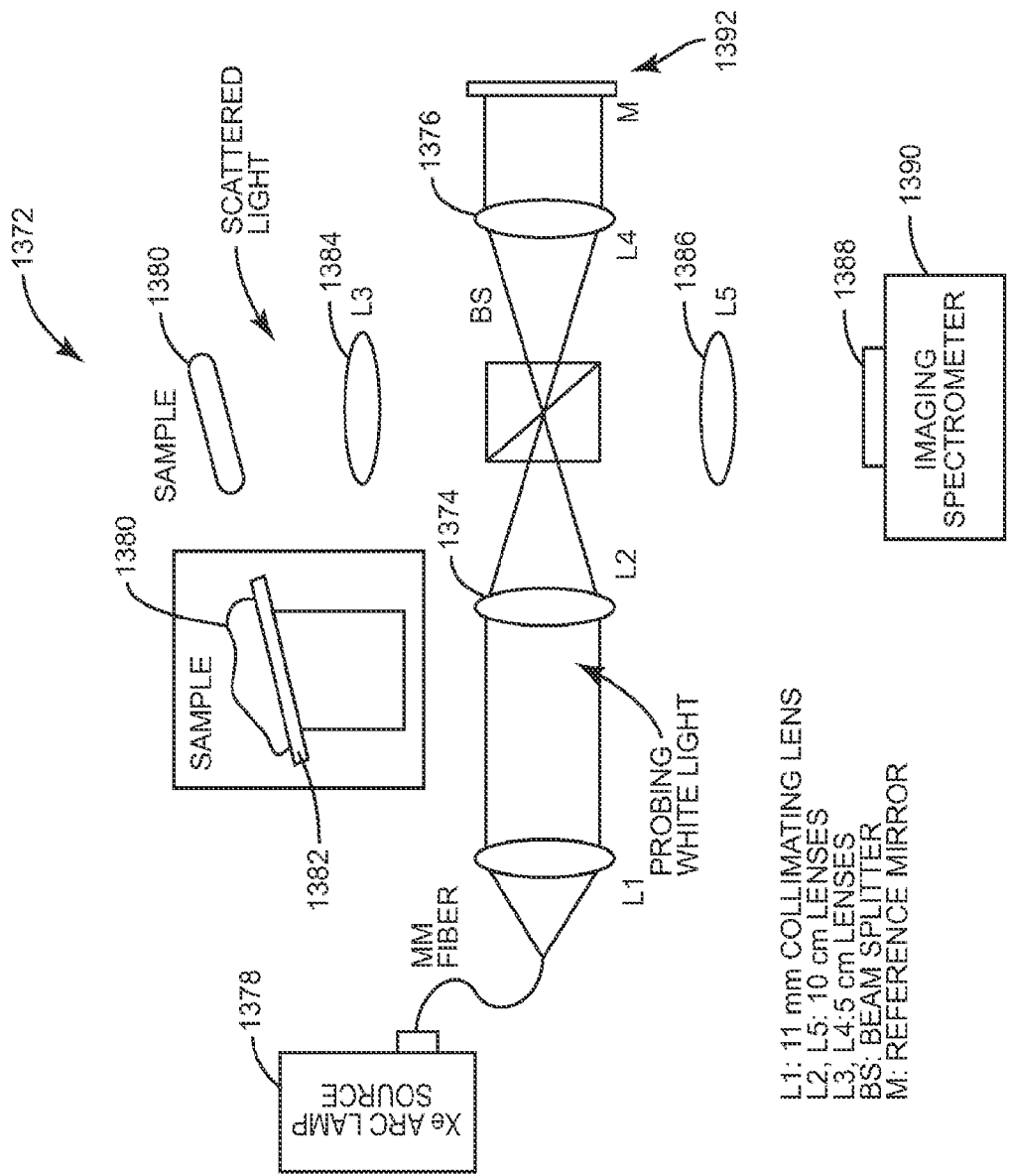
FIG. 35 illustrates an exemplary parallel frequency domain OCT system operating in scatter mode.

FIG. 35 illustrates an exemplary parallel frequency domain OCT system 1372 operating in scatter mode. The exemplary system 1372 used is a parallel frequency domain OCT (pfdOCT) system [66], which consists of a Michelson interferometer geometry with the addition of four lenses that form a 4-F interferometer [67]. Using lenses L2 and L3 1374, 1384 as seen in FIG. 35, the multimode fiber-coupled light from a Xe-arc lamp 1378 (e.g., 150 W, Newport Oriel, Stratford, Conn.) is collimated onto a sample 1380. The samples 1380 are placed atop a #0 cover glass 1382, which is tilted slightly to avoid saturation from specular reflecti by the glass-air interface and thus allowing detection of only the scattered light. This is known as scatter mode imaging. For the ex-vivo colon tissue, the lumen side was placed facing down (against the cover glass 1382), since the light illuminates from below the sample as seen in the inset of FIG. 35. Then, using lenses L3 and L5, 1384, 1386, light scattered from the sample 1380 is imaged onto an entrance slit 1388 of an imaging spectrograph 1390 (e.g., SP2156, Princeton Instruments, Trenton, N.J.). A reference arm 1392 follows a similar optical path, with lenses L2 and L4, 1374, 1376, and lenses L4 and L5 1376, 1386. After light is dispersed into its wavelength components by the imaging spectograph 1390, the interference between the sample and reference fields is recorded using a CCD camera (e.g., Pixis 400, Princeton Instruments, Trenton, N.J.). Detection is centered about 600 nm with a bandwidth of 240 nm. This configuration allows for 201 interferograms to be collected simultaneously (limited by the beam width), yielding B-mode OCT images from a single exposure.

For this particular configuration, the system 1372 underwent slight modifications compared to previous system implementations reported in [60, 63, 66]. First, a 2× magnification of the sample field at the spectrometer slit was achieved by setting the focal length of lenses L3 and L4 1384, 1376 equal to 50 mm, and that of lenses L2 and L5 1374, 1386 equal to 100 mm; with a pixel size of 20 µm, this resulted in a lateral resolution of 10 µm. The use of shorter focal length lenses also allowed for the total footprint of the system to be reduced, ultimately allowing the system to be made portable. Portability is achieved by placing the system inside an 8"×18"×24" custom made aluminum alloy box atop a heavy-duty stainless steel utility cart for transportation to on-site analysis of tissue samples.

Data Processing

The fLCI process for assessing cell nuclei diameter involves multiple steps in this example. The first step is to obtain OCT images of the samples. Next, spatially resolved spectra are calculated using the DW technique. Then, the spatial information provided by the OCT images is used to co-register the spectroscopic information; this allows for the spectra to be consistently analyzed at specific tissue depths. Finally, spectra from specific regions within the tissues are averaged to yield spectral oscillations that reveal cell nuclear diameters. In this section, a detailed exemplary procedure of these steps is provided.

Figure 36:
FIG. 36 illustrates an exemplary pfdOCT image of an ex-vivo rat colon sample.

To obtain OCT images in this example, the initial step is to digitally remove the DC background from the interferometric signal using separate acquisitions of the sample arm, reference arm, and dark signal. Then, the interferometric data are normalized by the reference arm intensity to remove any spectral dependence originating from the source and detector efficiency. The interferograms are then resampled from wavelength to a linear wavenumber vector ($k=2\pi/\lambda$) and digitally corrected for chromatic dispersion [68]. Subsequently, the signals are Fourier transformed to obtain OCT images with an axial resolution of ~1.10 µm (experimental). A refractive index (RI) of n=1.38 is used to convert the optical path length to physical axial distance in tissue [69]. FIG. 36 illustrates an exemplary representative image 1400 of an ex-vivo rat colon sample.

To obtain depth-resolved spectroscopic information, the DW technique is used [61]. As previously illustrated in FIGS. 5A-5C, the method consists of multiplying two STFTs 500, 502 in FIG. 5A that operate on each interferogram. An STFT is implemented by sweeping a window across the interferometric data in FIG. 5A while simultaneously taking a Fourier transform at each step, thus giving a map of the spectral content confined within a spatial (or axial) region, as illustrated in FIG. 5B. These maps are known as time-frequency distributions (TFDs). However, TFDs obtained using a single STFT suffer from an inherent trade-off between the resulting spectral and spatial resolutions. The DW technique, on the other hand, utilizes the high spectral resolution of an STFT using a narrow window, and the high spatial resolution of an STFT using a wide window to avoid the deleterious effects of the time-frequency trade-off [61]. Here, Gaussian windows were used with standard deviations w1=0.029 µm-1 and w2=0.804 µm-1, resulting in TFDs with an axial resolution of 3.45 µm and spectral resolution of 1.66 nm. Note that this process is conducted for each A-scan, thus giving a spectrum for each point in an OCT image.

The last step to obtaining spectral information from specific tissue depths (i.e., local oscillations) is to co-register the OCT images 508, 510 in FIG. 5B with the DW TFDs. This process involves using the images to identify the contour of the tissue surfaces and calibrate the analysis relative to this "zero" depth. Note that if a surface is not clearly discernable at any particular A-scan, no further analysis is conducted there. With this information, the DW TFDs can be properly aligned and thus consistently provide spectral information from specific tissue depths.

Two STFTs, 508, 510 in FIG. 5B, one obtained with a narrow window and another with a wide window, are multiplied together to obtain the DW TFD 512 in FIG. 5C. Gaussian windows were used with standard deviations w1=0.029 µm-1 and w2=0.804 µm-1, resulting in TFDs with an axial resolution of 3.45 µm and spectral resolution of 1.66 nm.

Once the spectra are properly aligned, regions of interest, both laterally and axially, are identified and averaged in order to provide sufficient signal-to-noise ratio for the spectral analysis that follows. In the lateral direction, twenty (20) DW TFDs are averaged to yield ten (10) different lateral segments in each OCT image. Note that in previous studies all TFDs in an image were averaged [60]; thus, the analysis provided here produces a ten-fold increase of the spatial information. In the axial direction, the spectral averages of 25 µm depth segments from three different sections are calculated: at the surface (surface section 0-25 µm), centered about 35 µm in depth (mid section. 22.5-47.5 µm), and centered about 50 µm in depth (low section 37.5-62.5 µm). The area inside the red dotted line in FIG. 36 gives an example of a resulting mid section from which the spectra are averaged to determine the nuclear diameter.

Figures 37A, 37B, 37C:
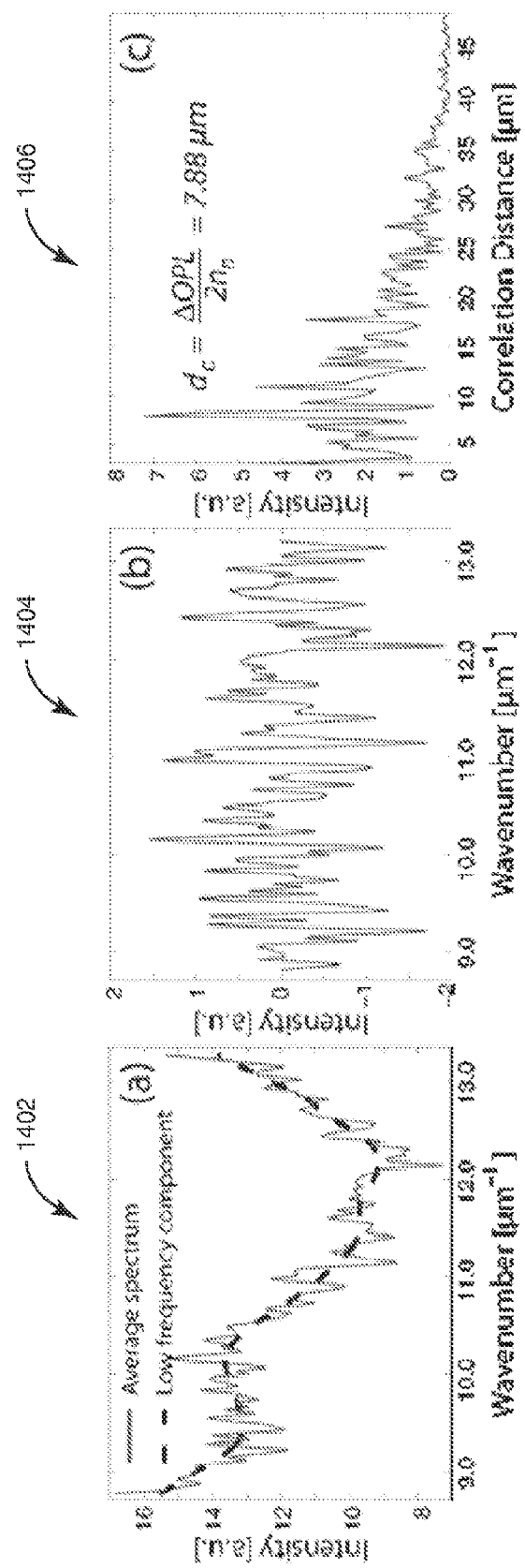
FIGS. 37A-37C illustrate exemplary average spectrum from the delineated region in FIG. 36, along with a low frequency component (black dotted line); the low frequency component is subtracted from the averaged spectrum of obtain the local oscillations (FIG. 37A); a Fourier transform yields a correlation function (FIG. 37B); and the peak corresponds to an average cell nuclear diameter in the region of analysis (FIG. 37C)

The spectra from the averaged regions contain two components. The first component contains the low frequency oscillations that have been associated with the periodic fine structures induced by spherical scatterers, which have been analyzed previously using the van de Hulst approximation in light scattering spectroscopy (LSS) [63, 70-72]. The approximation gives an analytical solution to the scattering cross section of spherical scatterers, which shows that the periodicity of the spectral oscillations depends on size, as well as on the ratio between the RI of the scatterer and surrounding medium [72]. This ultimately results in relatively low frequency oscillations. However, it has been observed that due to the lack of knowledge of the precise RI of the scatterer and the surrounding medium [73], the amount of useful information that can be extracted from the LSS method is limited. Therefore, the low frequency oscillations are isolated using a smoothing function in Matlab (Mathworks, Natick, Mass.) and subsequently removed from the spectra. This process isolates the second component: the high frequency oscillations of the spectra, which correspond to the local oscillations resulting from coherent fields induced by the cell nuclei in the averaged region. Unlike the periodic fine structures in LSS, the local oscillations only depend on the size and RI of the scatterer, thus resulting in higher frequencies. Specifically, the periodicity of the local oscillations is given by the sample field's round trip optical path length ($\Delta OPL$) thought the scatterer, and is related to the scatter size (in this case, dc) by $dc=\Delta OPL/(2nn)$, where nn is the RI of the cell nuclei. FIG. 37A illustrates the average spectrum 1402 (solid blue line) along with the isolated low frequency component (dotted black line) for the averaged region shown in FIG. 36. FIG. 37B shows the resulting local oscillations 1404.

Finally, a Fourier transform of the local spectral oscillations is taken to produce a correlation function, where it is attributed that the peak in this function to indicate the average cell nuclear diameter in the region of analysis [60]. Other scatterers, such as other cellular organelles and nuclear content, may also produce peaks in this function, but due to their random orientation, size, and spacing with one another, the resulting signal is unlikely to produce a peak greater in magnitude than that of the average cell nuclear diameter. A correlation function 1406 for the local oscillations in FIG. 37B is shown in FIG. 37C, where the correlation distance (dc) has been properly scaled to account for the round trip optical path length and the RI of the cell nuclei. A constant nuclear RI of nn=1.395 was assumed for this analysis [69]. As a last step, the peak detection process is automated to enable analysis of large data sets. To achieve this, the correlation function is subject to further processing, where the 1/f noise is removed using a smoothing function. Then, only maxima that are 3.5 standard deviations above the mean of the correlation function are considered to be clear peaks. If this criterion is not met at any particular region, the measurement is discarded.

Results

Depth Sections

The nuclear diameters from the three different tissue depth sections and for all time points are summarized in FIGS.

38A-38C and Table 1408 in FIG. 39. Note that the control group measurements of all the time points were combined, since no statistically significant differences were found between them. Statistical tests were conducted using a two-sided student t-test.

Figures 38A, 38B, 38C:
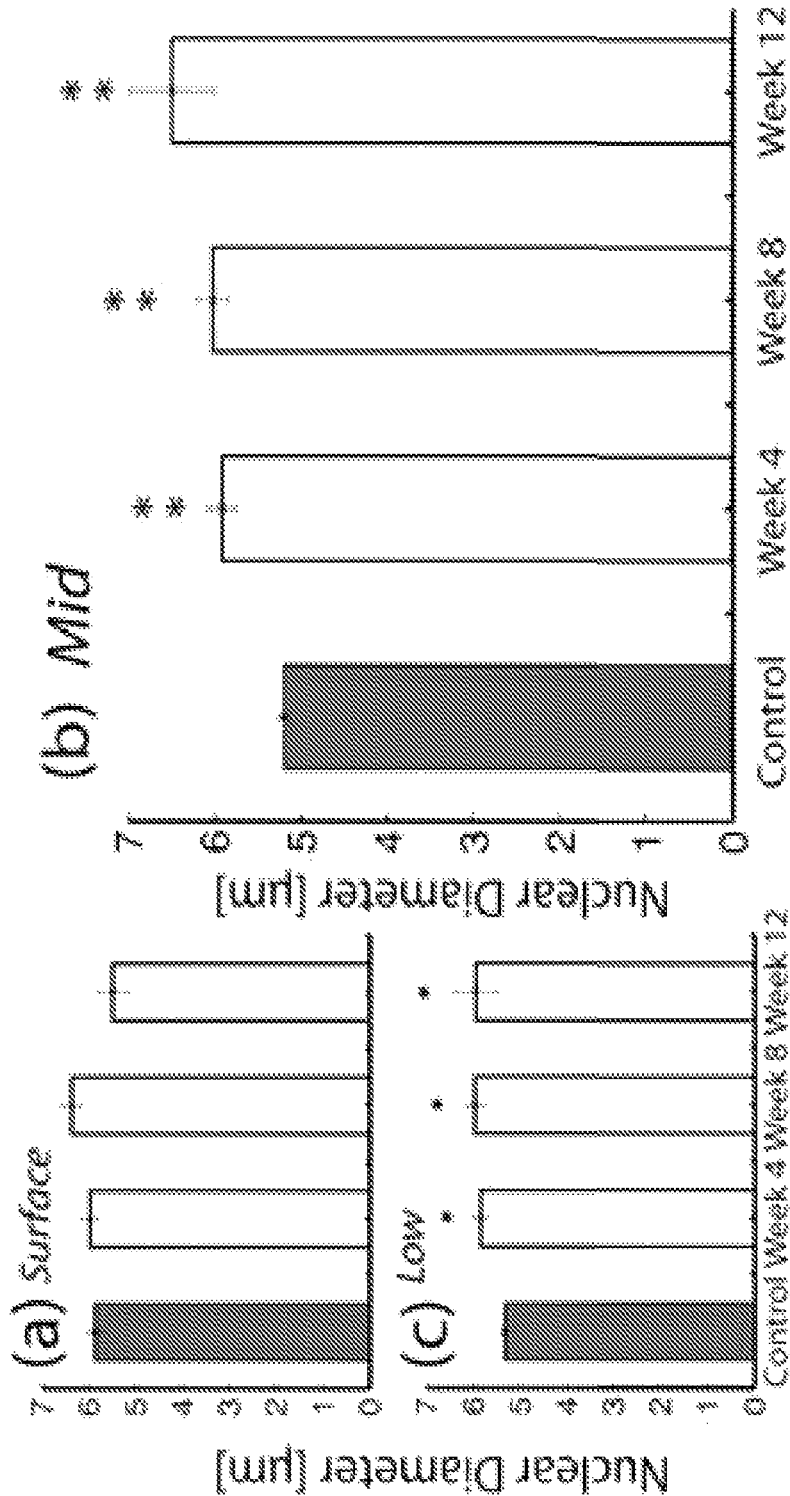
FIGS. 38A-38C illustrate exemplary nuclear diameter by depth sections, with a mid section (e.g., 35 µm in depth) providing the most significant results, with $p\text{-values} < 10\text{-}4^{**}$ for the treated samples at all time points when compared to the control group.

As shown in FIGS. 38A-38C, the mid section (35 μm depth) provided the most significant results, where the treated groups at all three time points yielded p-values<10-4** when compared to the control group. The fLCI measurement for the control group at the mid section yielded an average cell nuclear diameter of 5.15+/−0.05 μm, while for the treated groups it was found to be 5.91+/−0.15 μm, 6.02+/−0.18 μm, and 6.49+/−0.49 μm at 4, 8, and 12 weeks after treatment, respectively. For the deepest (low, 50 μm depth) section, mildly statistically significant results were observed, with p-values<0.05*. No statistical significance was found at the surface, and mildly significant differences (p-values<0.05*) were found at the low (50 μm) section.

Length Segments

The two tissue segments (proximal and distal left colon) were further analyzed separately for the mid depth section. The measured cell nuclear diameters and number of ACF are summarized in Table 1410 in FIG. 40. It was found that for all the time points, and for both segments, the measured nuclear diameters for the treated groups were significantly different from the control group (p-values<10-4**).

Figures 41A, 41B, 41C:
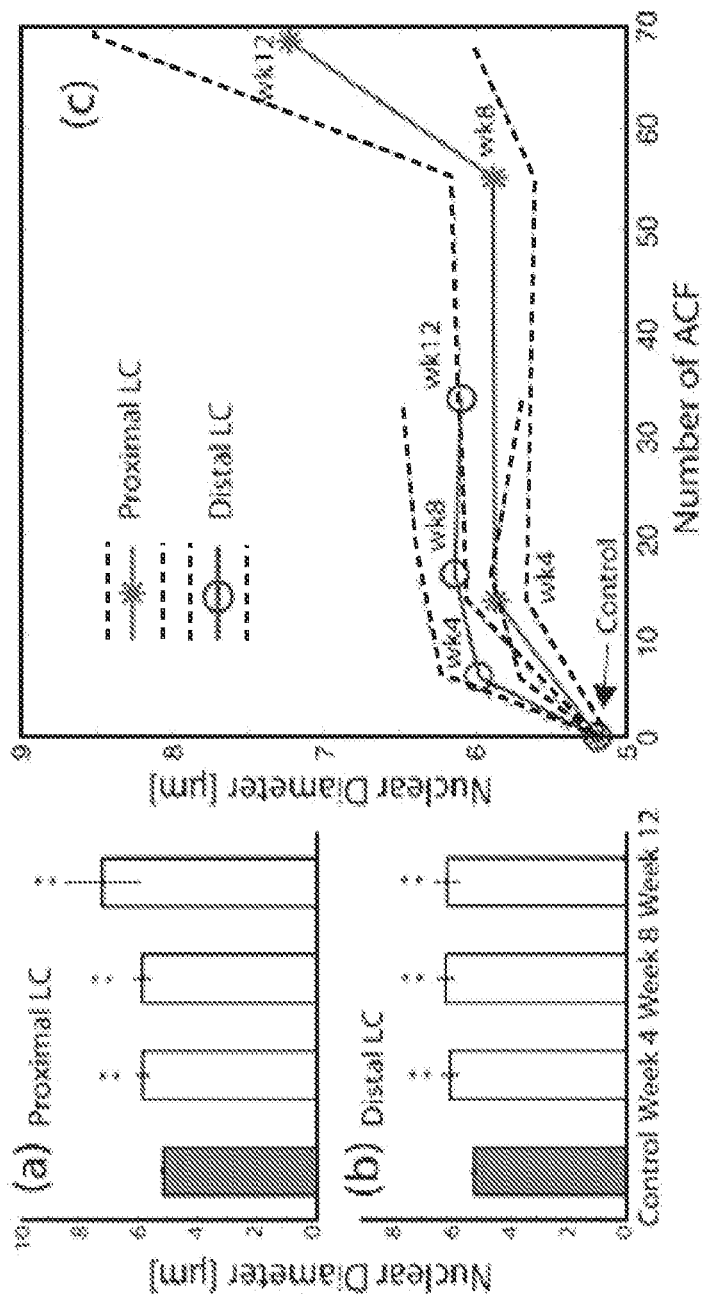
FIGS. 41A-41C illustrate exemplary results by colon length segments; highly statistical differences ($p\text{-value} < 10\text{-}4^{**}$) were observed between the control group and treated groups for the proximal left colon (LC) (FIG. 41A) and distal LC (FIG. 41B)

The results are also summarized in FIGS. 41A and 41B. Note that significant differences were observed for both segments after only four (4) weeks post treatment in this example. The measured increase in the nuclear diameter, however, remained relatively constant thereafter, with the exception of the last time point in the proximal LC. Here, the nuclear diameter increased dramatically from ~6.0 μm to ~7.2 μm. To investigate this further, FIG. 41C plots the nuclear diameter as a function of the average number of ACF, which are preneoplastic lesions. For clarity, each point with its corresponding time period is also identified. Note that the formation of ACF was faster in the proximal LC compared to the distal LC, and that the plot shows a region of little nuclear morphological change after the initial formation of ACF. This plateau region is present in both sections and is initially independent of the number of ACF. However, once the number of ACF increased to the maximum value observed in this study (~70), the measured increase of the nuclear diameter was specific to the region manifesting more advanced neoplastic development, in contrast to the ubiquitous and relatively constant cell nuclear diameter measurements of the plateau region.

The results highlight the importance of obtaining spatially resolved information for assessing tissue health. Other optical methods have also demonstrated the need for depth selectivity, but the specific depth that provides the most diagnostic information has varied. Using LEBS, which assesses changes in tissue nano-architecture, it was found that a penetration depth of 70 μm yielded the most significant results [58]; whereas using 4D ELF to measure hemoglobin concentrations, a penetration depth of 100 μm was found to yield significant results [56]. With these optical methods, however, useful information is obtained by integrating to a particular depth, rather than sampling specific locations, which may explain the differences. In contrast, fLCI is an interferometric technique that uses a broadband source, and thus enables the coherence gating imaging capabilities of OCT and allows sampling of specific points in three-dimensional space. Image guidance was vital in this study in order to identify the tissue surface and probe specific tissue depths.

Along with the imaging capabilities of fLCI, the DW technique is an equally important feature to enable this study. The DW technique avoids the spectral and spatial resolution trade-off that has hindered quantification using STFTs or continuous wavelet transforms. Acquisition of the local oscillations necessitates high resolution in both dimensions, otherwise the phenomenon of fringe washout, resulting from phase and frequency differences from different scattering nuclei, would obscure the local oscillations from which the cell nuclear diameter is assessed.

The results were analyzed by segments along the length of the colon. Here, fLCI detected significant changes in segments and at time points that presented early evidence of preneoplastic development, underscoring the sensitivity of the method. Further, the measured early nuclear morphological change was observed in both segments and independently of the number of ACF, which suggests a ubiquitous micro-morphological change of the colon. This, however, was not the case when neoplastic development became more advanced (demarcated by the high number ACF); at which point, the nuclear diameter increase was specific to the affected region. These sets of results present significant findings. First, these results suggest that fLCI may be able to detect the "field effect" of carcinogenesis. This phenomenon describes observations that neoplastic development in one part of the colon distorts nano- and micro-tissue morphology, as well as tissue function, along the entire organ. This has been a subject of much interest since it indicates that adequate screening may be achieved by only probing certain (and more readily accessible) sections of the colon [56, 58, 74]. These results also indicate that fLCI can identify specific regions where more advanced neoplastic development has occurred, which is paramount for detecting CRC development and initiating a localized therapy.

While the results presented here are very promising, there are certain limitations that still need to be explored in order to take advantage of all the information provided by the method. As described above, the procedure for obtaining fLCI measurements assumes a constant RI value for the cell nuclei, and a different constant value for the bulk tissue; however, it is known that the RI can vary depending on tissue type and tissue health. Thus, these variations, which are currently not assessed with our method, may be introducing an additional degree of uncertainty in the calculated nuclear diameters. Further, these variations have hindered our ability to use the low frequency oscillations with LSS, as previously performed using tissue phantoms [63]. However, it is believed that a more rigorous treatment of the LSS fitting algorithm may provide insight to the variations of the RI in future analyses.

In this study, an AOM-treated rat model was used to demonstrate the ability of fLCI to quantitatively distinguish between ex-vivo colon tissue that is normal and that which exhibits early precancerous development. The results show highly statistically significant differences between the AOM-treated and control group samples. Further, the results suggest that fLCI may be able to detect changes due to the field effect of carcinogenesis, in addition to identifying areas where more advanced neoplastic development has occurred. Future work will be directed towards developing an optical fiber based pfdOCT system to demonstrate non-invasive, in-vivo early CRC detection.

FIG. 42 is a schematic diagram representation of an exemplary machine 1420 in the exemplary form of an exemplary computer system 1422 adapted to execute instructions from an exemplary computer-readable medium to perform the functions of the DW techniques described herein according to one embodiment. The machine 1420 may be interfaced, for example, to the spectrographs described herein to receive scattering interference term information containing depth-resolved spectral information about a sample. In this regard, the machine 1420 may comprise the computer system 1422 within which a set of instructions for causing the machine 1420 to perform any one or more of the methodologies discussed herein may be executed. The machine 1420 may be connected (e.g., networked) to other machines in a local area network (LAN), an intranet, an extranet, or the Internet. The machine 1420 may operate in a client-server network environment, or as a peer machine in a peer-to-peer (or distributed) network environment. While only a single machine 1420 is illustrated, the term "machine" shall also be taken to include any collection of machines that individually or jointly execute a set (or multiple sets) of instructions to perform any one or more of the methodologies discussed herein. The machine 1420 may be a server, a personal computer, a desktop computer, a laptop computer, a personal digital assistant (PDA), a computing pad, a mobile device, or any other device and may represent, for example, a server or a user's computer.

The exemplary computer system 1422 includes a processing device or processor 1424, a main memory 1426 (e.g., read-only memory (ROM), flash memory, dynamic random access memory (DRAM) such as synchronous DRAM (SDRAM), etc.), and a static memory 1428 (e.g., flash memory, static random access memory (SRAM), etc.), which may communicate with each other via a bus 1430. Alternatively, the processing device 1424 may be connected to the main memory 1426 and/or static memory 1428 directly or via some other connectivity means.

The processing device 1424 represents one or more general-purpose processing devices such as a microprocessor, central processing unit, or the like. More particularly, the processing device 1424 may be a complex instruction set computing (CISC) microprocessor, a reduced instruction set computing (RISC) microprocessor, a very long instruction word (VLIW) microprocessor, a processor implementing other instruction sets, or processors implementing a combination of instruction sets. The processing device 1424 is configured to execute processing logic in instructions 1432 for performing the operations and steps discussed herein.

The computer system 1422 may further include a network interface device 1434. It also may or may not include an input 1436 to receive input and selections to be communicated to the computer system 1422 when executing instructions. It also may or may not include an output 1438, including but not limited to a display, a video display unit (e.g., a liquid crystal display (LCD) or a cathode ray tube (CRT)), an alphanumeric input device (e.g., a keyboard), and/or a cursor control device (e.g., a mouse).

The computer system 1422 may or may not include a data storage device that includes an analysis or FPE tool 1440 stored in a machine-accessible storage or computer-readable medium 1442 on which is stored one or more sets of instructions 1444 (e.g., software) embodying any one or more of the methodologies or functions described herein. The instructions 1444 may also reside, completely or at least partially, within the main memory 1426 and/or within the processing device 1424 during execution thereof by the computer system 1422, the main memory 1426 and the processing device 1424 also constituting machine-accessible storage media. The instructions 1444 may further be transmitted or received over a network 1446 via the network interface device 1434.

While the machine-accessible storage medium 1442 is shown in an exemplary embodiment to be a single medium, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that is capable of storing, encoding or carrying a set of instructions for execution by the machine and that cause the machine to perform any one or more of the methodologies of the embodiments disclosed herein. The term "machine-accessible storage medium" shall accordingly be taken to include, but not be limited to, solid-state memories, optical and magnetic media, and carrier wave signals.

Many modifications and other embodiments of the embodiments set forth herein will come to mind to one skilled in the art to which the embodiments pertain having the benefit of the teachings presented in the foregoing descriptions and the associated drawings. The present disclosure is not limited to dual windows. Multiple windows having more than two windows may be employed if desired. The present disclosure is not limited to particular properties of returned light from the sample. These optical properties can include scattering properties, reflectance properties, and absorption properties. Therefore, it is to be understood that the description and claims are not to be limited to the specific embodiments disclosed and that modifications and other embodiments are intended to be included within the scope of the described embodiments. Although specific terms are employed herein, they are used in a generic and descriptive sense only and not for purposes of limitation.

What is claimed is:

1. A method of obtaining depth-resolved spectra of a sample for determining scattering and absorption characteristics within the sample, comprising:

emitting a beam onto a splitter, wherein the splitter splits light from the beam to produce a reference beam, and an input beam to the sample;

cross-correlating the reference beam with a sample beam returned from the sample as a result of the input beam by mixing the reference beam and the returned sample beam from the sample to yield a cross-correlated profile having optical, depth-resolved information about the returned sample beam;

generating a spectroscopic depth-resolved profile that includes optical properties about the sample by:

providing first one or more spectroscopic windows of the cross-correlated profile, each of the first one or more spectroscopic windows having a first width at a given center wavelength to obtain optical information about the sample for each given center wavelength;

applying a Fourier transform to the optical information about the sample to recover high resolution optical information about the sample at each given center wavelength simultaneously;

providing second one or more spectroscopic windows of the cross-correlated profile, each of the second one or more spectroscopic windows having a second width greater than the first width at a given center wavelength to obtain absorption information about the sample for each given center wavelength;

applying a Fourier transform to the absorption information about the sample as a function of depth to recover high resolution depth information about the sample at each given center wavelength simultaneously; and co-registering the high resolution optical information and the high resolution depth information about the sample to yield a single high resolution spectroscopic optical-resolved, depth-resolved profile about the sample.

2. The method of claim 1, further comprising recovering scattering information about the sample from the spectroscopic depth-resolved profile.

3. The method of claim 2, wherein recovering the scattering information is obtained by measuring a frequency of a spectral modulation in the spectroscopic depth-resolved profile.

4. The method of claim 2, wherein recovering the scattering information is obtained by comparing the spectroscopic depth-resolved profile to a predicted analytical or numerical distribution of the sample.

5. The method of claim 1, wherein providing the first one or more spectroscopic windows is comprised of providing a first one or more Gaussian windows, a first one or more multiple simultaneous windows, or a first one or more other windows.

6. The method of claim 1, wherein providing the second one or more spectroscopic windows is comprised of providing a second one or more Gaussian windows, a second one or more multiple simultaneous windows, or a second one or more other windows.

7. The method of claim 1, wherein the splitter is comprised from the group consisting of a beam splitter and an optical fiber splitter.

8. The method of claim 1, wherein emitting a beam onto the splitter comprises emitting a collimated beam.

9. The method of claim 8, wherein the input beam comprises a collimated beam.

10. The method of claim 8, wherein the reference beam comprises a collimated beam.

11. The method of claim 1, wherein the beam is comprised of white light from an arc lamp, thermal source, or a super continuum laser.

12. The method of claim 1, wherein cross-correlating the reference beam with the returned sample beam comprises determining an interference term by measuring the intensity of the returned sample beam and the reference beam independently and subtracting them from the total intensity of the returned sample beam.

13. The method of claim 1, wherein the reference beam is reflected off of a reference mirror.

14. The method of claim 1, wherein the length of the path of the reference beam is fixed.

15. The method of claim 1, wherein the splitter is attached to a fixed reference arm.

16. The method of claim 1, wherein the sample is attached to a fixed sample arm.

17. The method of claim 1, wherein the returned sample beam is comprised of a scattered sample beam comprised of scattered light from scatterers in the sample.

18. The method of claim 17, further comprising spectrally dispersing the mixed reference beam and the scattered sample beam to yield a spectrally-resolved, depth-resolved cross-correlated profile having depth-resolved information about the scattered sample beam.

19. The method of claim 18, wherein the high resolution optical information is comprised of spectral information about the sample at each given center wavelength.

20. The method of claim 19, further comprising comparing the high resolution spectral information to known spectrum of one or more biological absorbers.

21. The method of claim 20, wherein the one or more biological absorbers comprises one or more contrast agents.

22. The method of claim 20, wherein the one or more biological absorbers are comprised of one or more particles.

23. The method of claim 20, wherein the one or more biological absorbers are comprised of nano-particles.

24. The method of claim 19, further comprising separating the high resolution spectral information into one or more color channels.

25. The method of claim 17, in which the scatterers are cell nuclei.

26. The method of claim 1, further comprising dispersing the mixed reference beam and the scattered sample beam using a spectrograph.

27. The method of claim 1, wherein the optical information includes scattering information about the sample.

28. An apparatus for obtaining depth-resolved information of a sample in order to determine the scattering and absorption characteristics within the sample, comprising:
a splitter configured to receive a reference beam and a returned sample beam containing light returned from a sample in response to the sample receiving a sample beam, wherein the splitter is further configured to cross-correlate the reference beam with the returned sample beam;
a detector configured to detect the cross-correlated reference beam and the returned sample beam to yield a cross-correlated profile having depth-resolved information about the returned sample beam; and
a processor configured to generate a spectroscopic depth-resolved profile that includes optical properties about the sample by:
providing first one or more spectroscopic windows of the cross-correlated profile, each of the first one or more spectroscopic windows having a first width at a given center wavelength to obtain optical information about the sample for each given center wavelength;
applying a Fourier transform to the optical information about the sample as a function of wavelength to recover high resolution optical information about the sample at each given center wavelength simultaneously;
providing second one or more spectroscopic windows of the cross-correlated profile, each of the second one or more spectroscopic windows having a second width greater than the first width at a given center wavelength to obtain absorption information about the sample for each given center wavelength;
applying a Fourier transform to the absorption information about the sample as a function of depth to recover high resolution depth information about the sample at each given center wavelength simultaneously; and
co-registering the high resolution optical information and the high resolution depth information about the sample to yield a single high resolution spectroscopic optical-resolved, depth-resolved profile about the sample.

29. The apparatus of claim 28, wherein the processor is further adapted to recover scattering information about the sample from the spectroscopic depth-resolved profile.

30. The apparatus of claim 28, wherein the processor is further adapted to recover scattering information by measuring a frequency of a spectral modulation in the spectroscopic depth-resolved profile.

31. The apparatus of claim 28, wherein the processor is further adapted to recover scattering information by comparing the spectroscopic depth-resolved profile to a predicted analytical or numerical scattering distribution of the sample.

32. The apparatus of claim 28, wherein providing the first one or more spectroscopic windows is comprised of providing a first one or more Gaussian windows, a first one or more multiple simultaneous windows, or a first one or more other window.

33. The apparatus of claim 28, wherein providing the second one or more spectroscopic windows is comprised of providing a second one or more Gaussian windows, a first one or more multiple simultaneous windows, or a second one or more other window.

34. The apparatus of claim 28, wherein the splitter is comprised from the group consisting of a beam splitter and an optical fiber splitter.

35. The apparatus of claim 28, wherein the sample beam comprises a collimated beam.

36. The apparatus of claim 28, wherein the reference beam comprises a collimated beam.

37. The apparatus of claim 28, wherein the received beam is comprised of one of a light comprised from the group consisting of a white light generated by an arc lamp or thermal source, and a super continuum laser.

38. The apparatus of claim 28, wherein a length of a path of the reference beam is fixed.

39. The apparatus of claim 28, wherein the splitter is attached to a fixed reference arm.

40. The apparatus of claim 28, wherein the sample is attached to a fixed sample arm.

41. The apparatus of claim 28, wherein the detector is comprised of a dispersive element.

42. The apparatus of claim 41, wherein the dispersive element is a spectrograph.

43. The apparatus of claim 28, wherein the returned sample beam is comprised of a scattered sample beam comprised of scattered light from scatterers in the sample.

44. The apparatus of claim 43, wherein the detector is adapted to spectrally disperse the mixed reference beam and the scattered sample beam to yield a spectrally-resolved cross-correlated profile having depth-resolved information about the scattered sample beam.

45. The apparatus of claim 43, in which the scatterers are cell nuclei.

46. The apparatus of claim 43, wherein the high resolution optical information is comprised of high resolution spectral information about the sample at each given center wavelength.

47. The apparatus of claim 46, wherein the processing is further adapted to compare the high resolution spectral information about the sample at each given center wavelength to known spectrum of one or more biological absorbers.

48. The apparatus of claim 47, wherein the one or more biological absorbers comprises one or more contrast agents.

49. The apparatus of claim 47, wherein the one or more biological absorbers are comprised of one or more particles.

50. The apparatus of claim 47, wherein the one or more biological absorbers are comprised of nano-particles.

51. The apparatus of claim 46, further comprising a spectrograph, wherein the spectrograph is configured to separate the high resolution spectral information into one or more color channels.

52. The apparatus of claim 28, wherein the optical information includes scattering information about the sample.

* * * * *